US011452450B2

(12) United States Patent
Bedell et al.

(10) Patent No.: US 11,452,450 B2
(45) Date of Patent: Sep. 27, 2022

(54) SYSTEM FOR FACILITATING ADMINISTRATION OF A PHARMACEUTICAL PRODUCT

(71) Applicants: Alfred Hyamo Bedell, Lansdowne, PA (US); Alice Bedell, Lansdowne, PA (US)

(72) Inventors: Alfred Hyamo Bedell, Lansdowne, PA (US); Alice Bedell, Lansdowne, PA (US)

(*) Notice: Subject to any disclaimer, the term of this patent is extended or adjusted under 35 U.S.C. 154(b) by 430 days.

(21) Appl. No.: 16/775,000

(22) Filed: Jan. 28, 2020

(65) Prior Publication Data
US 2020/0237223 A1 Jul. 30, 2020

Related U.S. Application Data
(60) Provisional application No. 62/797,891, filed on Jan. 28, 2019.

(51) Int. Cl.
*A61B 5/00* (2006.01)
*G16H 10/60* (2018.01)
(Continued)

(52) U.S. Cl.
CPC .......... *A61B 5/0022* (2013.01); *A61B 5/6801* (2013.01); *A61B 5/746* (2013.01);
(Continued)

(58) Field of Classification Search
CPC ..... A61B 5/0022; A61B 5/6801; A61B 5/746; A61B 2562/02; A61J 1/03; G16H 10/60; G16H 20/13; G16H 40/63
See application file for complete search history.

(56) References Cited

U.S. PATENT DOCUMENTS

2005/0277912 A1* 12/2005 John ................. A61M 5/16827
604/890.1
2006/0041248 A1* 2/2006 Patton ................. A61K 9/0014
604/890.1

FOREIGN PATENT DOCUMENTS

DE 19743031 A1 * 5/1999 ............ A61J 7/0481

OTHER PUBLICATIONS

Kaasi, Andreas; Cestari, Idágene A; Stolf, Noedir A G; Leirner, Adolfo A; Hassager, Ole; et al. "A new approach to heart valve tissue engineering: mimicking the heart ventricle with a ventricular assist device in a novel bioreactor." Journal of tissue engineering and regenerative medicine5.4: (Year: 2011).*

* cited by examiner

*Primary Examiner* — Linh Giang Le

(57) ABSTRACT

Disclosed herein is a system for facilitating administration of a pharmaceutical product. Accordingly, the system may include at least one sensor, a storage device, a processing device, and a Mobile Administration Interlocking Device (MAID). Further, the at least one sensor may be disposed on body of a user. Further, the at least one sensor may be configured for generating at least one physiological data associated with the body. Further, the storage device may be configured for storing at least one dosage data. Further, the at least one dosage data may be prescribed by a medical professional. Further, the processing device may be communicatively coupled with the at least one sensor. Further, the processing device may be communicatively coupled with the storage device. Further, the MAID may be configured for provisioning the pharmaceutical product to the user. Further, the MAID may be communicatively coupled with the processing device.

18 Claims, 38 Drawing Sheets

(51) Int. Cl.
*G16H 40/63* (2018.01)
*A61J 1/03* (2006.01)
*G16H 20/13* (2018.01)

(52) U.S. Cl.
CPC ............... *A61J 1/03* (2013.01); *G16H 10/60* (2018.01); *G16H 20/13* (2018.01); *G16H 40/63* (2018.01); *A61B 2562/02* (2013.01)

SYSTEM FOR FACILITATING ADMINISTRATION OF A PHARMACEUTICAL PRODUCT

The current application claims a priority to the U.S. Provisional Patent application Ser. No. 62/797,891 filed on Jan. 28, 2019.

TECHNICAL FIELD

Generally, the present disclosure relates to the field of mobile health devices. More specifically, the present disclosure relates to a system for facilitating administration of a pharmaceutical product.

BACKGROUND

Existing techniques for facilitating administration of a pharmaceutical product are deficient with regard to several aspects. For instance, current technologies do not help healthcare providers to create an effective recovery treatment plan for pregnant women. Furthermore, current technologies do not provide better addiction prevention strategies. Moreover, current technologies do not provide a secure distribution of prescribed opioid drugs. Further, current technologies do not provide a platform for instantaneous biofeedback about stressors and opioid usage.

Therefore, there is a need for an improved system for facilitating administration of a pharmaceutical product that may overcome one or more of the above-mentioned problems and/or limitations.

BRIEF SUMMARY

This summary is provided to introduce a selection of concepts in a simplified form, which are further described below in the Detailed Description. This summary is not intended to identify key features or essential features of the claimed subject matter. Nor is this summary intended to be used to limit the claimed subject matter's scope.

Disclosed herein is a block diagram of a system for facilitating administration of a pharmaceutical product, in accordance with some embodiments. Accordingly, the system may include at least one sensor, a storage device, a processing device, and a Mobile Administration Interlocking Device (MAID). Further, the at least one sensor may be disposed on the body of a user. Further, the at least one sensor may be configured for generating at least one physiological data associated with the body. Further, the storage device may be configured for storing at least one dosage data. Further, the at least one dosage data may be prescribed by a medical professional. Further, the at least one dosage data may be associated with the user. Further, the processing device may be communicatively coupled with the at least one sensor. Further, the processing device may be communicatively coupled with the storage device. Further, the processing device may be configured for analyzing the at least one physiological data and the at least one dosage data. Further, the processing device may be configured for determining a pharmaceutical dose of the pharmaceutical product corresponding to the user based on the analyzing. Further, the processing device may be configured for generating a command based on the determining. Further, the Mobile Administration Interlocking Device (MAID) configured for provisioning the pharmaceutical product to the user. Further, the MAID may be communicatively coupled with the processing device. Further, the MAID may include a first chamber and a first actuator. Further, the first chamber may be configured for accommodating the pharmaceutical product. Further, the first chamber may include a first opening. Further, the first opening facilitates dispensing of the pharmaceutical product. Further, the first actuator may be communicatively coupled with the processing device. Further, the first actuator may be operably coupled with the first chamber. Further, the first actuator may be configured for dispensing the pharmaceutical product. Further, the first actuator may be controlled by the processing device based on the command. Further, the first actuator may be configured to arrange in at least two states. Further, a first state of the at least two states facilitates dispensing of the pharmaceutical product. Further, a second state of the at least two states prevents access to the pharmaceutical product.

Further disclosed herein is a system for facilitating administration of an opioid, in accordance with some embodiments. Accordingly, the system may include at least one sensor, a storage device, a processing device, and a Mobile Administration Interlocking Device (MAID). Further, the at least one sensor may be disposed on the body of a user. Further, the at least one sensor may be configured for generating at least one physiological data associated with the body. Further, the storage device may be configured for storing at least one dosage data. Further, the at least one dosage data may be prescribed by a medical professional. Further, the at least one dosage data may be associated with the user. Further, the processing device may be communicatively coupled with the at least one sensor. Further, the processing device may be communicatively coupled with the storage device. Further, the processing device may be configured for analyzing the at least one physiological data and the at least one dosage data. Further, the processing device may be configured for determining a pharmaceutical dose of the opioid corresponding to the user based on the analyzing. Further, the processing device may be configured for generating a command based on the determining. Further, the Mobile Administration Interlocking Device (MAID) may be configured for provisioning the opioid to the user. Further, the MAID may be communicatively coupled with the processing device. Further, the MAID may include a first chamber and a first actuator. Further, the first chamber configured for accommodating the opioid. Further, the first chamber may include a first opening. Further, the first opening facilitates dispensing of the opioid. Further, the first actuator may be communicatively coupled with the processing device. Further, the first actuator may be operably coupled with the first chamber. Further, the first actuator may be configured for dispensing the opioid. Further, the first actuator may be controlled by the processing device based on the command. Further, the first actuator may be configured to arrange in at least two states. Further, a first state of the at least two states facilitates dispensing of the opioid. Further, a second state of the at least two states prevents access to the opioid.

Further disclosed herein is a system for facilitating administration of an opioid, in accordance with some embodiments. Accordingly, the system may include at least one sensor, a storage device, a processing device, and a Mobile Administration Interlocking Device (MAID). Further, the at least one sensor may be disposed on the body of a user. Further, the at least one sensor may be configured for generating at least one physiological data associated with the body. Further, the storage device may be configured for storing at least one dosage data. Further, the at least one dosage data may be prescribed by a medical professional. Further, the at least one dosage data may be associated with the user. Further, the processing device may be communicatively coupled with the at least one sensor. Further, the processing device may be communicatively coupled with the storage device. Further, the processing device may be configured for analyzing the at least one physiological data and the at least one dosage data. Further, the processing device may be configured for determining a pharmaceutical dose of the opioid corresponding to the user based on the analyzing. Further, the processing device may be configured for generating a command based on the determining. Further, the Mobile Administration Interlocking Device (MAID) may be configured for provisioning the opioid to the user. Further, the MAID may be communicatively coupled with the processing device. Further, the MAID may include a first chamber, a first actuator, and a second chamber. Further, the first chamber may be configured for accommodating the opioid. Further, the first chamber may include a first opening. Further, the first opening facilitates dispensing of the opioid. Further, the first actuator may be communicatively coupled with the processing device. Further, the first actuator may be operably coupled with the first chamber. Further, the first actuator may be configured for dispensing the opioid. Further, the first actuator may be controlled by the processing device based on the command. Further, the first actuator may be configured to arrange in at least two states. Further, a first state of the at least two states facilitates dispensing of the opioid. Further, a second state of the at least two states prevents access to the opioid. Further, the second chamber may be configured for accommodating an opioid antagonist. Further, the second chamber may include a second sensor. Further, the second sensor may be configured for detecting an invalid dispensing action associated with the second chamber. Further, the second chamber may include a second actuator. Further, the second sensor may be coupled with the second actuator. Further, the second actuator may be communicatively coupled with the processing device. Further, the second actuator may be configured for controlling dispensing of the opioid antagonist based on the detection of the invalid dispensing action. Further, the dispensing of the opioid antagonist facilitates the neutralizing of the opioid.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and subcombinations described in the detailed description.

BRIEF DESCRIPTION OF DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure.

DETAILED DESCRIPTION

Figure 1:
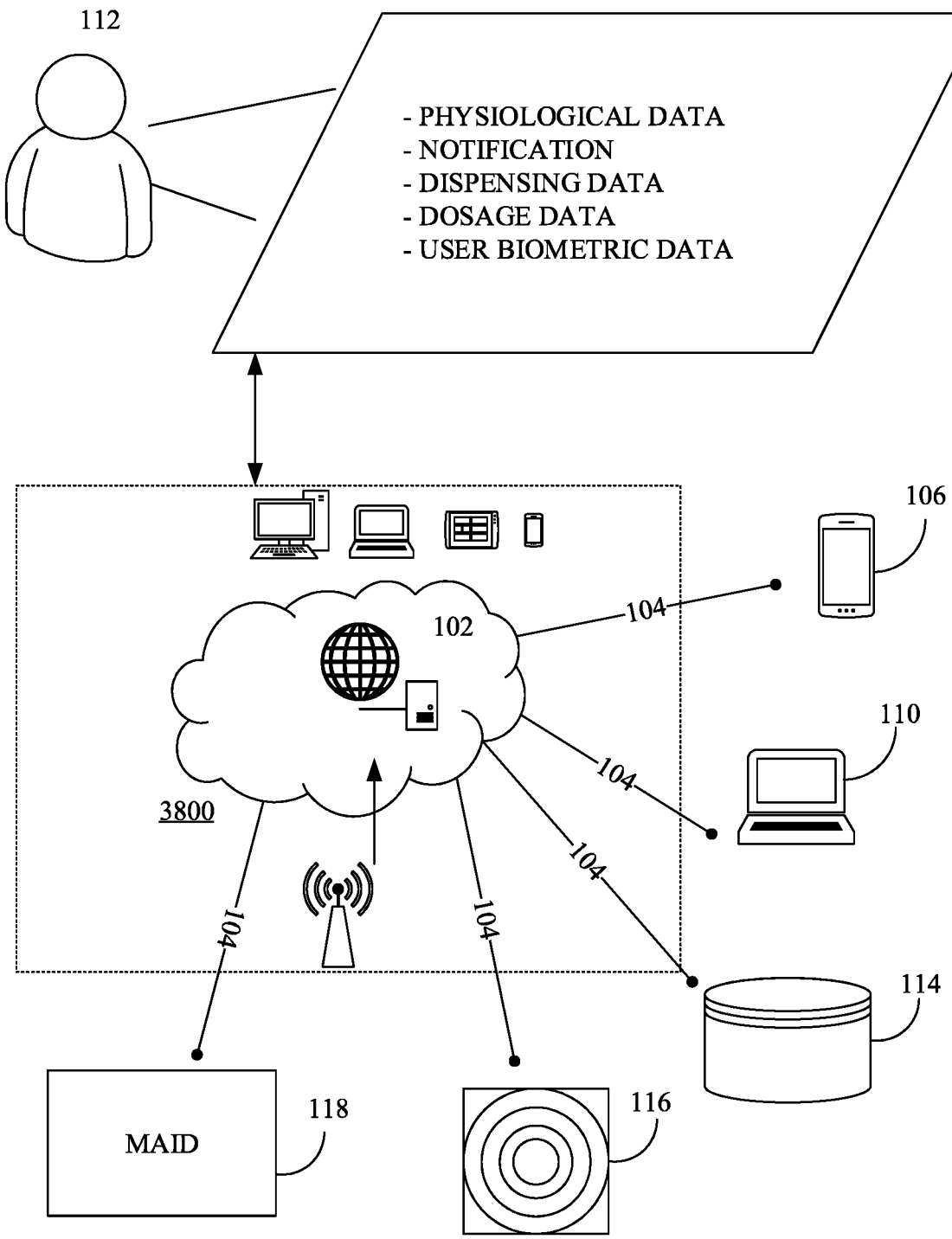
FIG. 1 is an illustration of an online platform consistent with various embodiments of the present disclosure.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim limitation found herein and/or issuing here from that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the claims found herein and/or issuing herefrom. The present disclosure contains headers. It should be understood that these headers are used as references and are not to be construed as limiting upon the subjected matter disclosed under the header.

The present disclosure includes many aspects and features. Moreover, while many aspects and features relate to, and are described in the context of a system for facilitating administration of a pharmaceutical product, embodiments of the present disclosure are not limited to use only in this context.

In general, the method disclosed herein may be performed by one or more computing devices. For example, in some embodiments, the method may be performed by a server computer in communication with one or more client devices over a communication network such as, for example, the Internet. In some other embodiments, the method may be performed by one or more of at least one server computer, at least one client device, at least one network device, at least one sensor, and at least one actuator. Examples of the one or more client devices and/or the server computer may include, a desktop computer, a laptop computer, a tablet computer, a personal digital assistant, a portable electronic device, a wearable computer, a smartphone, an Internet of Things (IoT) device, a smart electrical appliance, a video game console, a rack server, a super-computer, a mainframe computer, mini-computer, micro-computer, a storage server, an application server (e.g. a mail server, a web server, a real-time communication server, an FTP server, a virtual server, a proxy server, a DNS server, etc.), a quantum computer, and so on. Further, one or more client devices and/or the server computer may be configured for executing a software application such as, for example, but not limited to, an operating system (e.g. Windows, Mac OS, Unix, Linux, Android, etc.) in order to provide a user interface (e.g. GUI, touch-screen based interface, voice-based interface, gesture-based interface etc.) for use by the one or more users and/or a network interface for communicating with other devices over a communication network. Accordingly, the server computer may include a processing device configured for performing data processing tasks such as, for example, but not limited to, analyzing, identifying, determining, generating, transforming, calculating, computing, compressing, decompressing, encrypting, decrypting, scrambling, splitting, merging, interpolating, extrapolating, redacting, anonymizing, encoding and decoding. Further, the server computer may include a communication device configured for communicating with one or more external devices. The one or more external devices may include, for example, but are not limited to, a client device, a third-party database, public database, a private database and so on. Further, the communication device may be configured for communicating with the one or more external devices over one or more communication channels. Further, the one or more communication channels may include a wireless communication channel and/or a wired communication channel. Accordingly, the communication device may be configured for performing one or more of transmitting and receiving of information in electronic form. Further, the server computer may include a storage device configured for performing data storage and/or data retrieval operations. In general, the storage device may be configured for providing reliable storage of digital information. Accordingly, in some embodiments, the storage device may be based on technologies such as, but not limited to, data compression, data backup, data redundancy, deduplication, error correction, data fingerprinting, role-based access control, and so on.

Further, one or more steps of the method disclosed herein may be initiated, maintained, controlled and/or terminated based on a control input received from one or more devices operated by one or more users such as, for example, but not limited to, an end-user, an admin, a service provider, a service consumer, an agent, a broker and a representative thereof. Further, the user as defined herein may refer to a human, an animal or an artificially intelligent being in any state of existence, unless stated otherwise, elsewhere in the present disclosure. Further, in some embodiments, the one or more users may be required to successfully perform authentication in order for the control input to be effective. In general, a user of the one or more users may perform authentication based on the possession of a secret human-readable secret data (e.g. username, password, passphrase, PIN, secret question, secret answer, etc.) and/or possession of a machine-readable secret data (e.g. encryption key, decryption key, bar codes, etc.) and/or possession of one or more embodied characteristics unique to the user (e.g. biometric variables such as, but not limited to, fingerprint, palm-print, voice characteristics, behavioral characteristics, facial features, iris pattern, heart rate variability, evoked potentials, brain waves, and so on) and/or possession of a unique device (e.g. a device with a unique physical and/or chemical and/or biological characteristic, a hardware device with a unique serial number, a network device with a unique IP/MAC address, a telephone with a unique phone number, a smartcard with an authentication token stored thereupon, etc.). Accordingly, the one or more steps of the method may include communicating (e.g. transmitting and/or receiving) with one or more sensor devices and/or one or more actuators in order to perform authentication. For example, the one or more steps may include receiving, using the communication device, the secret human-readable data from an input device such as, for example, a keyboard, a keypad, a touch-screen, a microphone, a camera and so on. Likewise, the one or more steps may include receiving, using the communication device, the one or more embodied characteristics from one or more biometric sensors.

Further, one or more steps of the method may be automatically initiated, maintained and/or terminated based on one or more predefined conditions. In an instance, the one or more predefined conditions may be based on one or more contextual variables. In general, the one or more contextual variables may represent a condition relevant to the performance of the one or more steps of the method. The one or more contextual variables may include, for example, but are not limited to, location, time, identity of a user associated with a device (e.g. the server computer, a client device, etc.) corresponding to the performance of the one or more steps, environmental variables (e.g. temperature, humidity, pressure, wind speed, lighting, sound, etc.) associated with a device corresponding to the performance of the one or more steps, physical state and/or physiological state and/or psychological state of the user, physical state (e.g. motion, direction of motion, orientation, speed, velocity, acceleration, trajectory, etc.) of the device corresponding to the performance of the one or more steps and/or semantic content of data associated with the one or more users. Accordingly, the one or more steps may include communicating with one or more sensors and/or one or more actuators associated with the one or more contextual variables. For example, the one or more sensors may include, but are not limited to, a timing device (e.g. a real-time clock), a location sensor (e.g. a GPS receiver, a GLONASS receiver, an indoor location sensor, etc.), a biometric sensor (e.g. a fingerprint sensor), an environmental variable sensor (e.g. temperature sensor, humidity sensor, pressure sensor, etc.) and a device state sensor (e.g. a power sensor, a voltage/current sensor, a switch-state sensor, a usage sensor, etc. associated with the device corresponding to performance of the or more steps).

Further, the one or more steps of the method may be performed one or more number of times. Additionally, the one or more steps may be performed in any order other than as exemplarily disclosed herein, unless explicitly stated otherwise, elsewhere in the present disclosure. Further, two or more steps of the one or more steps may, in some embodiments, be simultaneously performed, at least in part. Further, in some embodiments, there may be one or more time gaps between performances of any two steps of the one or more steps.

Further, in some embodiments, the one or more predefined conditions may be specified by the one or more users. Accordingly, the one or more steps may include receiving, using the communication device, the one or more predefined conditions from one or more and devices operated by the one or more users. Further, the one or more predefined conditions may be stored in the storage device. Alternatively, and/or additionally, in some embodiments, the one or more predefined conditions may be automatically determined, using the processing device, based on historical data corresponding to performance of the one or more steps. For example, the historical data may be collected, using the storage device, from a plurality of instances of performance of the method. Such historical data may include performance actions (e.g. initiating, maintaining, interrupting, terminating, etc.) of the one or more steps and/or the one or more contextual variables associated therewith. Further, machine learning may be performed on the historical data in order to determine the one or more predefined conditions. For instance, machine learning on the historical data may determine a correlation between one or more contextual variables and performance of the one or more steps of the method. Accordingly, the one or more predefined conditions may be generated, using the processing device, based on the correlation.

Further, one or more steps of the method may be performed at one or more spatial locations. For instance, the method may be performed by a plurality of devices interconnected through a communication network. Accordingly, in an example, one or more steps of the method may be performed by a server computer. Similarly, a client computer may perform one or more steps of the method. Likewise, one or more steps of the method may be performed by an intermediate entity such as, for example, a proxy server. For instance, one or more steps of the method may be performed in a distributed fashion across the plurality of devices in order to meet one or more objectives. For example, one objective may be to provide load balancing between two or more devices. Another objective may be to restrict a location of one or more of an input data, an output data and any intermediate data there between corresponding to one or more steps of the method. For example, in a client-server environment, sensitive data corresponding to a user may not be allowed to be transmitted to the server computer. Accordingly, one or more steps of the method operating on the sensitive data and/or a derivative thereof may be performed at the client device.

OVERVIEW

The present disclosure describes a system for facilitating administration of a pharmaceutical product. Further, the disclosed system may provide a platform for instantaneous biofeedback about stressors and opioid usage, and may further facilitate the development of interceptive strategies. In addition, the disclosed system may provide a mechanism for safe and effective prescription opioid administration.

Further, the disclosed system may provide valuable feedback needed to develop effective treatment plans and assist with the drug recovery process. In addition, the disclosed system may integrate the generated data into the electronic medical records (EMR) database. This allows the system to conduct cognitive learning about a user, and provide valuable information for better overall health management.

The present disclosure may be a continuation of a digital health system for the continuous quantification of physiological biomarkers, biological regulators, and analytes in real-time. The present disclosure may describe a technology that may be an integrated non-invasive health monitoring system that tracks stress (i.e. salivary Cortisol hormone or physiological markers such as temperature, respiration, and heart rate) and pharmaceutical product (i.e., opioids) usage in real-time. In addition, an integrated platform may provide a mechanism for telemedicine dispensing of pharmaceutical products (liquid and solid medication) in a controlled manner. Further, the disclosed system may consist of a wearable hardware device, disposable bio-cartridges, mobile app software, and a mobile administration-interlocking device (MAID).

Further, the disclosed system may provide better addiction prevention strategies. It also creates generalized knowledge about stress-induced overdose, provides supports for alternative pain management, creates a pharmaceutical product usage profile, and may identify a risk associated with individuals for substance use disorder.

Further, the MAID may provide a secured distribution of prescribed opioid drugs. A pharmacist may pre-fill the MAID using liquid or solid opioid dosage (e.g. Oxycodone Oral Liquid or Morphine Sulfate Liquid). A separate chamber in the MAID may be filled with an opioid antagonist (e.g. Naloxone hydrochloride). Further, the MAID may also administer solid medications. The prescribing physician may remotely set the dosage (concentration and frequency) using an app. Prior to distributing a dosage, the user must authenticate their identity by verifying fingerprint with a biometric scanner. Once authenticated, the sensors may do a qualitative measurement of the user's current opioid baseline (sensitivity limit of 35 ng/mL). If the user is at or above the sensitivity limit, they will not be administered a dosage. However, if the user is below the limit, a single dosage will be administered. A successful notification will be sent to the API and third parties (e.g., Physicians). If noncompliant activity is identified, the MAID will pump high dosage opioid antagonists to neutralize the liquid opioid. If using a solid dosage, the MAID will expel a deterrent solution into the medication disk, thus forming a harden deterrent and substrate complex locking the medication within the disk. In addition, the MAID will shut down and send a notification to third parties (e.g. Police, Physician, etc.) of potential device tampering. Further, the disclosed system may have two modes, outpatient and inpatient monitoring. Further, the MAID may be designed to act as a deterrent for potential opioid abusers, and at the same time, reduce or eliminate the adverse effects (AE) to non-abusive compliant patients. Unlike abuse-deterrent formulations (ADFs) opioids, which are misused by exceeding the prescribed dosage, the MAID prohibits the administration of the drug once the noncompliant activity is detected or if the end-user is over a specific opioid profile threshold. An example of predicate devices include Patient-controlled infusion pumps. Much like the predicate product, the MAID is a non-implanted, non-life-sustained/support device, which allows self-delivery of pain medication. Unlike the predicate product, the MAID may provide added protection for patients by establishing an opioid profile and baseline measurement prior to drug administration. This added safety measure may prevent opioid misuse by patients and ultimately may prevent opioid use disorder (OUD).

Further, the disclosed system may provide valuable feedback information needed to develop effective treatment plans and may assist with the recovery process. In addition, it integrates the generated data into electronic medical records (EMR). This works by uploading data from the app into a secure API. Next, the disclosed system may integrate the data into a query, and compute hypothetical analysis of possible interceptive strategies by scoring current evidence-based strategies for people with common health-related statuses. Finally, the solution with the highest confidence score may be pulsed back to the user via a device. More importantly, since the solution is unloaded using encrypted technology, both user and third parties may be able to monitor the interceptive strategies and securely track the progression of overall health.

By knowing the triggers' stressors of a user, the proposed technology may be able to assist in the process of modifying stress responses in various social settings. Further, the disclosed system may help healthcare providers to create an effective recovery treatment plan for pregnant women. Further, the disclosed system may be designed to assist in the propagation of better health through Cognitive-behavioral therapy (CBT). Further, the CBT is a psychotherapy treatment that focuses on modifying disruptive emotional contexts such as negative thoughts and replacing them with positive actionable steps. A mobile app may utilize CBT to build intrinsic motivation, thereby encouraging women to obtain greater emotional intelligence (EQ). Higher EQ can reduce occupational stress, improves self-awareness, and heighten decision-making skills. Healthcare professionals may be able to use the disclosed system during prenatal screening to identify patients at risk of developing OUD.

Further, the disclosed system may build valuable skills to improve emotional intelligence (EQ). Due to neuroplasticity, or the ability for the brain to change, users can improve their reaction to stressful events through interactive gaming app and feedback. High EQ may reduce occupational stress, and improve decision-making skills. Women can add daily notes to document the experience, and build a cohesive stress journal. Further, the app may also provide intervention for elevated stressful events. The platform may assist in decreasing OUD by identifying triggers that stimulate drug misuse. By documenting reoccurring patterns, women, along with licensed healthcare professionals, can formulate OUD treatment plans to eliminate the identified stress triggers, and ultimately, reduce opioid dependence. Moreover, the technology addresses a significant identified opioid treatment barrier such as the limited access to rehabilitation programs in rural areas. Further, the app may provide educational resources to professionals and health workers in rural areas. In addition, the disclosed system may deliver telemedicine services such as consultation, health assessments, and remote opioid usage monitoring. Further, the present disclosure may help: (1) increase the number of individuals seeking and receiving treatment for OUD, (2) provide reliable POC quantification of biometric data. (3) identify at-risk individuals for opioid misuse. (4) assist in the reduction of opioid abuse and chronic stress, and (5) reduce economic and societal costs associated with the over 2 million cases of OUD. Overall, the U-Check-It™ may connect pregnant women to licensed healthcare professionals. In addition, the U-Check-It™ may improve the coping ability of patients during substance abuse recovery by providing real-time progression status. Further, the U-Check-It™ may also create generalized data about stress-induced opioids overdose, provide supports for alternative pain management, and identify at-risk individuals for opioid use disorder (OUD).

The broader impact/commercial potential of the disclosed system may be to help the roughly 2 million people in the USA diagnosed with opioid use disorder (OUD) to reduce their consumption of opioids and better management of stress.

Now describing the present disclosure in more detail, a pharmacist prefills the MAID agonist reservoir with a pharmaceutical liquid medication such as an opioid dosage (e.g. Oxycodone Oral Liquid or Morphine Sulfate Liquid). An antagonist reservoir in the MAID device is filled with a pharmaceutical antagonist such as an opioid antagonist (e.g. Naloxone hydrochloride). The Solid Medication Administration Disk is filled with a solid pharmaceutical medication such as a pill or tablet. The MAID device can be used with adverse deterrent formulations (ADF) or extended-release formulation opioids. The pharmacist gains access to the MAID device by verifying their identity via a third party MICD and app. If their credentials are authenticated, the solenoid access bolt will retract, thereby releasing the lockbox. The prescribing physician remotely sets the dosage (concentration and frequency) using the app via a third-party MICD. The request is pushed to the API and downloaded onto the users MICD. When the user logs into the app, the updated dosage profile will be synced with the MAID once calibration and baseline measurement is established. Prior to distributing a dosage, the user must authenticate their identity by verifying fingerprint with a biometric scanner. Once authenticated, the sensors will do a qualitative measurement of the user's current opioid baseline (sensitivity limit of 35 ng/mL) using a bioassay cartridge and the biological reader or by scanning with the mobile phone. If the user is at or above the sensitivity limit, they will not be administered dosage and the event will be logged into the API. However, if the user is below the set limit, a single prescribed dosage will be administered. The liquid medication dosage is administered by activating the circulation pump and releasing clamp B, thereby pumping filtered air into the agonist reservoir. The air displaces the liquid and pushes it past the flow sensor. The flow sensor quantifies the volume of liquid expelled from the agonist reservoir. Once the required liquid dosage volume has been pumped into the liquid dispense cup, a signal will be sent to the microcontroller, and the circulation pump will deactivate and clamp B will clamp the passage tubes. If solid medication has been prescribed, the spin roller will activate, thus rotating the solid medication administration disk until the required number of solid medication is deposited to the Solid Medication Guard Platform. The microcontroller will verify the amount of solid medication deposited by quantifying with the laser solid medication counter and the Photodiode/light-dependent resistor. If the value matches the physician's prescription for the authenticated user, the Solid Medication Guard Platform will retract, dropping the solid dosage into the solid dispense cup. A successful notification of medication administration will be sent to the API and third parties (i.e., Physicians) MICD.

To maintain the integrity of the system and protect the pharmaceutical products, the MAID device has preconfigured safety protocols. When the MAID device is exposed to extremes in temperature or physical force, the safety protocols will be executed. In addition, when perceived unauthorized forced entry is identified by the system, the safety protocols will also be executed. During the execution of the safety protocols, the MAID device will pump high dosage opioid antagonists to neutralize the agonist. This is achieved by activating the circulation pump and releasing clamp A, thus pumping filtered air via the tubing T connector into the antagonist reservoir. The filtered air will displace the liquid antagonist, and pump it out of the antagonist reservoir and into the agonist reservoir via the bag coupler connector. Once cycled, clamp A will clamp the passage tube, and the circulation pump will deactivate. The antagonist will neutralize the pharmaceutical effects of the agonist so that it will not be misused or abused. If utilizing solid medication, the actuator arm will pulse thereby stroking the plunger of the syringe into the compressed position. The syringe is prefilled with a deterrent compound. The solid medication is held within a deterrent and substrate complex following the release of the deterrent compound from the deterrent pores. The deterrent compound is a non-metallic substance capable of bonding multiple substrates using the properties of adhesion and cohesion. The deterrent compound may be composed of organic polymers in a liquid or semi-liquid state, and once cured, may become solidified. Known materials that may assume the role of the deterrent compound include adhesives, epoxy and sealant compounds. During a noncompliant activity, the MAID's microcontroller will activate the actuator arm, thus expelling the entire contents of the syringe into the solid medication administration disk via the deterrent pores. The substrate in this interaction is the solid medication. Once the deterrent compound encounters the substrate, there will be adhesion of the deterrent compounds to the solid medication. Based on the properties of the deterrent compound, the adhesion may be rapid, thereby forming the harden deterrent and substrate complex. The inner volume of the medication disk will be displaced by the cohesion of the deterrent compound. In addition, top and bottom assemblies of the disk will be sealed shut due to adhesion between the deterrent compound and the disk material. The MAID will shut down and send a notification to third parties (e.g. Police, Physician) of potential device tampering. The high pitch audible alarm buzzer will sound until third party MICD or app deactivates it. An added safety measure of the MAID device is a low power warning. If the battery is depleted to a predefined level, the safety protocols will be executed.

The system has two modes, outpatient and inpatient monitoring. The MAID is designed to act as a deterrent for potential opioid abusers, and at the same time, reduce or eliminate the adverse effects (AE) to non-abusive compliant patients. Unlike abuse-deterrent formulations (ADFs) opioids, which can be misused by exceeding prescribed dosage, the MAID prohibits the administration of the drug once a noncompliant activity is identified or if the end-user is over a specific pharmaceutical product profile threshold.

In more detail, referring now to the disclosed digital health system, are diagrams that include devices, systems, apparatuses, and computer program products according to various embodiments of the present invention. It shall be understood that each step of the diagram, flowchart, and control flow illustrations, can be implemented by computer program instructions or other means. Although computer program instructions are discussed, an apparatus or system according to the present invention can include other means, such as hardware or some combination of hardware and software, including one or more processors or controllers, for performing the disclosed functions.

In this regard, the computer devices of various embodiments, each containing several of the key components of a general-purpose computer by which an embodiment of the present invention may be implemented. Those of ordinary skill in the art will appreciate that a computer can include many components. However, it is not necessary that all of these generally conventional components be shown in order to disclose an illustrative embodiment for practicing the invention. The general-purpose computer such as smartphones, tablets, and smartwatches can include a processing unit and a system memory, which may include various forms of non-transitory storage media such as random access memory (RAM) and read-only memory (ROM). The computer also may include nonvolatile storage memory, such as a hard disk drive, where additional data can be stored.

It shall be understood that the above-mentioned components of the mobile application unit are to be interpreted in the most general manner.

For example, the processor can include a single physical microprocessor or microcontroller, a cluster of processors, a datacenter or a cluster of data centers, a computing cloud service, and the like.

In a further example, the non-transitory memory can include various forms of non-transitory storage media, including random access memory and other forms of dynamic storage, and hard disks, hard disk clusters, cloud storage services, and other forms of long-term storage. Similarly, the input/output can include a plurality of well-known input/output devices, such as screens, keyboards, pointing devices, motion trackers, communication ports, and so forth. This can include system access to common functions and hardware, such as for example via operating system layers such as Windows, Linux, and similar operating system software, but can also include configurations wherein application services are executing directly on server hardware or via a hardware abstraction layer other than a complete operating system. An embodiment of the present invention can also include one or more input or output components, such as a mouse, keyboard, monitor, and the like. A display can be provided for viewing text and graphical data, as well as user interface to allow a user to request specific operations. Furthermore, an embodiment of the present invention may be connected to one or more remote computers via a network interface. The connection may be over a local area network (LAN) wide area network (WAN) and can include all of the necessary circuitry for such a connection. In a related embodiment, the wearable device can communicate over a network, a set of network connections, or direct connections, which can include the general Internet, a Wide Area Network or a Local Area Network, or another form of communication network, transmitted on wired or wireless connections. Wireless networks can, for example, include Ethernet, Wi-Fi, Bluetooth, ZigBee, and NFC.

Typically, computer program instructions may be loaded onto the computer or other general-purpose programmable machine to produce a specialized machine, such that the instructions that execute on the computer or other programmable machine create means for implementing the functions specified in the block diagrams, schematic diagrams or flowcharts. Such computer program instructions may also be stored in a computer-readable medium that when loaded into a computer or other programmable machine can direct the machine to function in a particular manner, such that the instructions stored in the computer-readable medium produce an article of manufacture including instruction means that implement the function specified in the block diagrams, schematic diagrams or flowcharts.

In addition, the computer program instructions may be loaded into a computer or other programmable machine to cause a series of operational steps to be performed by the computer or other programmable machine to produce a computer-implemented process, such that the instructions that execute on the computer or other programmable machine provide steps for implementing the functions specified in the block diagram, schematic diagram, flowchart block or step.

Accordingly, steps of the block diagram, flowchart or control flow illustrations support combinations of means for performing the specified functions, combinations of steps for performing the specified functions and program instruction means for performing the specified functions. It will also be understood that each block or step of the diagrams, schematic diagrams or flowcharts, as well as combinations of blocks or steps, can be implemented by special purpose hardware-based computer systems, or combinations of special purpose hardware and computer instructions, that perform the specified functions or steps.

As an example, provided for purposes of illustration only, a data input software tool of a search engine application can be a representative means for receiving a query including one or more search terms. Similar software tools of applications, or implementations of embodiments of the present invention, can be means for performing the specified functions. For example, an embodiment of the present invention may include computer software for interfacing a processing element with a user-controlled input device, such as a mouse, keyboard, touch screen display, scanner, or the like. Similarly, an output of an embodiment of the present invention may include, for example, a combination of display software, video card hardware, and display hardware. A processing element may include, for example, a controller or microprocessor, such as a central processing unit (CPU), arithmetic logic unit (ALU), or control unit.

Case Study

Cortisol, the end-result of the hypothalamic-pituitary-adrenocortical (HPA) axis, is a potential intercessor in understanding the connection between living a healthy life and managing pain. The HPA response in humans provides a mechanism for managing internal and external stressors. However, the continuous activation of the HPA system due to "chronic stress" and "poor pain management" leads to the development of allostatic load or excessive wear on the body. Abnormal Cortisol concentration is an effective biomarker for identifying uncontrolled pain. Cortisol levels usually become elevated during acute pain. When the pain turns chronic, the HPA axis continues to activate, resulting in higher Cortisol levels. If the pain is not controlled, the HPA axis becomes suppressed, causing blockage of Cortisol secretion. This, in turn, causes severe drops in Cortisol levels. In addition, the binding of opioid receptors is dependent upon adrenal corticoids. Patients with abnormal Cortisol levels may attempt to compensate for opioid unresponsiveness by exceeding the prescribed dosage. Abnormal Cortisol levels are also a good indicator of hypotension, insomnia, poor pain control, hyperalgesia, diabetes, hypertension, and hyperlipidemia.

Chronic stress affects the health of pregnant women and their unborn children. The American College of Obstetricians and Gynecologists stated that stress and anxiety may cause premature delivery and low birth weight. Stress also leads to postpartum depression in mothers. Almost 40% of women reported symptoms of depression at least once during pregnancy. Factors such as socioeconomic status and racial demographics may affect the degree of stress felt during pregnancy. Minority women reported having higher stress levels during pregnancy than white women. More specifically, women identified as Hispanic had significantly higher stress levels leading to increased perinatal problems.

There is a noted correlation between chronic stress and the impulse to abuse drugs. Chronic stress causes severe depression, which is one of the major risk factors for developing opioid dependence. Chronic stress dampens patients' ability to control cognitive functions such as impulse control, memory, and learning. Most opioid abusers use the euphoric properties of the drug as a coping mechanism for stress and depression. Continual high dosages of the drug tend to affect the region of the brain responsible for managing stress. Studies show that during episodes of emotional stress, substance abusers tend to have increased activity in the caudate and dorsal striatum regions and limited activity in the paralimbic and parahippocampal regions. Traumatic events such as emotional abuse, violence, and sexual abuse are more common among patients who misuse opioids. A study in Australia identified that more than 87% of patients with Opioid use disorder (OUD) had a previous traumatic experience. For every 100,000 patients prescribed opioids, about 10% will develop depression as a side effect to the drug. Determining the degree of depression may assist in identifying patients at risk for OUD and opioid misuse. A study done on risk factors for opioid addiction relapse revealed that 50% of relapse was due to depression, and that severe to very severe depression was a contributing cause of relapse for over 23% of the study participants. Even though stress negatively influences substance use, there has been no system designed to categorize stressors to a particular type of substance abuse. OUD, sometimes caused by the unintentional abuse of prescribed opioid pain medicine, is a major health crisis that affects the lives of over 2 million Americans. Addiction to opioids may lead to heroin dependence. About 80% of heroin users started their addiction by misusing prescription opioids. Studies estimated that almost 600.000 people had an OUD because of heroin abuse. The progression of opioid overdose-related deaths amplified to 265% for men and 400% for women since 1999.

Pregnant women who had an OUD usually exhibited concurring symptoms of chronic stress and depression. Almost 50% of mothers in substance abuse treatment stated that they suffered from postpartum depression. Additionally, about one-third of mothers treated for substance abuse reported having severe depression. Maternal opioid use per 1,000 births had increased from 1.19 in the year 2000 to 5.63 in 2009. Women in this category have a higher probability of abusing substances such as opioids. Women ages 15 to 44 who had abused substances increased to over 98.000 since 2011. The number of women abusing heroin increased to over 109.000 since 2013. That represents an increase of 31%. Mothers who abuse opioids while pregnant have a higher potential of giving birth to a child with neonatal abstinence syndrome (NAS). The current statistics suggest that one baby will suffer from NAS every 25 minutes. Newborns with NAS spend on average 16.9 days in the hospital, costing an additional 1.5 billion. Medicaid paid more than 80% of these fees, representing the fact that a greater population of opioid abusers are low-income.

The Center for Behavioral Health Statistics and Quality stated that almost 2 million people ages 12 and older had a substance use disorder in 2017. Yet, only half of them received treatment for the disorder. Even more disturbing, only 28% of those with OUD had received treatment in 2017. The CDC estimated that there were over 47,000 deaths related to opioid overdose in 2017 and that the majority had been unintended. The 2017 National Survey on Ding Use and Health stated that 45% of substance abusers had a mental disorder diagnosis and that only 51% were actively receiving treatment for either disorder. The lack of appropriate treatment channels has compounded the progression of OUD. The current healthcare system in the USA is not fully equipped to combat the challenges of substance use disorder, especially OUD. The staff are underprepared, understaffed, and not properly trained to prevent opioid misuse. In addition, the over-prescription of opioids has accelerated the misuse of the drug. Alternative pain management systems such as therapy, exercise, and less addictive substances should be utilized before distributing opioids. In addition, inequalities to affordable care and treatment options make it impossible to provide preventive screenings for substance abuse during prenatal appointments.

Referring now to figures, FIG. 1 is an illustration of an online platform 100 consistent with various embodiments of the present disclosure. By way of non-limiting example, the online platform 100 to facilitate administration of a pharmaceutical product may be hosted on a centralized server 102, such as, for example, a cloud computing service. The centralized server 102 may communicate with other network entities, such as, for example, a mobile device 106 (such as a smartphone, a laptop, a tablet computer, etc.), other electronic devices 110 (such as desktop computers, server computers, etc.), databases 114, sensors 116, and Mobile Administration-Interlocking Devices (MAID) 118 over a communication network 104, such as, but not limited to, the Internet. Further, users of the online platform 100 may include relevant parties such as, but not limited to, end-users, administrators, service providers, service consumers, and so on. Accordingly, in some instances, electronic devices operated by the one or more relevant parties may be in communication with the platform.

A user 112, such as the one or more relevant parties, may access online platform 100 through a web-based software application or browser. The web-based software application may be embodied as, for example, but not be limited to, a website, a web application, a desktop application, and a mobile application compatible with a computing device 3800.

Figure 2:
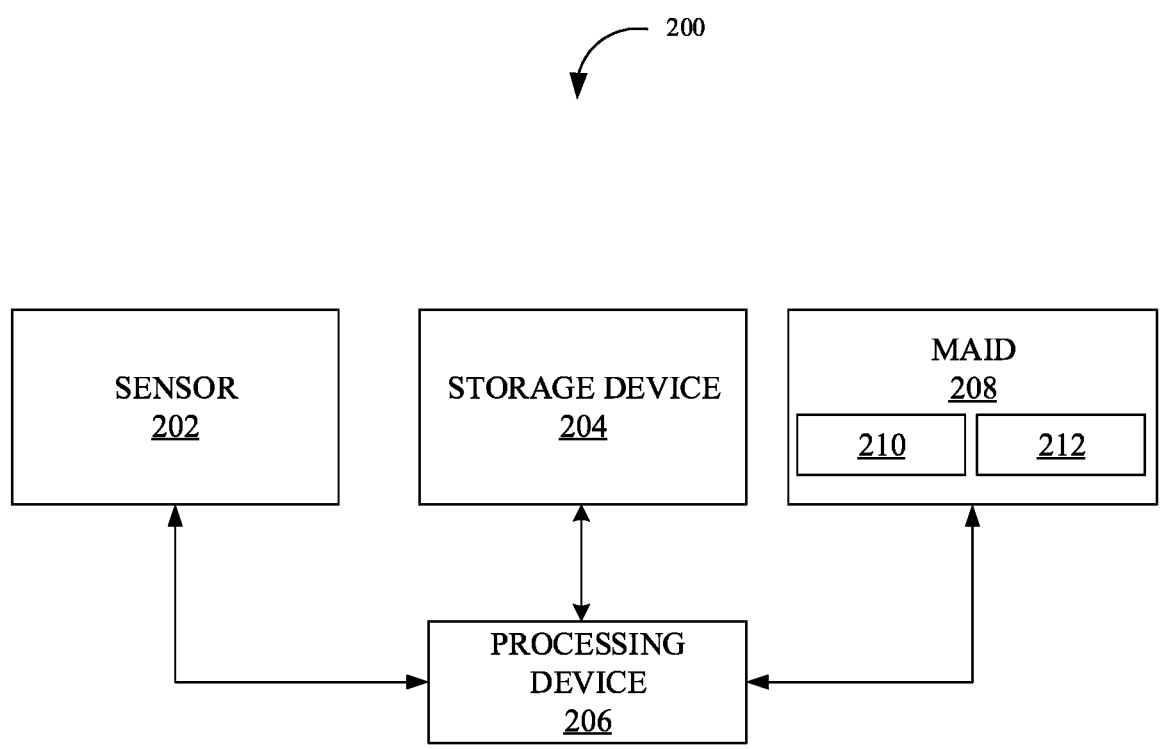
FIG. 2 is a block diagram of a system for facilitating administration of a pharmaceutical product, in accordance with some embodiments.

FIG. 2 is a block diagram of a system 200 for facilitating administration of a pharmaceutical product, in accordance with some embodiments. Accordingly, the system 200 may include at least one sensor 202, a storage device 204, a processing device 206, and a Mobile Administration Interlocking Device (MAID) 208.

Further, the at least one sensor 202 may be disposed on body of a user. Further, the at least one sensor 202 may be configured for generating at least one physiological data associated with the body.

Further, the storage device 204 may be configured for storing at least one dosage data. Further, the at least one dosage data may be prescribed by a medical professional. Further, the at least one dosage data may be associated with the user.

Further, the processing device 206 may be communicatively coupled with the at least one sensor 202. Further, the processing device 206 may be communicatively coupled with the storage device 204. Further, the processing device 206 may be configured for analyzing the at least one physiological data and the at least one dosage data. Further, the processing device 206 may be configured for determining a pharmaceutical dose of the pharmaceutical product corresponding to the user based on the analyzing. Further, the processing device 206 may be configured for generating a command based on the determining.

Further, the Mobile Administration Interlocking Device (MAID) 208 configured for provisioning the pharmaceutical product to the user. Further, the MAID 208 may be communicatively coupled with the processing device 206. Further, the MAID 208 may include a first chamber 210 and a first actuator 212. Further, the first chamber 210 may be configured for accommodating the pharmaceutical product. Further, the first chamber 210 may include a first opening. Further, the first opening facilitates dispensing of the pharmaceutical product. Further, the first actuator 212 may be communicatively coupled with the processing device 206. Further, the first actuator 212 may be operably coupled with the first chamber 210. Further, the first actuator 212 may be configured for dispensing the pharmaceutical product. Further, the first actuator 212 may be controlled by the processing device 206 based on the command. Further, the first actuator 212 may be configured to arrange in at least two states. Further, a first state of the at least two states facilitates dispensing of the pharmaceutical product. Further, a second state of the at least two states prevents access to the pharmaceutical product.

Figure 3:
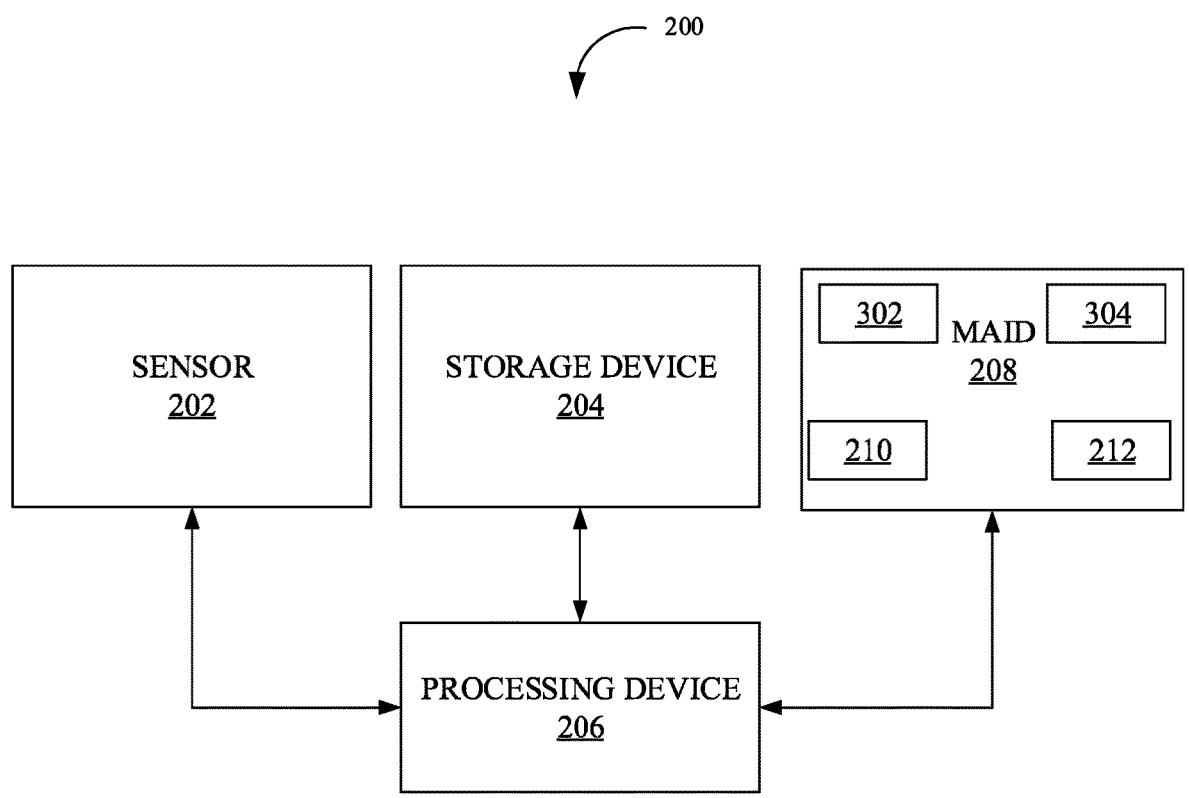
FIG. 3 is a block diagram of a system for facilitating administration of a pharmaceutical product, in accordance with some embodiments.

Further, in some embodiments, the MAID 208 may include a second chamber 302, as shown in FIG. 3, configured for accommodating an opioid antagonist. Further, the second chamber 302 may include a second sensor (not shown). Further, the second sensor may be configured for detecting an invalid dispensing action associated with the second chamber 302. Further, the second chamber 302 may include a second actuator 304, as shown in FIG. 3. Further, the second sensor may be coupled with the second actuator 304. Further, the second actuator 304 may be communicatively coupled with the processing device 206. Further, the second actuator 304 may be configured for controlling dispensing of the opioid antagonist based on the detection of the invalid dispensing action. Further, the dispensing of the opioid antagonist facilitates the neutralizing of the opioid. Further, in some embodiments, the processing device 206 may be configured to generate an alert based on the detection of the invalid dispensing action. Further, the system 200 further may include a communication device configured for transmitting the alert to at least one-second user device. Further, the at least one second user device may be associated with at least one second user.

Figure 4:
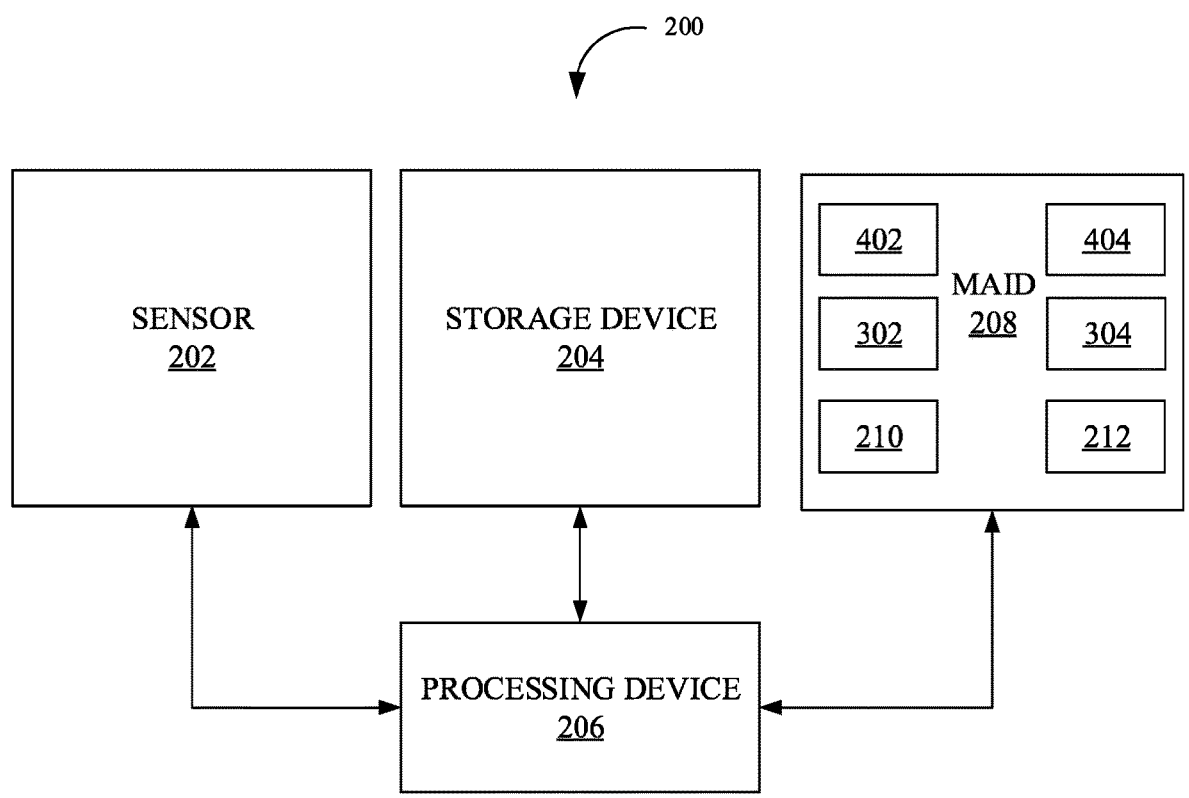
FIG. 4 is a block diagram of a system for facilitating administration of a pharmaceutical product, in accordance with some embodiments.

Further, in some embodiments, the MAID 208 further may include a third chamber 402, as shown in FIG. 4, configured for storing a deterrent compound and a hardening agent. Further, the third chamber 402 may be coupled with a third actuator 404, as shown in FIG. 4. Further, the third actuator 404 may be configured for mixing the deterrent compound and the hardening agent based on the detecting of the invalid dispensing action. Further, the third actuator 404 may be configured for dispensing the mixture into at least one of the first chamber 210 and the first actuator 212. Further, the hardening of the mixture prevents dispensing of the pharmaceutical product to the user.

Figure 5:
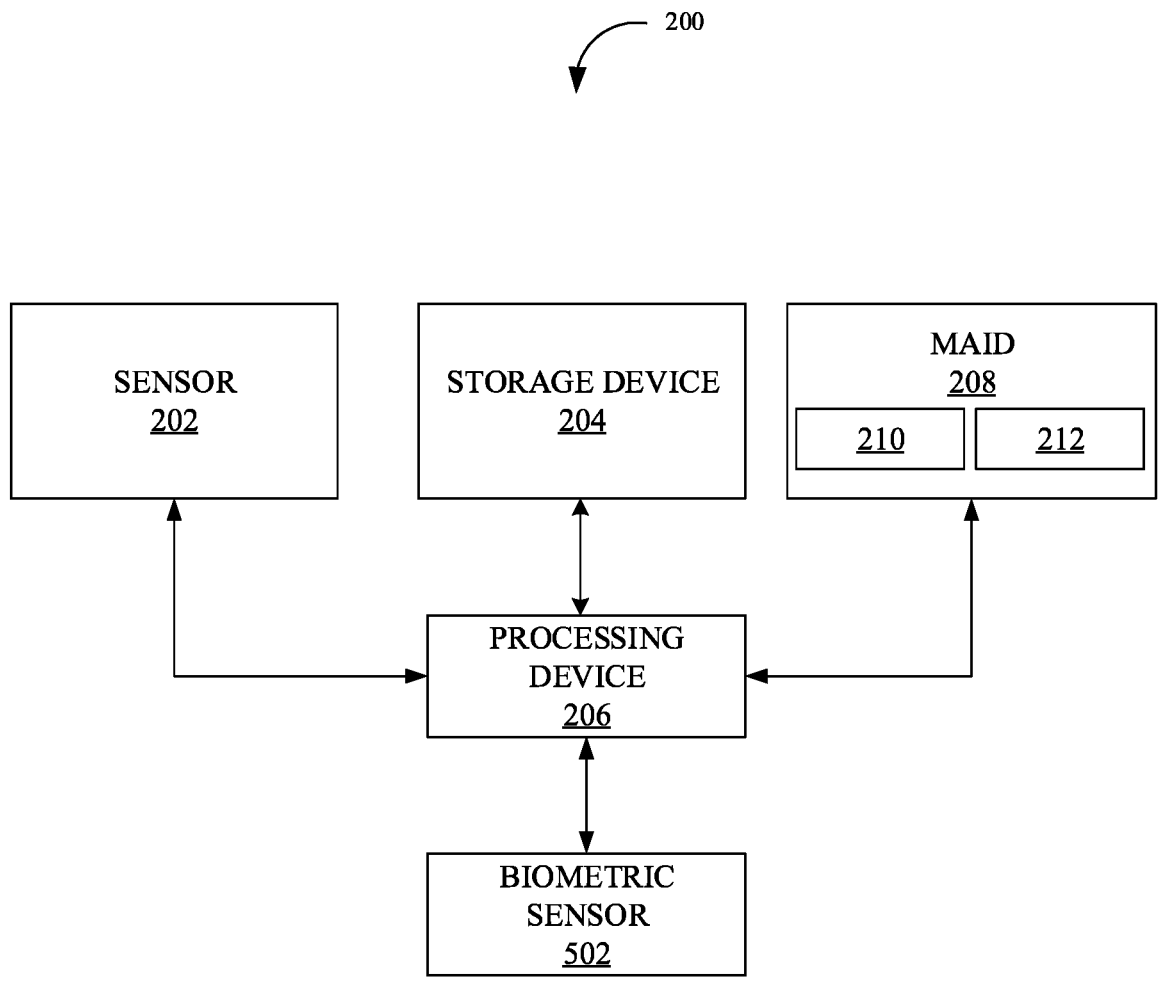
FIG. 5 is a block diagram of a system for facilitating administration of a pharmaceutical product, in accordance with some embodiments.

Further, in some embodiments, the system 200 further may include a biometric sensor 502, as shown in FIG. 5, configured for verifying the user. Further, the dispensing of the pharmaceutical product may be based on the verification of the user. Further, the biometric sensor 502 may be communicatively coupled with the processing device 206. Further, the biometric sensor 502 may be configured for generating a user biometric data. Further, the storage device 204 may be configured for retrieving a user data corresponding to the user. Further, the processing device 206 may be configured for analyzing the user biometric data and the user data to generate a notification. Further, the system 200 further may include a communication device configured for transmitting the notification to at least one of user device and the at least one second user device.

Further, in some embodiments, the first actuator 212 may be coupled with a dispensing sensor (not shown). Further, the dispensing sensor may be configured to detect dispensing of the pharmaceutical product. Further, the dispensing sensor may be configured to generate a dispensing data. Further, the processing device 206 may be configured for analyzing the dispensing data to generate an alert. Further, the system 200 further may include a communication device (not shown) configured for transmitting the alert to the at least one second user device.

Further, in some embodiments, the storage device 204 may be configured for storing at least one of the at least one physiological data and the dispensing data. Further, the processing device 206 may be configured for analyzing at least one of the at least one dosage data, the at least one physiological data, and the dispensing data to generate a notification. Further, the system 200 further may include a communication device (not shown) configured for transmitting the notification to at least one of the user device and the at least one second user device.

FIG. 3 is a block diagram of a system 200 for facilitating administration of a pharmaceutical product, in accordance with some embodiments.

FIG. 4 is a block diagram of a system 200 for facilitating administration of a pharmaceutical product, in accordance with some embodiments.

FIG. 5 is a block diagram of a system 200 for facilitating administration of a pharmaceutical product, in accordance with some embodiments.

Figure 6:
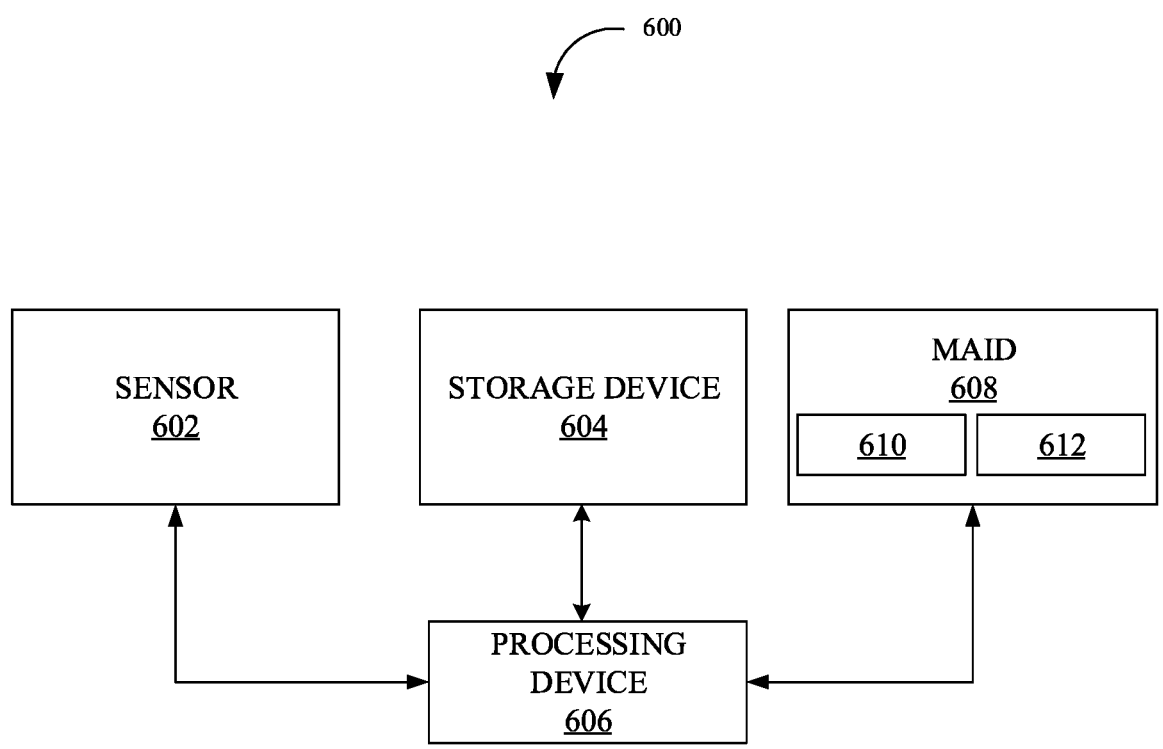
FIG. 6 is a block diagram of a system for facilitating administration of an opioid, in accordance with some embodiments.

FIG. 6 is a block diagram of a system 600 for facilitating administration of an opioid, in accordance with some embodiments. Accordingly, the system 600 may include at least one sensor 602, a storage device 604, a processing device 606, and a Mobile Administration Interlocking Device (MAID) 608.

Further, the at least one sensor 602 may be disposed on the body of a user. Further, the at least one sensor 602 may be configured for generating at least one physiological data associated with the body.

Further, the storage device 604 may be configured for storing at least one dosage data. Further, the at least one dosage data may be prescribed by a medical professional. Further, the at least one dosage data may be associated with the user.

Further, the processing device 606 may be communicatively coupled with the at least one sensor 602. Further, the processing device 606 may be communicatively coupled with the storage device 604. Further, the processing device 606 may be configured for analyzing the at least one physiological data and the at least one dosage data. Further, the processing device 606 may be configured for determining a pharmaceutical dose of the opioid corresponding to the user based on the analyzing. Further, the processing device 606 may be configured for generating a command based on the determining.

Further, the Mobile Administration Interlocking Device (MAID) 608 may be configured for provisioning the opioid to the user. Further, the MAID 608 may be communicatively coupled with the processing device 606. Further, the MAID 608 may include a first chamber 610 and a first actuator 612.

Further, the first chamber 610 configured for accommodating the opioid. Further, the first chamber 610 may include a first opening. Further, the first opening facilitates dispensing of the opioid. Further, the first actuator 612 may be communicatively coupled with the processing device 606. Further, the first actuator 612 may be operably coupled with the first chamber 610. Further, the first actuator 612 may be configured for dispensing the opioid. Further, the first actuator 612 may be controlled by the processing device 606 based on the command. Further, the first actuator 612 may be configured to arrange in at least two states. Further, a first state of the at least two states facilitates dispensing of the opioid. Further, a second state of the at least two states prevents access to the opioid.

Figure 7:
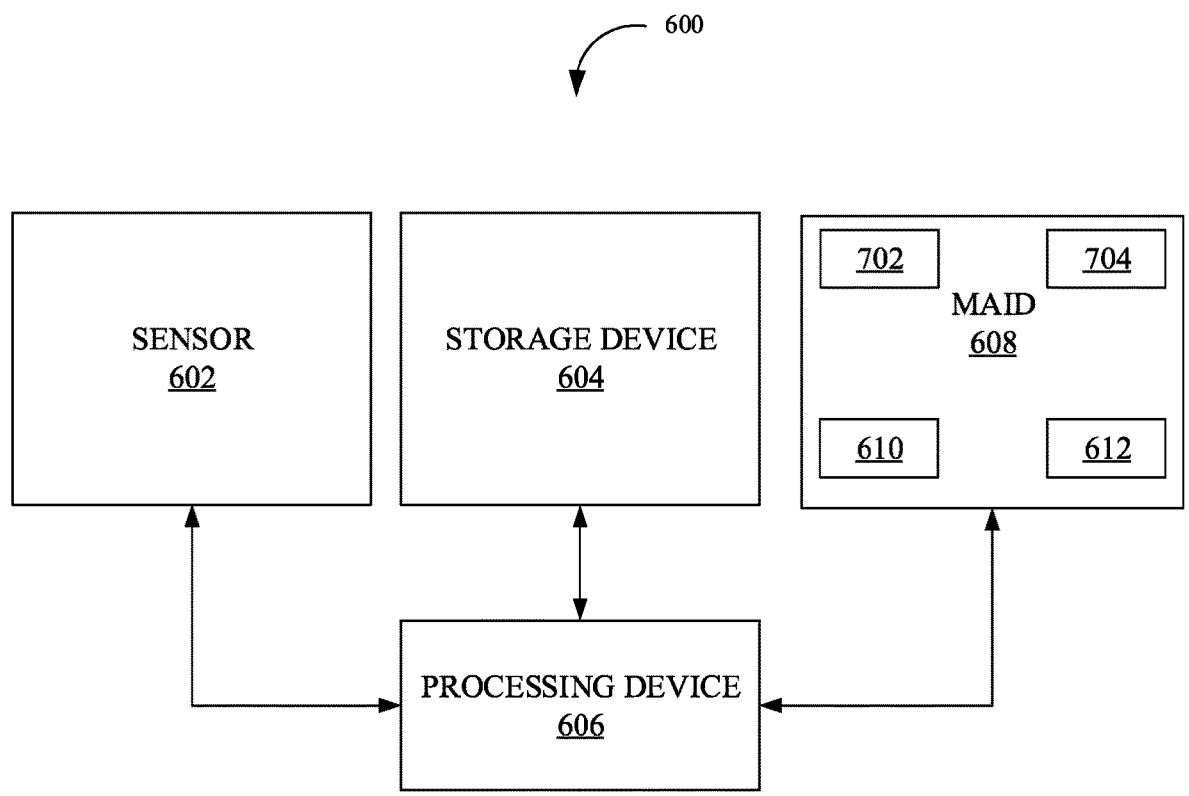
FIG. 7 is a block diagram of a system for facilitating administration of an opioid, in accordance with some embodiments.

Further, in some embodiments, the MAID 608 may include a second chamber 702, as shown in FIG. 7, configured for accommodating an opioid antagonist. Further, the second chamber 702 may include a second sensor. Further, the second sensor may be configured for detecting an invalid dispensing action associated with the second chamber 702. Further, the second chamber 702 may include a second actuator 704, as shown in FIG. 7. Further, the second sensor may be coupled with the second actuator 704. Further, the second actuator 704 may be communicatively coupled with the processing device 606. Further, the second actuator 704 may be configured for controlling dispensing of the opioid antagonist based on the detection of the invalid dispensing action. Further, the dispensing of the opioid antagonist facilitates the neutralizing of the opioid. Further, in some embodiments, the processing device 606 may be configured to generate an alert based on the detection of the invalid dispensing action. Further, the system 600 further may include a communication device configured for transmitting the alert to at least one-second user device. Further, the at least one second user device may be associated with at least one second user.

Figure 8:
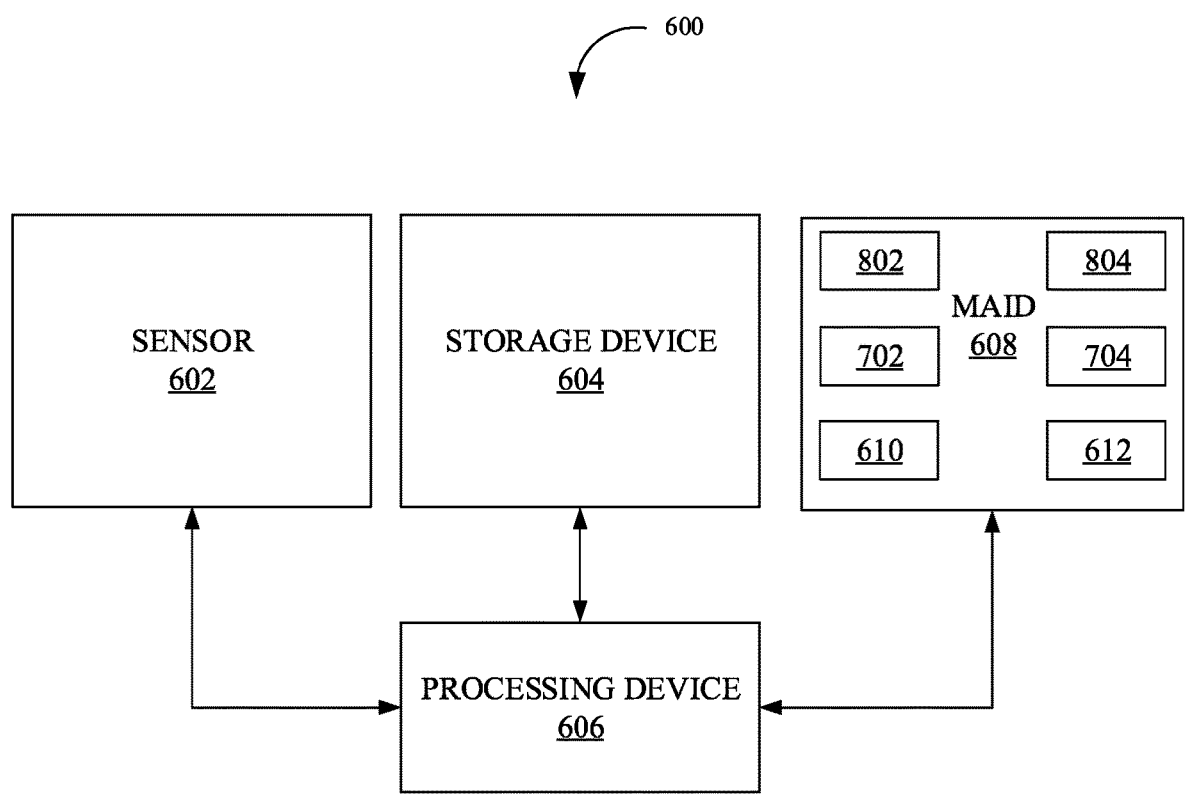
FIG. 8 is a block diagram of a system for facilitating administration of an opioid, in accordance with some embodiments.

Further, in some embodiments, the MAID 608 further may include a third chamber 802, as shown in FIG. 8, configured for storing a deterrent compound and a hardening agent. Further, the third chamber 802 may be coupled with a third actuator 804, as shown in FIG. 8. Further, the third actuator 804 may be configured for mixing the deterrent compound and the hardening agent based on the detecting of the invalid dispensing action. Further, the third actuator 804 may be configured for dispensing the mixture into at least one of the first chamber 610 and the first actuator 612. Further, the hardening of the mixture prevents dispensing of the pharmaceutical product to the user.

Figure 9:
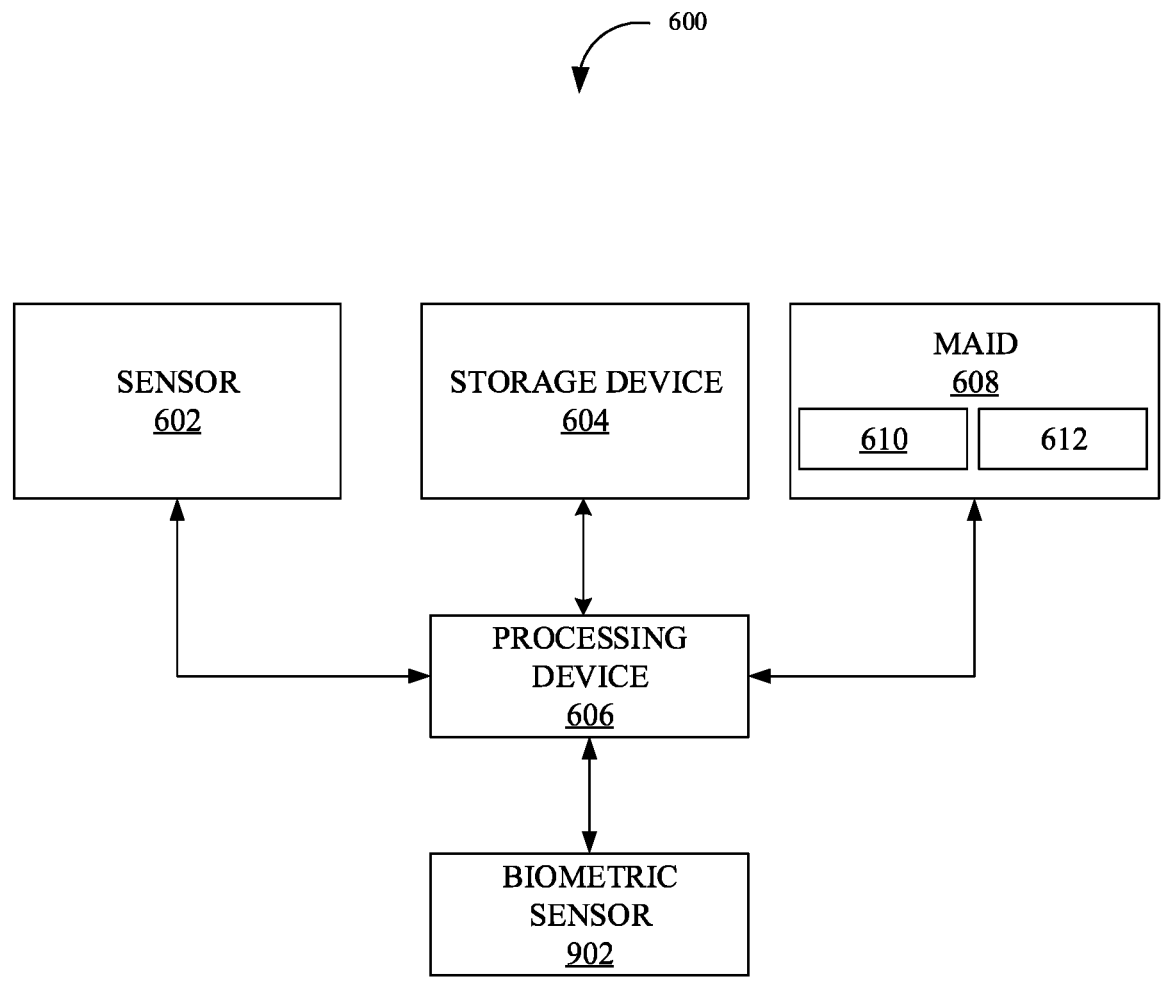
FIG. 9 is a block diagram of a system for facilitating administration of an opioid, in accordance with some embodiments.

Further, in some embodiments, the system 600 further may include a biometric sensor 902, as shown in FIG. 9, configured for verifying the user. Further, the dispensing of the opioid may be based on the verification of the user. Further, the biometric sensor 902 may be communicatively coupled with the processing device 606. Further, the biometric sensor 902 may be configured for generating a user biometric data. Further, the storage device 604 may be configured for retrieving a user data corresponding to the user. Further, the processing device 606 may be configured for analyzing the user biometric data and the user data to generate a notification. Further, the system 600 further may include a communication device configured for transmitting the notification to at least one of user device and the at least one second user device.

Further, in some embodiments, the first actuator 612 may be coupled with a dispensing sensor (not shown). Further, the dispensing sensor may be configured to detect dispensing of the opioid. Further, the dispensing sensor may be configured to generate a dispensing data. Further, the processing device 606 may be configured for analyzing the dispensing data to generate an alert. Further, the system 600 further may include a communication device (not shown) configured for transmitting the alert to the at least one second user device.

Further, in some embodiments, the storage device 604 may be configured for storing at least one of the at least one physiological data and the dispensing data. Further, the processing device 606 may be configured for analyzing at least one of the at least one dosage data, the at least one physiological data, and the dispensing data to generate a notification. Further, the system 600 further may include a communication device (not shown) configured for transmitting the notification to at least one of the user device and the at least one second user device.

FIG. 7 is a block diagram of a system 600 for facilitating administration of an opioid, in accordance with some embodiments.

FIG. 8 is a block diagram of a system 600 for facilitating administration of an opioid, in accordance with some embodiments.

FIG. 9 is a block diagram of a system 600 for facilitating administration of an opioid, in accordance with some embodiments.

Figure 10:
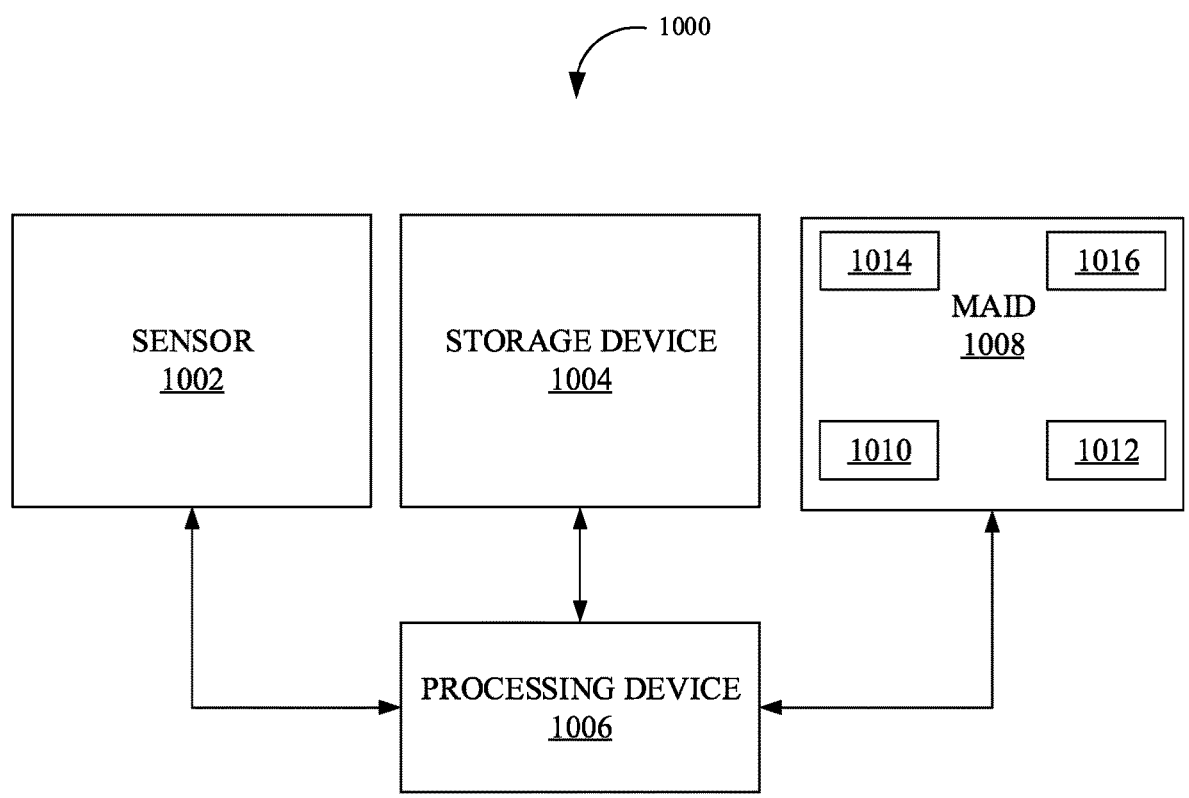
FIG. 10 is a block diagram of a system for facilitating administration of an opioid, in accordance with some embodiments.

FIG. 10 is a block diagram of a system 1000 for facilitating administration of an opioid, in accordance with some embodiments. Accordingly, the system 1000 may include at least one sensor 1002, a storage device 1004, a processing device 1006, and a Mobile Administration Interlocking Device (MAID) 1008.

Further, the at least one sensor 1002 may be disposed on the body of a user. Further, the at least one sensor 1002 may be configured for generating at least one physiological data associated with the body.

Further, the storage device 1004 may be configured for storing at least one dosage data. Further, the at least one dosage data may be prescribed by a medical professional. Further, the at least one dosage data may be associated with the user.

Further, the processing device 1006 may be communicatively coupled with the at least one sensor 1002. Further, the processing device 1006 may be communicatively coupled with the storage device 1004. Further, the processing device 1006 may be configured for analyzing the at least one physiological data and the at least one dosage data. Further, the processing device 1006 may be configured for determining a pharmaceutical dose of the opioid corresponding to the user based on the analyzing. Further, the processing device 1006 may be configured for generating a command based on the determining.

Further, the Mobile Administration Interlocking Device (MAID) 1008 may be configured for provisioning the opioid to the user. Further, the MAID 1008 may be communicatively coupled with the processing device 1006. Further, the MAID 1008 may include a first chamber 1010, a first actuator 1012, and a second chamber 1014. Further, the first chamber 1010 may be configured for accommodating the opioid. Further, the first chamber 1010 may include a first opening. Further, the first opening facilitates dispensing of the opioid. Further, the first actuator 1012 may be communicatively coupled with the processing device 1006. Further, the first actuator 1012 may be operably coupled with the first chamber 1010. Further, the first actuator 1012 may be configured for dispensing the opioid. Further, the first actuator 1012 may be controlled by the processing device 1006 based on the command. Further, the first actuator 1012 may be configured to arrange in at least two states. Further, a first state of the at least two states facilitates dispensing of the opioid. Further, a second state of the at least two states prevents access to the opioid. Further, the second chamber 1014 may be configured for accommodating an opioid antagonist.

Further, the second chamber 1014 may include a second sensor. Further, the second sensor may be configured for detecting an invalid dispensing action associated with the second chamber 1014. Further, the second chamber 1014 may include a second actuator 1016. Further, the second sensor may be coupled with the second actuator 1016. Further, the second actuator 1016 may be communicatively coupled with the processing device 1006. Further, the second actuator 1016 may be configured for controlling dispensing of the opioid antagonist based on the detection of the invalid dispensing action. Further, the dispensing of the opioid antagonist facilitates the neutralizing of the opioid.

Further, in some embodiments, the processing device 1006 may be configured to generate an alert based on the detection of the invalid dispensing action. Further, the system 1000 further may include a communication device (not shown) configured for transmitting the alert to at least one second user device. Further, the at least one second user device may be associated with at least one second user.

Figure 11:
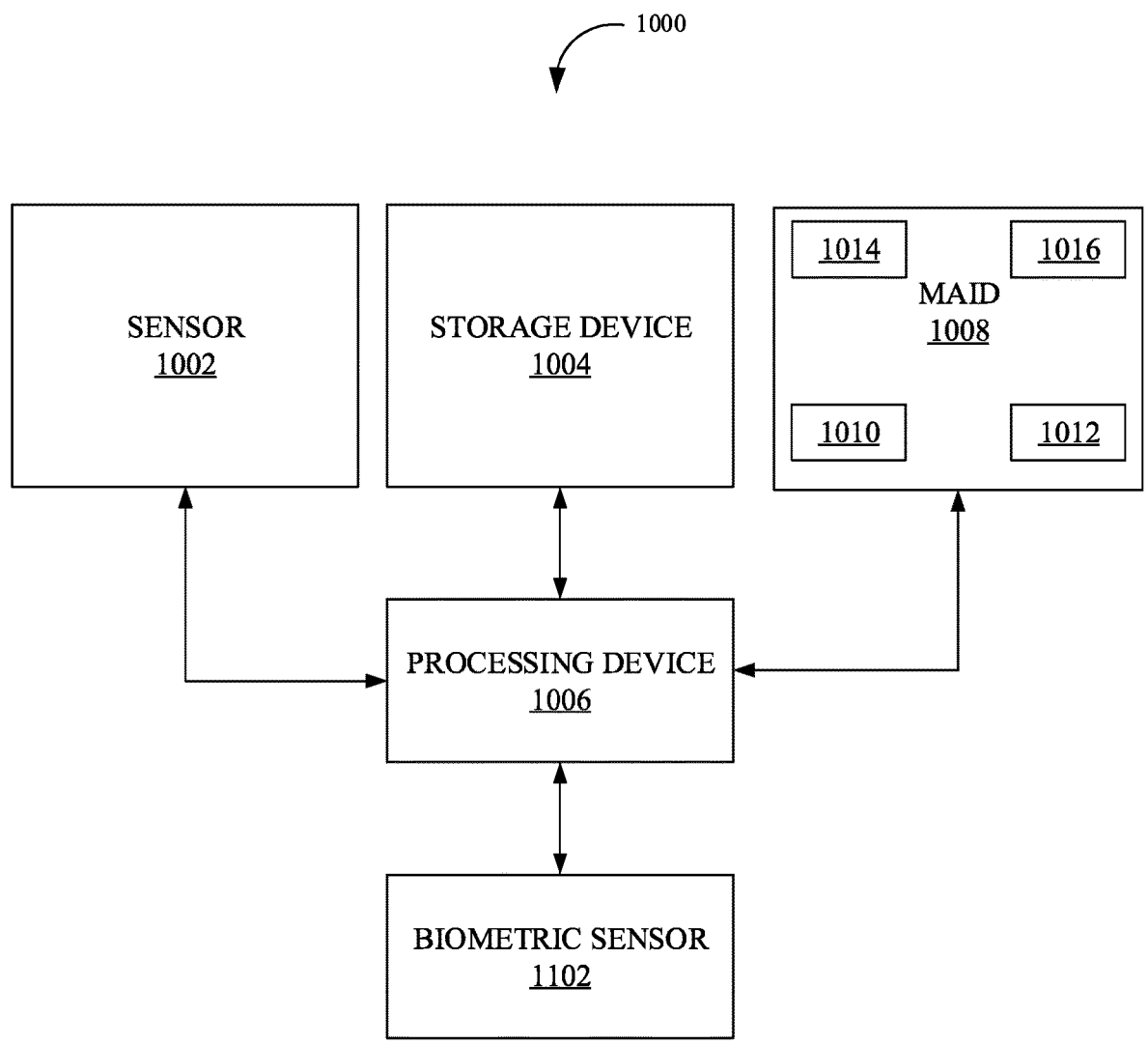
FIG. 11 is a block diagram of a system for facilitating administration of an opioid, in accordance with some embodiments.

Further, in some embodiments, the system 1000 further may include a biometric sensor 1102, as shown in FIG. 11, configured for verifying the user. Further, the dispensing of the opioid may be based on the verification of the user. Further, the biometric sensor 1102 may be communicatively coupled with the processing device 1006. Further, the biometric sensor 1102 may be configured for generating a user biometric data. Further, the storage device 1004 may be configured for retrieving a user data corresponding to the user. Further, the processing device 1006 may be configured for analyzing the user biometric data and the user data to generate a notification. Further, the system 1000 further may include a communication device (not shown) configured for transmitting the notification to at least one of user device and the at least one second user device.

Further, in some embodiments, the first actuator 1012 may be coupled with a dispensing sensor. Further, the dispensing sensor may be configured to detect dispensing of the opioid. Further, the dispensing sensor may be configured to generate a dispensing data. Further, the processing device 1006 may be configured for analyzing the dispensing data to generate an alert. Further, the system 1000 further may include a communication device (not shown) configured for transmitting the alert to the at least one second user device.

Further, in some embodiments, the storage device 1004 may be configured for storing at least one of the at least one physiological data and the dispensing data. Further, the processing device 1006 may be configured for analyzing at least one of the at least one dosage data, the at least one physiological data, and the dispensing data to generate a notification. Further, the system 1000 further may include a communication device (not shown) configured for transmitting the notification to at least one of the user device and the at least one second user device.

Figure 12:
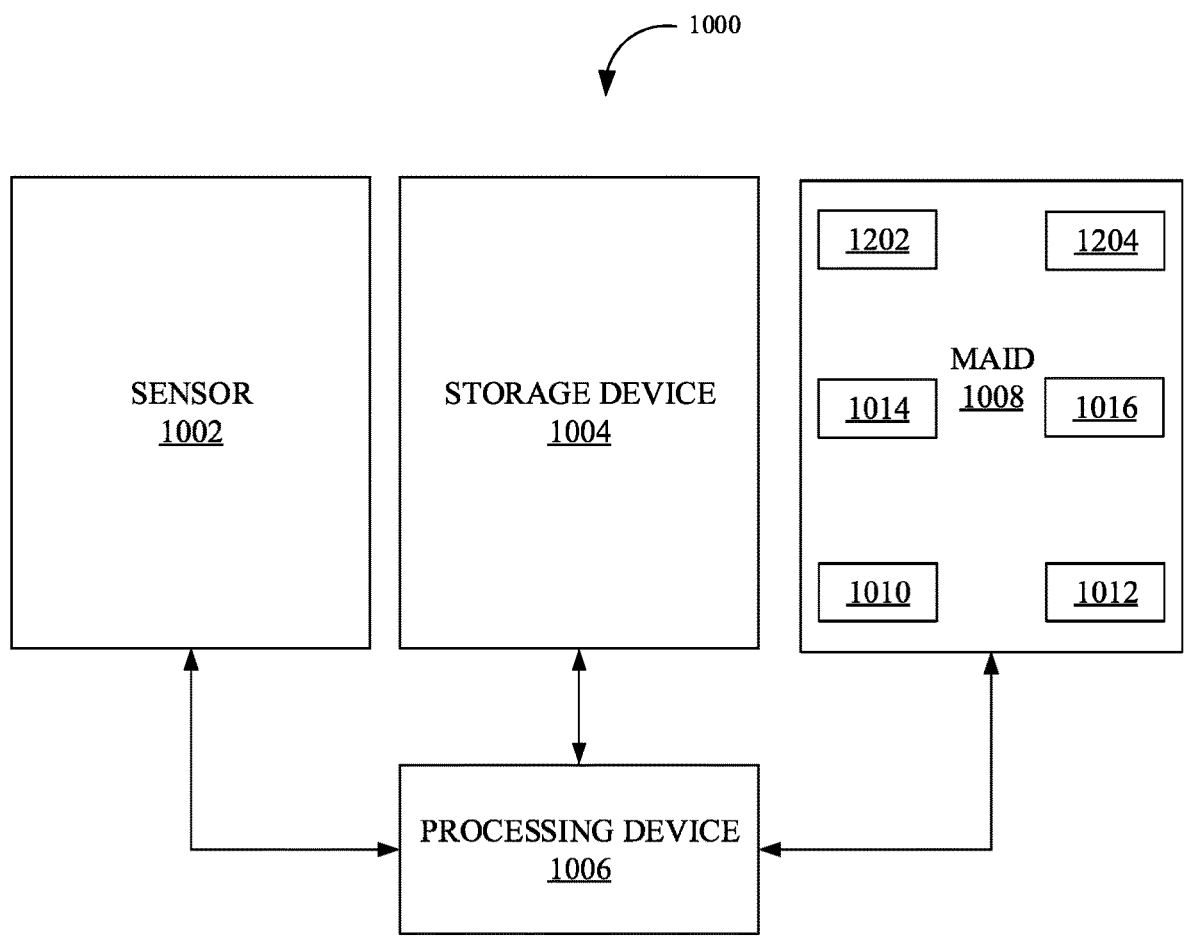
FIG. 12 is a block diagram of a system for facilitating administration of an opioid, in accordance with some embodiments.

Further, in some embodiments, the MAID 1008 further may include a third chamber 1202, as shown in FIG. 12, configured for storing a deterrent compound and a hardening agent. Further, the third chamber 1202 may be coupled with a third actuator 1204, as shown in FIG. 12. Further, the third actuator 1204 may be configured for mixing the deterrent compound and the hardening agent based on the detecting of the invalid dispensing action. Further, the third actuator 1204 may be configured for dispensing the mixture into at least one of the first chamber 1010 and the first actuator 1012. Further, the hardening of the mixture prevents dispensing of the pharmaceutical product to the user.

FIG. 11 is a block diagram of a system 1000 for facilitating administration of an opioid, in accordance with some embodiments.

FIG. 12 is a block diagram of a system 1000 for facilitating administration of an opioid, in accordance with some embodiments.

Figure 13:
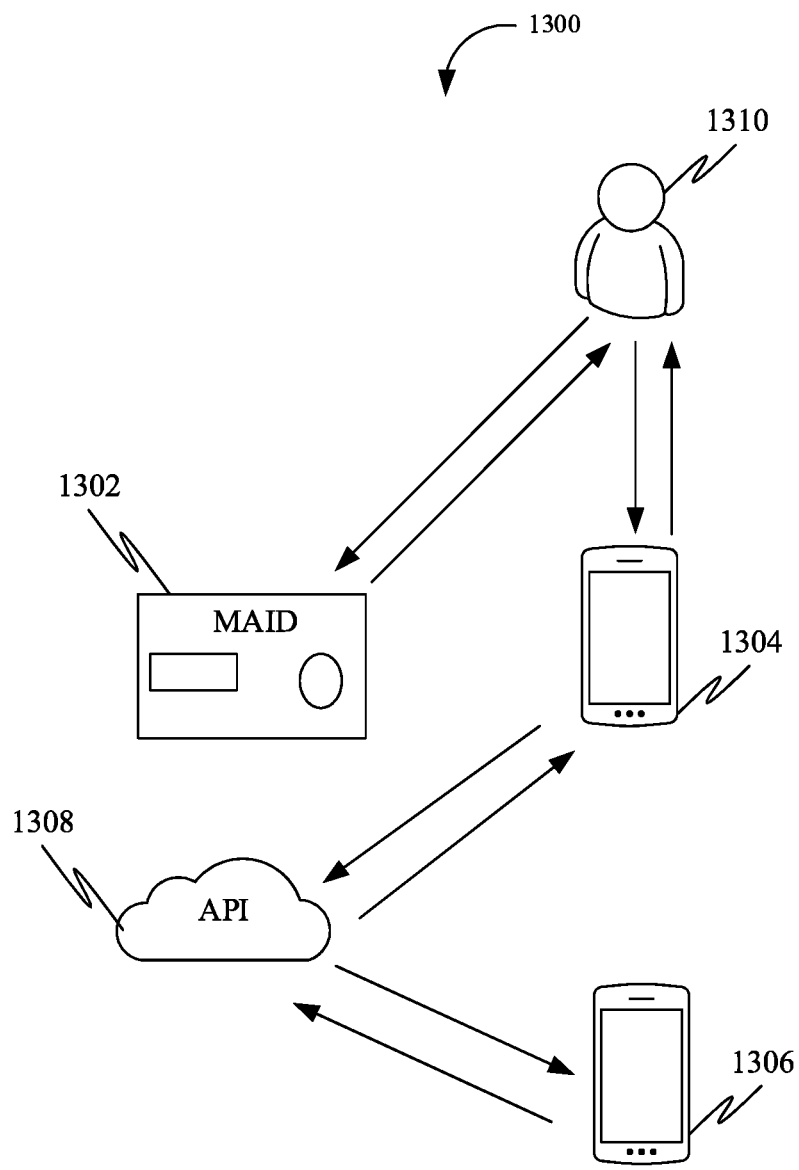
FIG. 13 is a schematic of a system for facilitating administration of a pharmaceutical product, in accordance with some embodiments.

FIG. 13 is a schematic of a system 1300 for facilitating administration of a pharmaceutical product, in accordance with some embodiments. Accordingly, the system 1300 may include a MAID 1302. a user Mobile Integrated Computer Device (MICD) 1304, a third party MICD 1306, and an API interface 1308. Further, a user may take a prescribed dosage of a medication 1310.

Figure 14:
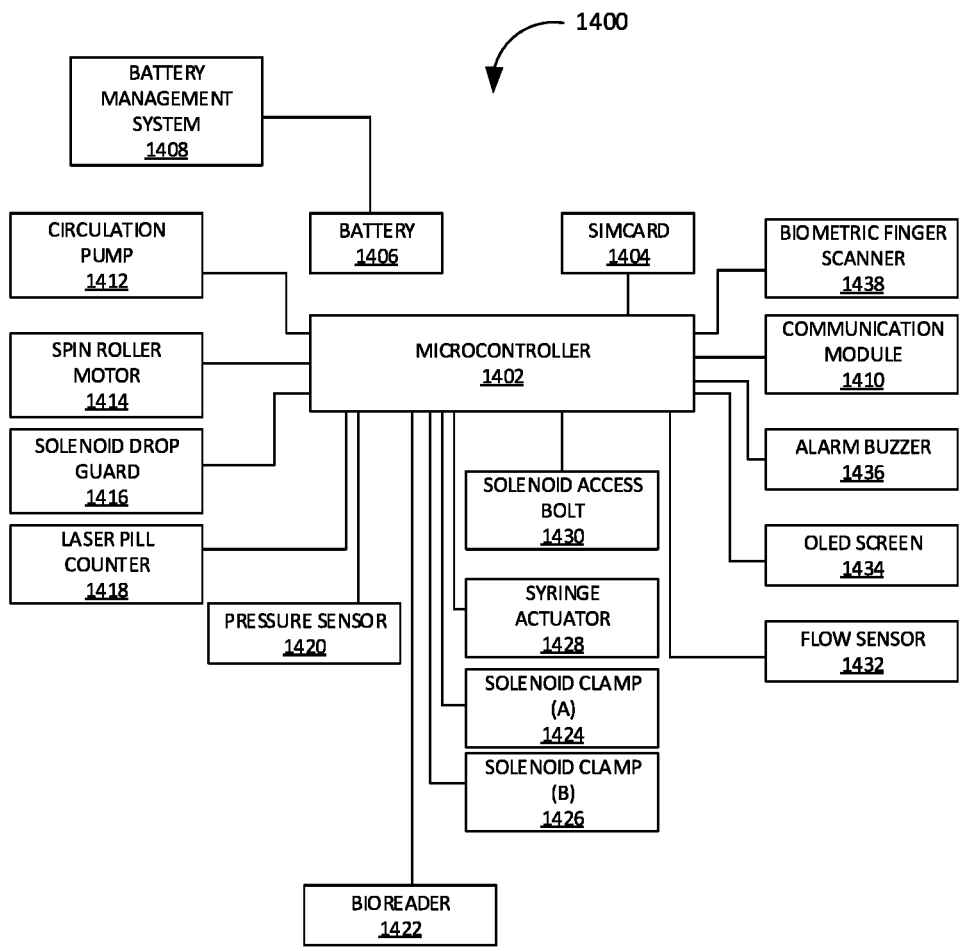
FIG. 14 is an electrical block diagram of a system of a Mobile Administration-Interlocking Device (MAID), in accordance with some embodiments.

FIG. 14 is an electrical block diagram of a system 1400 of a Mobile Administration-Interlocking Device (MAID), in accordance with some embodiments. Further, the system 1400 may include a microcontroller 1402. Further, the microcontroller 1402 may have a sim card slot 1404, a battery bank 1406, a battery management system 1408, and a communication module 1410. Further, the microcontroller 1402 may manage the functionality of a circulation pump 1412, a spin roller motor 1414, a solenoid drop guard 1416, a laser solid medication counter 1418, a housing pressure sensor(s) 1420, a biological cartridge reader 1422, a solenoid clamp A 1424, a solenoid clamp B 1426, a syringe actuator 1428, a solenoid access bolt lock 1430, a liquid medication flow sensor 1432, an OLED screen module 1434, a high pitch alarm buzzer 1436, and a biometric finger scanner 1438.

Figure 15:
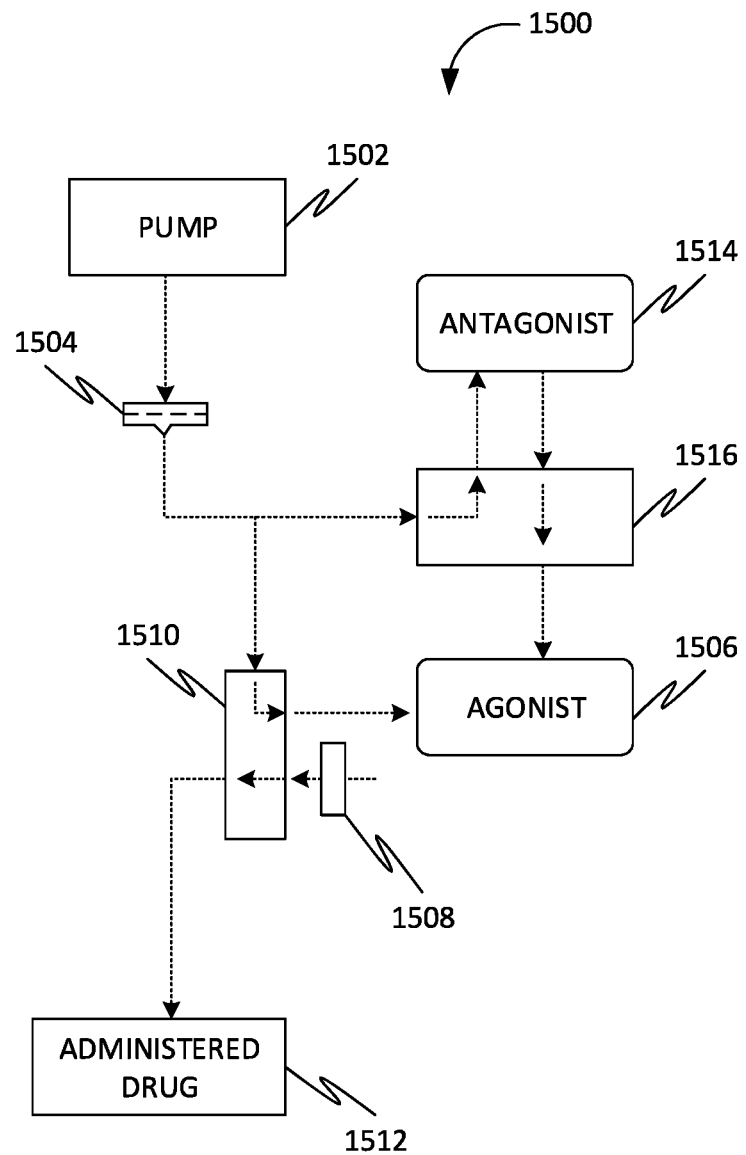
FIG. 15 is a block diagram of a Liquid Medication Administration Assembly, in accordance with some embodiments.

FIG. 15 is a block diagram of a Liquid Medication Administration Assembly 1500, in accordance with some embodiments. Further, the Liquid Medication Administration Assembly 1500 may utilize a circulation pump 1502, and a micro-filter to purify the expelled air 1504. An agonist reservoir 1506, which may house an opioid, and may be connected to a flow sensor 1508, and a solenoid clamp B 1510. When initiated, the agonist 1506 may be administered 1512 to a separate holding vessel. The antagonist reservoir 1514 may house an agent that reverses the pharmaceutical effects of the agonist 1506. An antagonist reservoir 1514 may be connected to a solenoid clamp A 1516.

Figure 16:
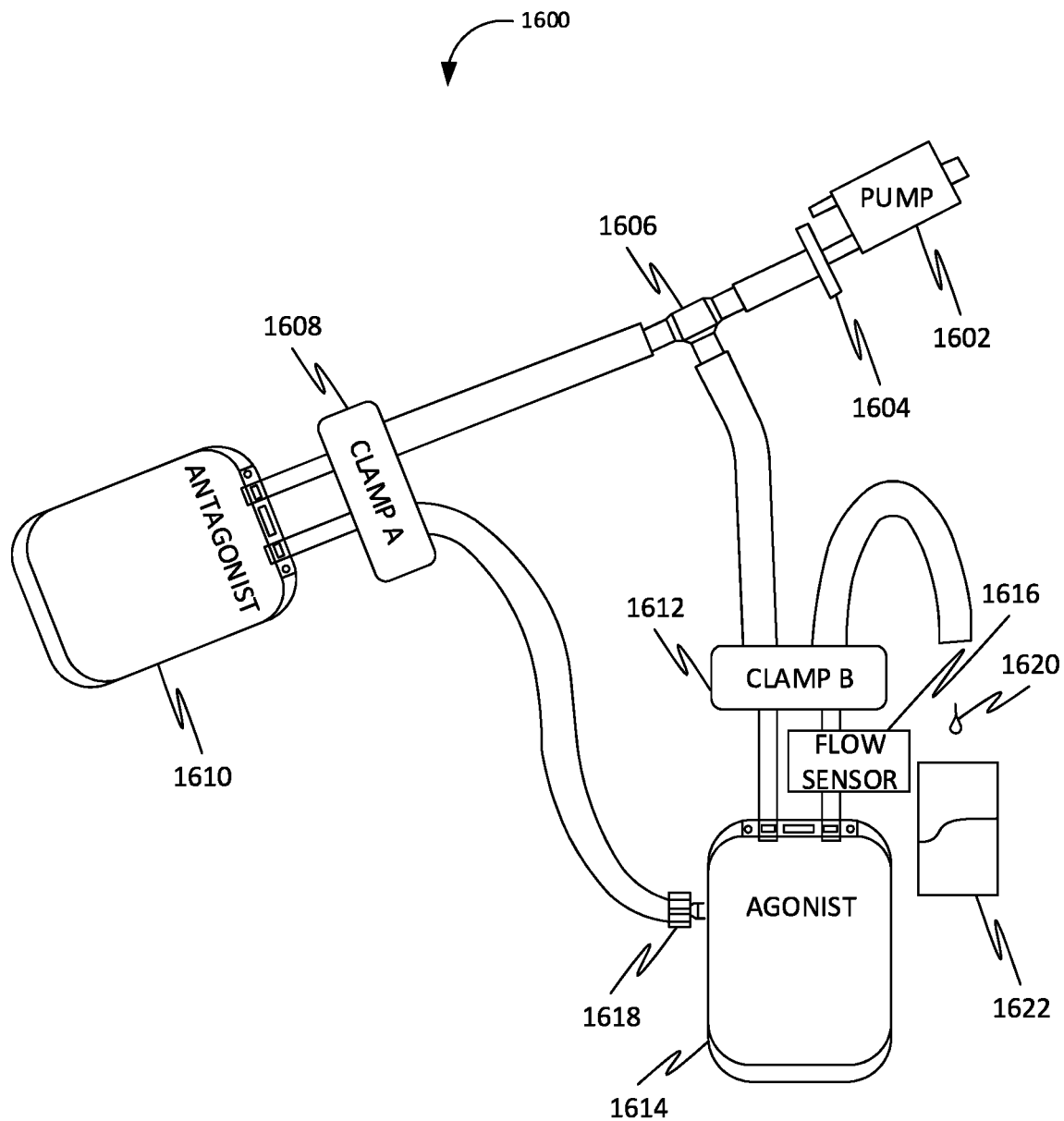
FIG. 16 is an illustration of a Liquid Medication Administration Assembly, in accordance with some embodiments.

FIG. 16 is an illustration of a Liquid Medication Administration Assembly 1600, in accordance with some embodiments. Accordingly, the Liquid Medication Administration Assembly 1600 may incorporate a pump 1602, air filter 1604, a tubing T connector 1606, solenoid clamp A 1608 for an antagonist reservoir 1610, and a solenoid clamp B 1612 for an agonist reservoir 1614, a flow sensor 1616, and a bag coupler connector 1618 to direct the flow of expelled antagonist into the agonist reservoir. An expelled liquid ding 1620 may be deposited in a liquid dispense cup 1622.

Figure 17:
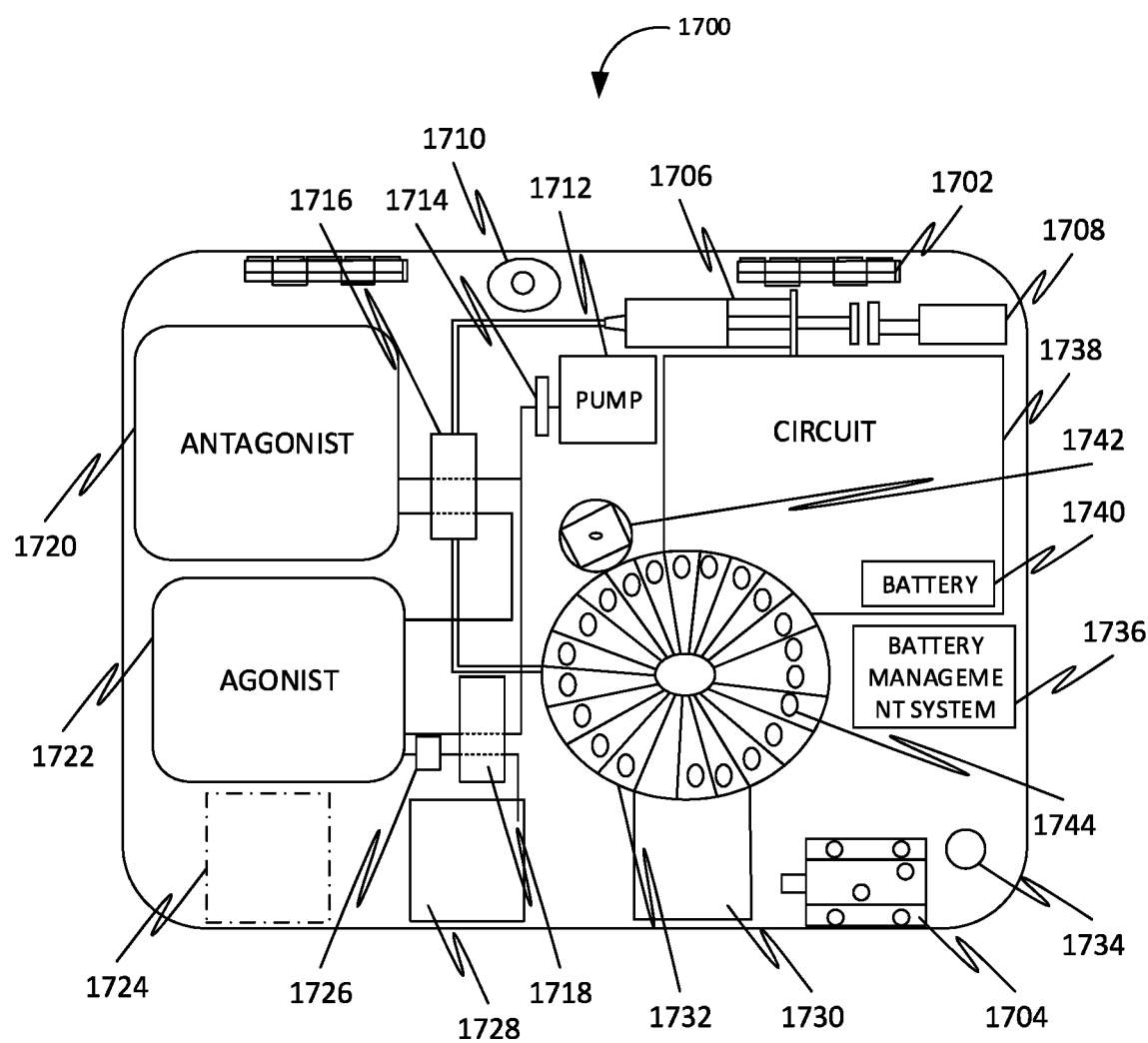
FIG. 17 is a cross-sectional view of a Mobile Administration-Interlocking Device (MAID), in accordance with some embodiments.

FIG. 17 is a cross-sectional view of a Mobile Administration-Interlocking Device (MAID) 1700, in accordance with some embodiments. Further, the MAID 1700 may include hinges 1702, and a solenoid access bolt 1704. Further, the MAID 1700 may also house a syringe 1706, a syringe actuator 1708, an alarm buzzer 1710, a circulation pump 1712, an air filter 1714, a solenoid clamp A 1716 and a solenoid clamp B 1718, an antagonist reservoir 1720, an agonist reservoir 1722, a biological assay reader 1724 for sample cartridges, a flow sensor for the agonist 1726, a liquid dispense cup 1728, a solid dispense cup 1730, a solid medication administration disk 1732, a security docking sensor 1734, a battery management system 1736, a circuit 1738 and a battery 1740, and a spin roller 1742. Solid medications 1744 are placed into the solid medication administration disk 1732.

Figure 18:
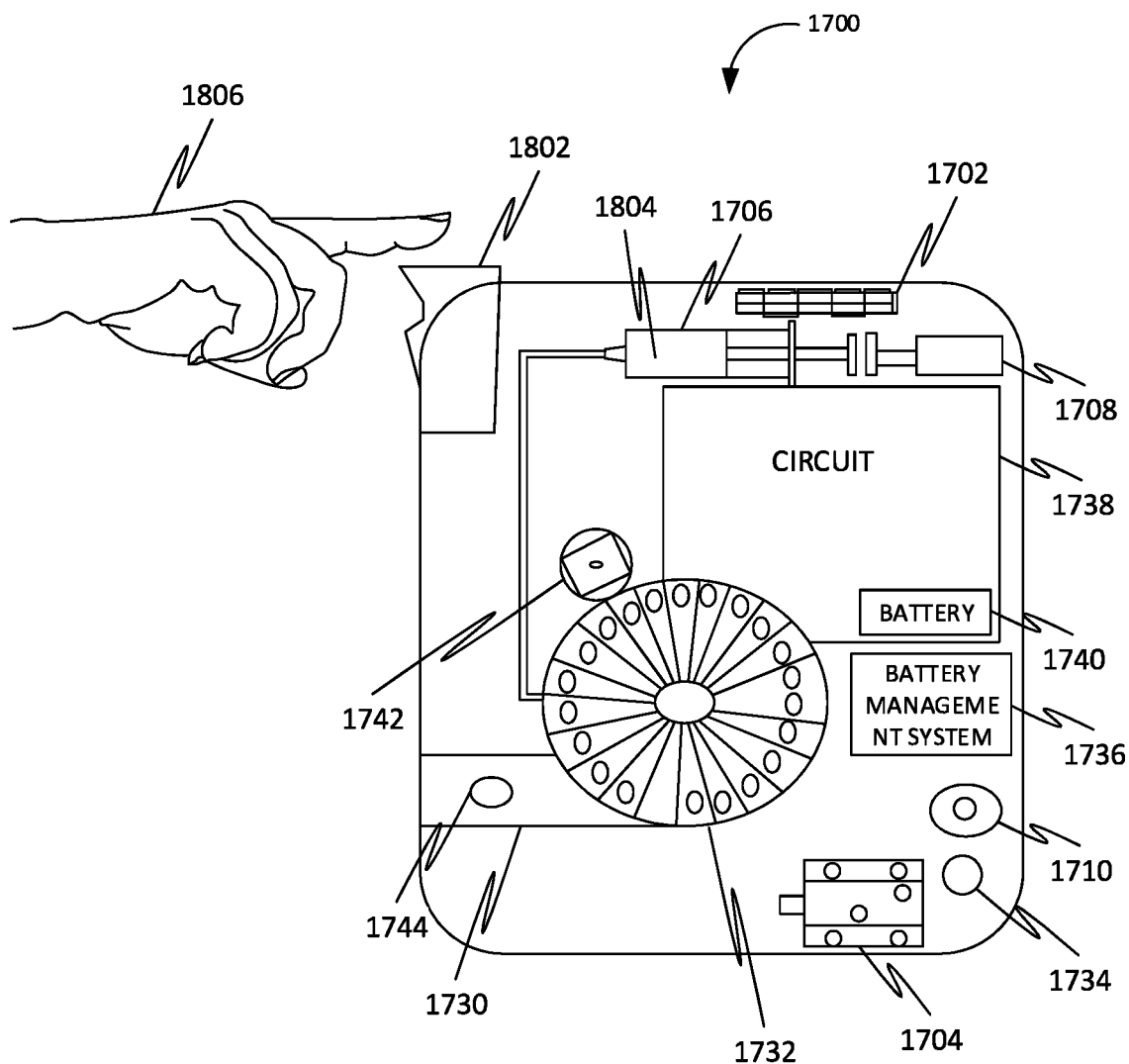
FIG. 18 is a cross-sectional view of a Mobile Administration-Interlocking Device (MAID) with a standalone Solid medication administration, in accordance with some embodiments.
Figure 19:
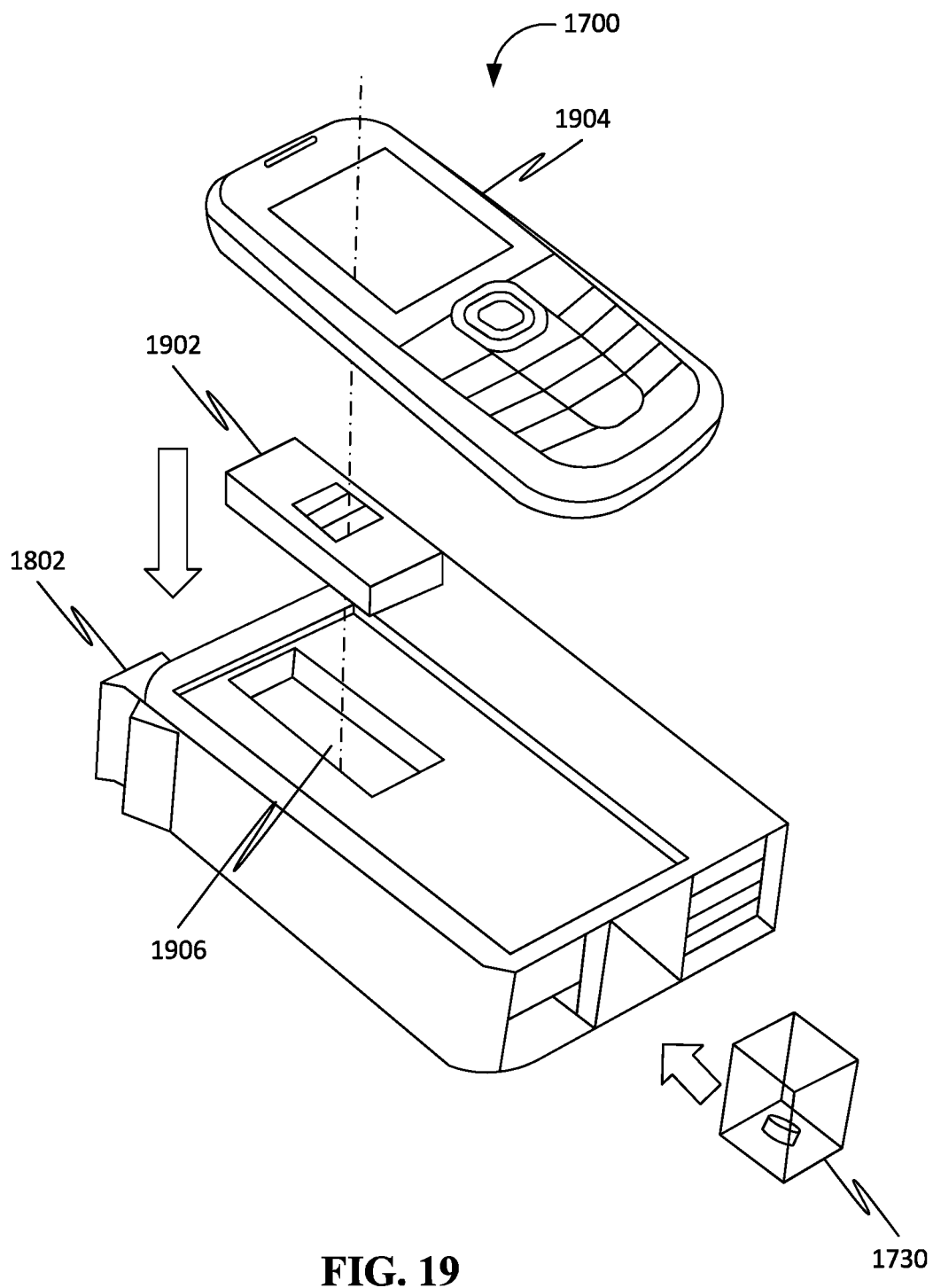
FIG. 19 is a perspective view of a Mobile Administration-Interlocking Device (MAID) with a standalone solid medication administration, in accordance with some embodiments.

FIG. 18 is a cross-sectional view of a Mobile Administration-Interlocking Device (MAID) 1700 with a standalone Solid medication administration, in accordance with some embodiments. Further, the MAID 1700 may include a biometric finger scanner 1802, a syringe with a deterrent solution 1804, the syringe actuator 1708, the circuit 1738 (such as an integrated microcontroller) with the battery 1740 and the battery management system 1736. Further, the MAID 1700 also has the alarm buzzer 1710, the security-docking sensor 1734, the hinge 1702, and the solenoid access bolt 1704. The solid medication 1744 is held in the solid medication administration disk 1732 and is deposited to the solid dispense cup 1730. The spin roller 1742 rotates the solid medication administration disk 1732. Prior to administering a solid medication dosage, a user would authenticate their identity by scanning their finger 1806 on a biometric finger scanner 1802. In addition, the MAID 1700 has mobile phone docking which allows the user to scan a biological cartridge 1902, as shown in FIG. 19, by loading it into the cartridge-docking bay 1906 and eclipsing a mobile phone 1904, as shown in FIG. 19, over the biological cartridge 1902 in the provided slot area. Further, the mobile phone 1904 may utilize an app to conduct a quantitative analysis of an assay cartridge (such as the biological cartridge 1902).

FIG. 19 is a perspective view of a Mobile Administration-Interlocking Device (MAID) 1700 with a standalone solid medication administration, in accordance with some embodiments.

Figure 20:
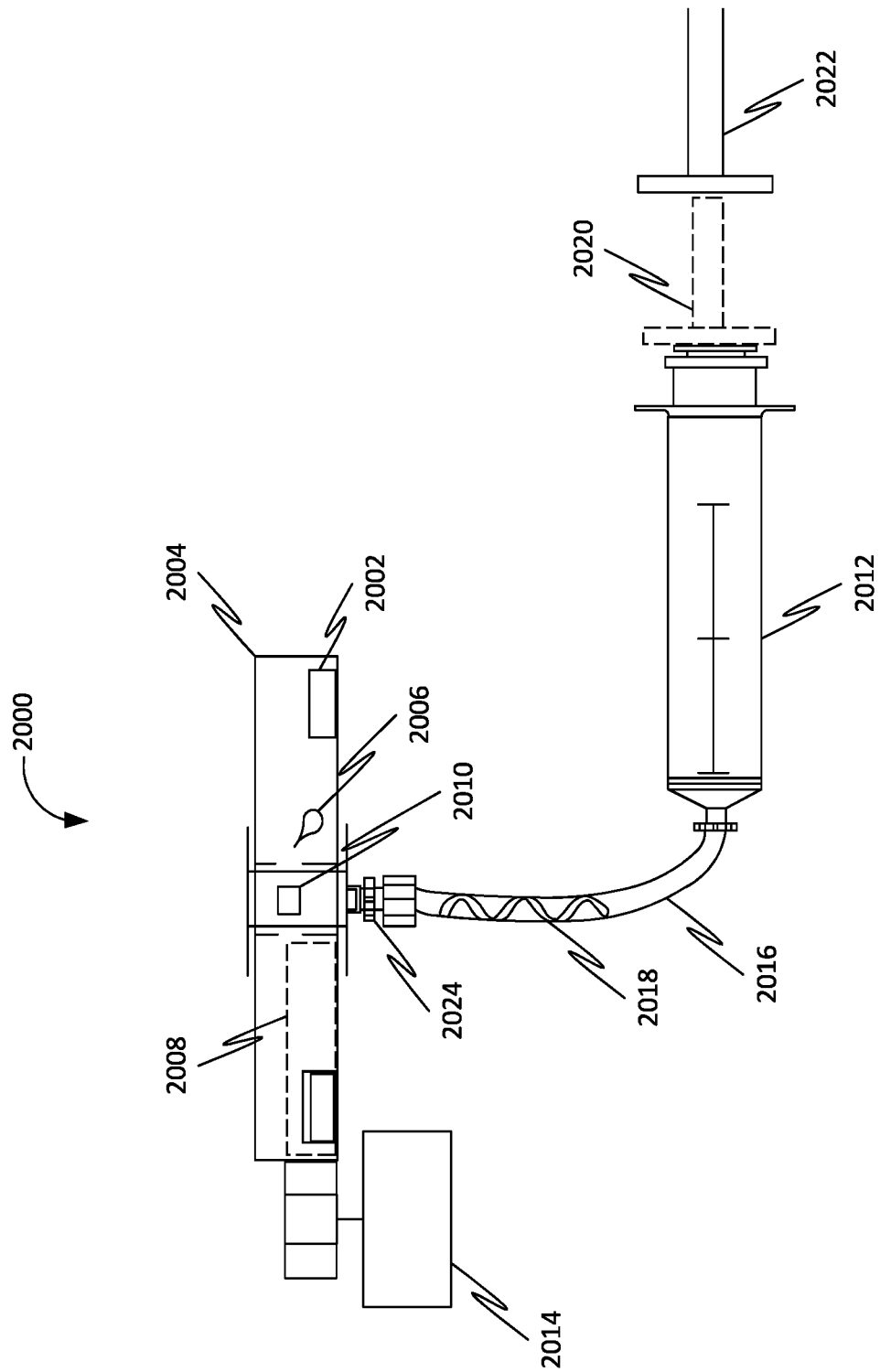
FIG. 20 is a cross-sectional view of a Solid Medication Administration Assembly and a syringe deterrent, in accordance with some embodiments.

FIG. 20 is a cross-sectional view of a Solid Medication Administration Assembly 2000 and a syringe 2012 deterrent, in accordance with some embodiments. Further, the Solid Medication Administration Assembly 2000 deters medication abusers from accessing the solid medication 2002 by locking the medication in a solid medication administration disk 2004. This is achieved by expelling deterrent compound 2006 into the disk thereby forming a deterrent and substrate complex 2008. Further, the Solid Medication Administration Assembly 2000 is consistent of the solid medication administration disk 2004, deterrent pores 2010, a Luer locking connection 2024 for the syringe 2012, and a spin roller connected to a motor 2014. The syringe 2012 and deterrent configuration is consistent of the syringe 2012, a deterrent passage tube 2016, and a deterrent passage tube mixer 2018. The passage tube mixer mixes the deterrent compound and hardening agent until the compound is uniform and activated. The syringe 2012 is compressed by stroking movement 2020 of an actuator arm 2022. As an added feature, one skilled in the art form would appreciate that the solid medication administration disk 2004 allows ease of connection of syringe via the Luer locking connection 2024. In addition, one skilled in the art form would also appreciate that the deterrent pores 2010 allows the flow of the deterrent compound into the solid medication administration disk 2004.

Figure 21:
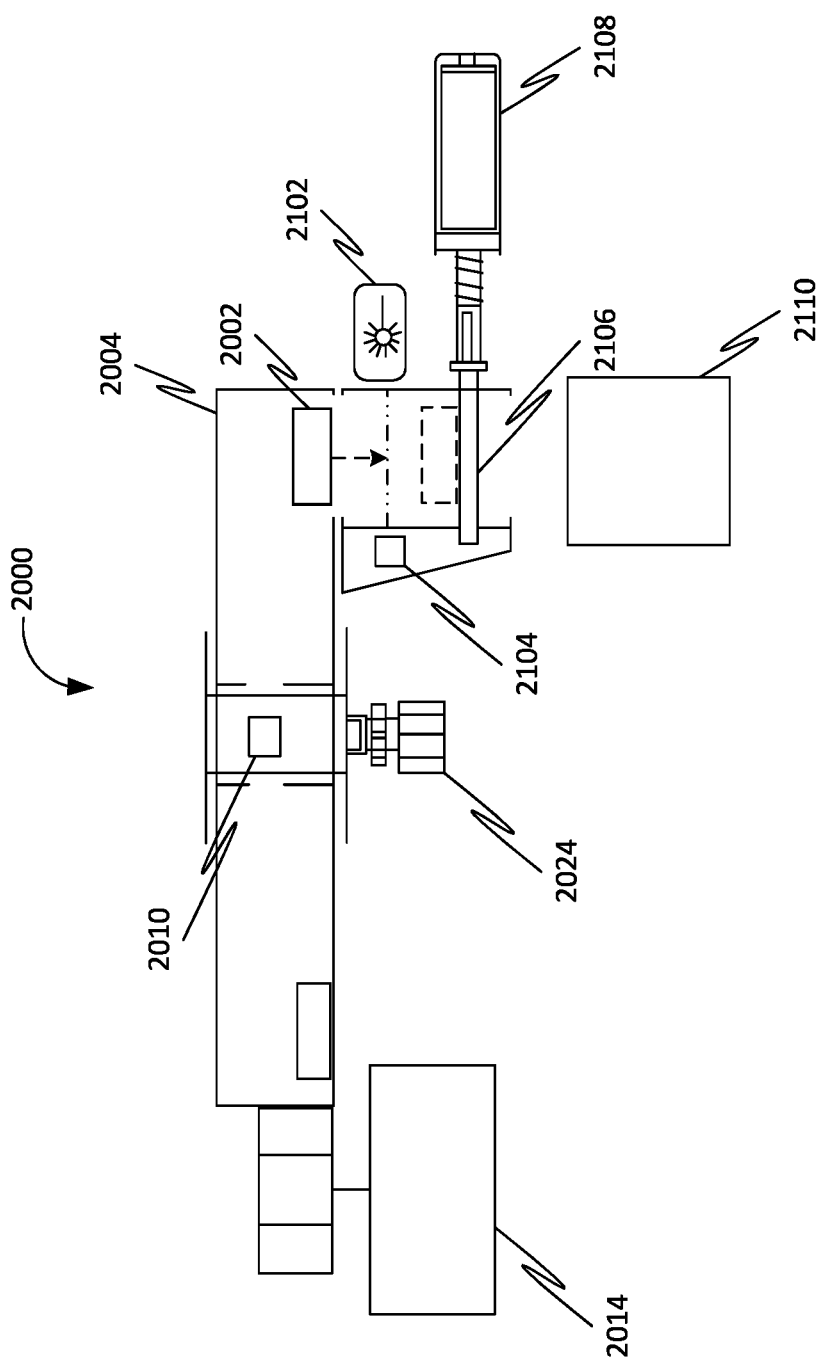
FIG. 21 is a cross-sectional view of a Solid Medication Administration Assembly with extended guard platform and a solenoid drop guard, in accordance with some embodiments.
Figure 22:
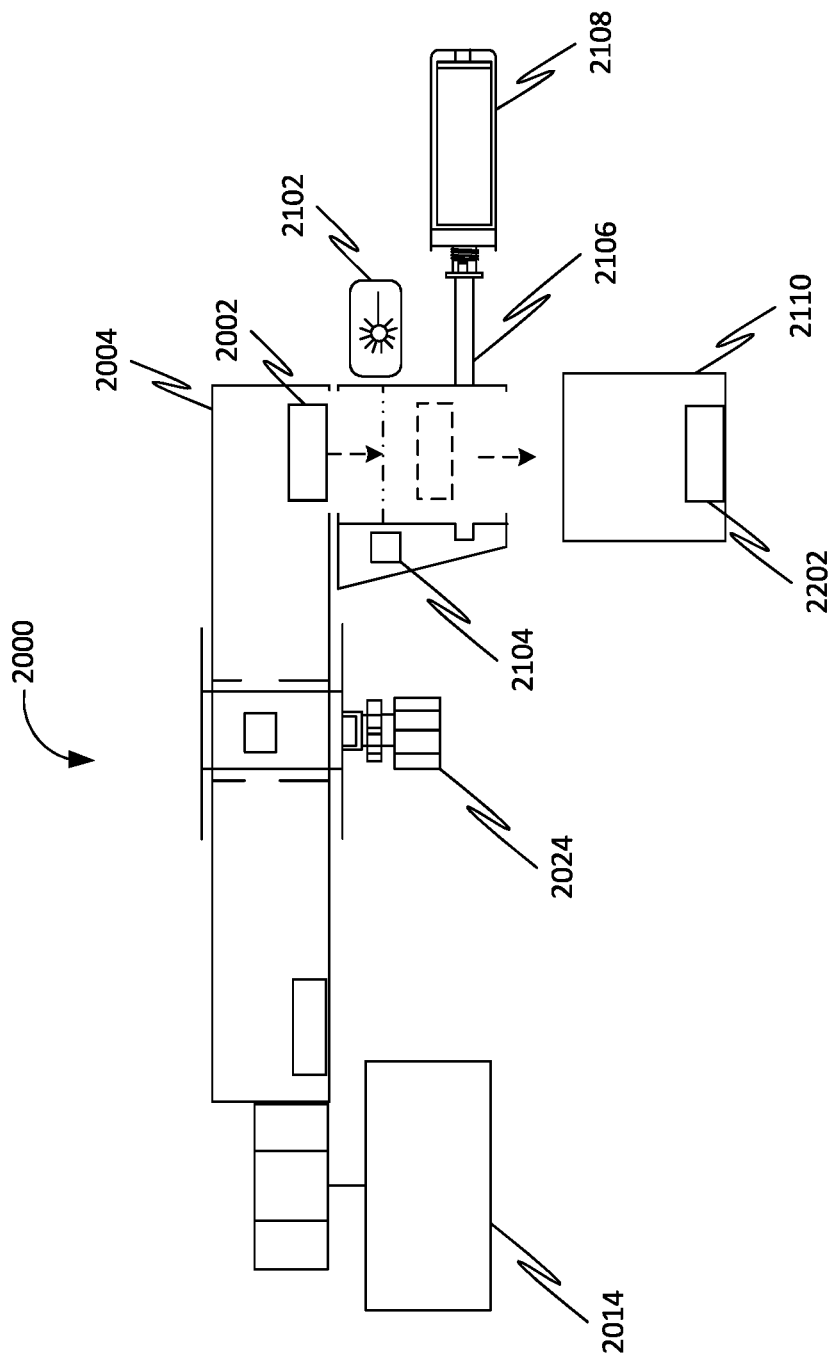
FIG. 22 is a cross-sectional view of a Solid Medication Administration Assembly with a retracted guard platform and a solenoid drop guard, in accordance with some embodiments.

FIG. 21 is a cross-sectional view of a Solid Medication Administration Assembly 2000 with extended guard platform and a solenoid drop guard, in accordance with some embodiments. As an added safety measure to ensure only a specific quantity of solid medication is administered at any set period of time, a laser solid medication counter 2102 and a photodiode light dependent sensor 2104 quantifies the exact number of medication that passes through the laser beam. Every instance of breaking the beam increases the total count by one. For example, if the prescribed dosage is one pill, the spin roller will continue to rotate the solid medication administration disk 2004 until the single solid medication 2002 passes a laser beam and deposits unto the solid medication guard platform 2106. Once the microcontroller verifies that only a single solid medication is deposited to the guard 2106, the signal will be pulsed to the solenoid drop guard 2108 to retract, thereby allowing the solid medication 2002 to drop 2202, as shown in FIG. 22, into the solid dispense cup 2110. When the cycle is finished, the solenoid drop guard 2108 will extend back into the lock position as depicted in FIG. 21.

FIG. 22 is a cross-sectional view of a Solid Medication Administration Assembly 2000 with a retracted guard platform and a solenoid drop guard, in accordance with some embodiments.

Figure 23:
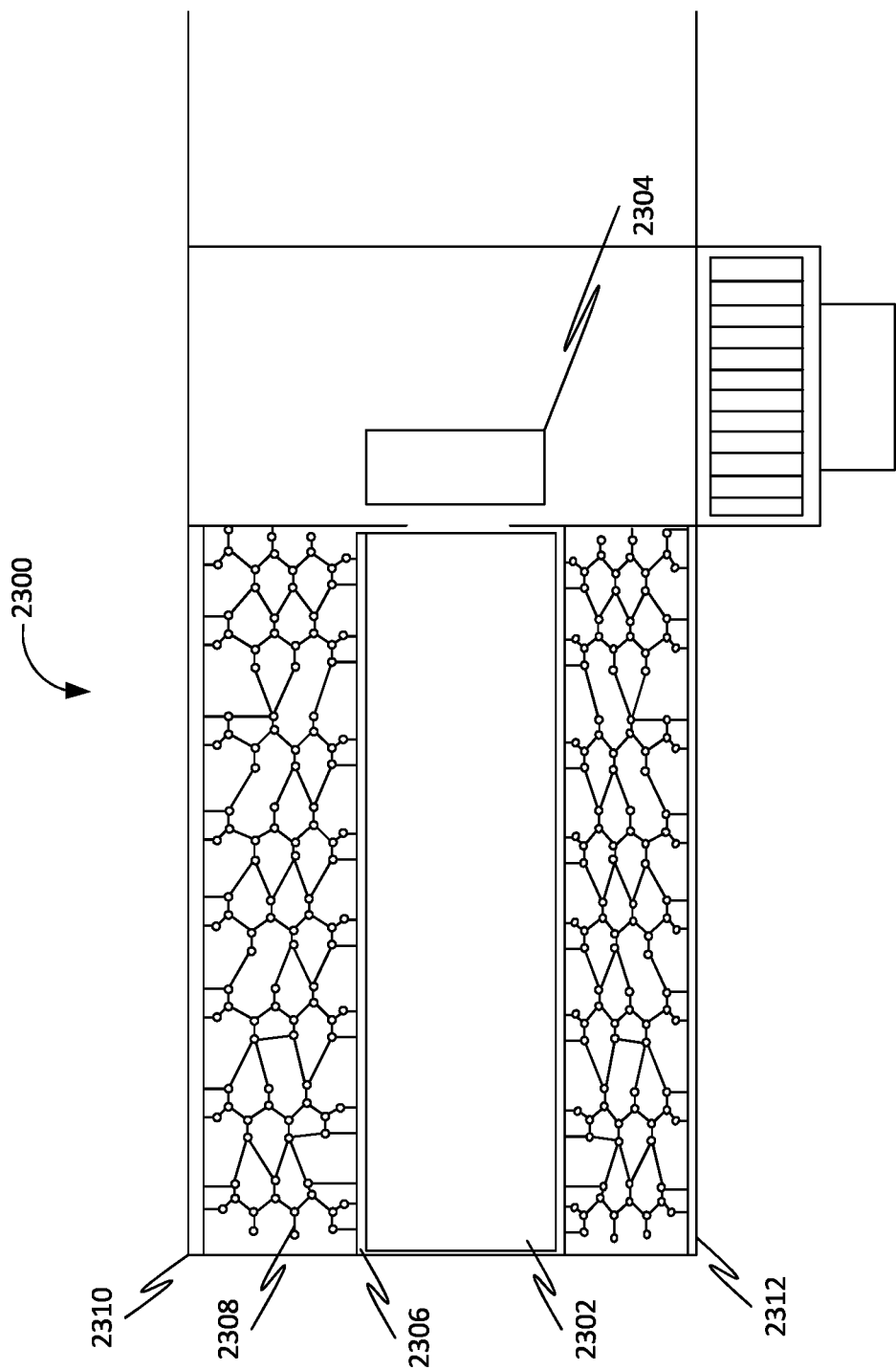
FIG. 23 is an illustration of a Solid Medication Administration Disk with expelled deterrent and Substrate Complex, in accordance with some embodiments.

FIG. 23 is an illustration of a Solid Medication Administration Disk 2300 with expelled deterrent and Substrate Complex, in accordance with some embodiments. Further, a solid medication 2302 is held within a deterrent and substrate complex once the deterrent compound is expelled from deterrent pores 2304 and pumped into the solid medication administration disk 2300. The deterrent compound is a non-metallic substance capable of bonding multiple substrates using the properties of adhesion and cohesion. The deterrent compound may be composed of organic polymers in a liquid or semi-liquid state, and once cured, may become solidified. Known materials that may assume the role of the deterrent compound include adhesives, epoxy, and sealant compounds. During a noncompliant activity, the MAID's microcontroller will activate the actuator arm (not shown), thus expelling the entire contents of the syringe (not shown) into the solid medication administration disk 2300 via the deterrent pores 2304. The substrate in this interaction is the solid medication 2302. Once the deterrent compound encounters the substrate, there will be adhesion of the deterrent compounds to the solid medication 2306. Based on the properties of the deterrent compound, the adhesion may be rapid, thereby forming the harden deterrent and substrate complex (not shown). The inner volume of the medication disk will be consumed by the cohesion of the deterrent compound 2308. In addition, a top 2310 and a bottom 2312 assemblies of the disk will be sealed shut due to adhesion between the deterrent compound and the disk material.

Figure 24:
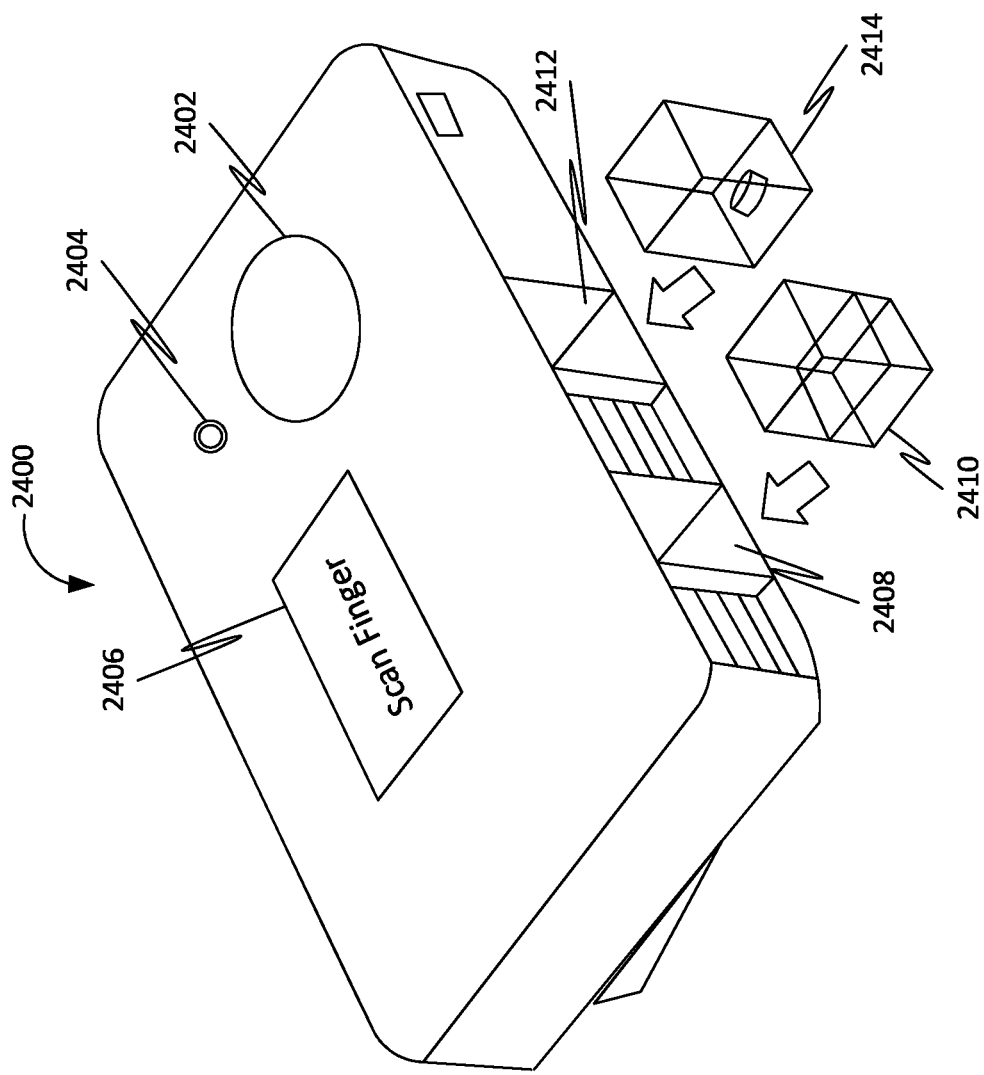
FIG. 24 is a perspective view of a Mobile Administration-Interlocking Device (MAID) with exposed loading docks, in accordance with some embodiments.

FIG. 24 is a perspective view of a Mobile Administration-Interlocking Device (MAID) 2400 with exposed loading docks, in accordance with some embodiments. Further, the MAID 2400 may be fitted with a biometric finger scanner 2402, and an LED indicator light 2404, and an OLED screen 2406. Further, the OLED (organic light-emitting diode) screen 2406 will be integrated into the MAID 2400 and will be used to communicate relevant information to users about system performance. Compared to LCD displays, OLED has several advantages such as better power efficiency, lighter weight and flexibility, and faster response time. Further, the MAID 2400 may also have a liquid dispensing dock 2408 for a liquid dispense cup 2410, and a solid dispensing dock 2412 for a solid dispense cup 2414. Further, pharmaceutical products may be dispensed into these cups following a successful screening of the user's baseline.

Figure 25:
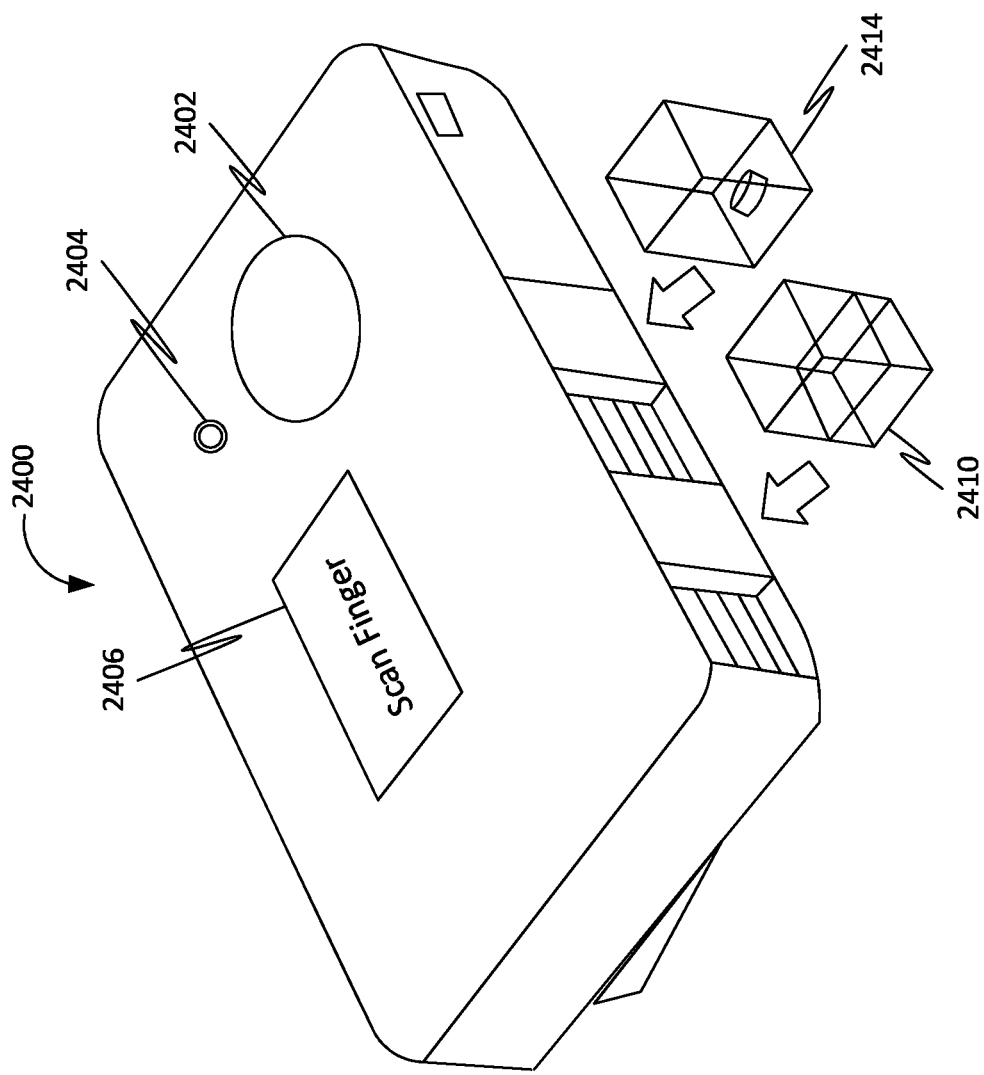
FIG. 25 is a perspective view of a Mobile Administration-Interlocking Device (MAID), in accordance with some embodiments.

FIG. 25 is a perspective view of a Mobile Administration-Interlocking Device (MAID) 2400, in accordance with some embodiments.

Figure 26:
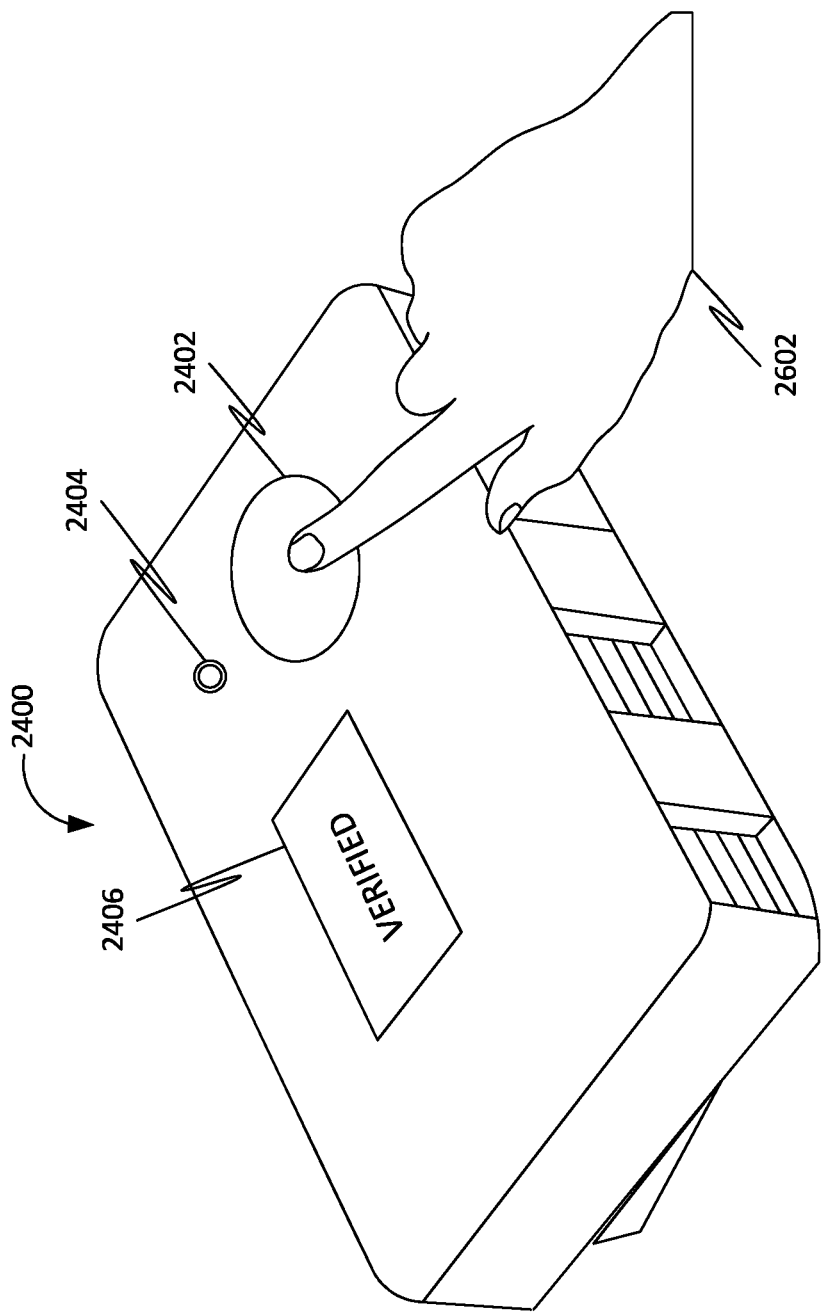
FIG. 26 is a perspective view of a Mobile Administration-Interlocking Device (MAID) verified by a Finger Print Biometric Scanner, in accordance with some embodiments.

FIG. 26 is a perspective view of a Mobile Administration-Interlocking Device (MAID) 2400 verified by a Finger Print Biometric Scanner 2402, in accordance with some embodiments. In order to gain access to the secured medications inside of the MAID 2400, a user must authenticate that they are the intended user of the device. This is achieved by scanning the user's fingerprints 2602 on the fingerprint biometric scanner 2402 and comparing the result in the registration database. The scanned prints are uploaded to the API for verification. If authenticated as a valid user, the disclosed system will permit a request for a dosage. However, if the user is not authenticated as a valid user, a report will be sent to $3^{rd}$ party apps and monitoring devices via the API. and no access to the MAID 2400 will be granted. If continual unauthorized activity is identified, the safety protocols will execute.

Figure 27:
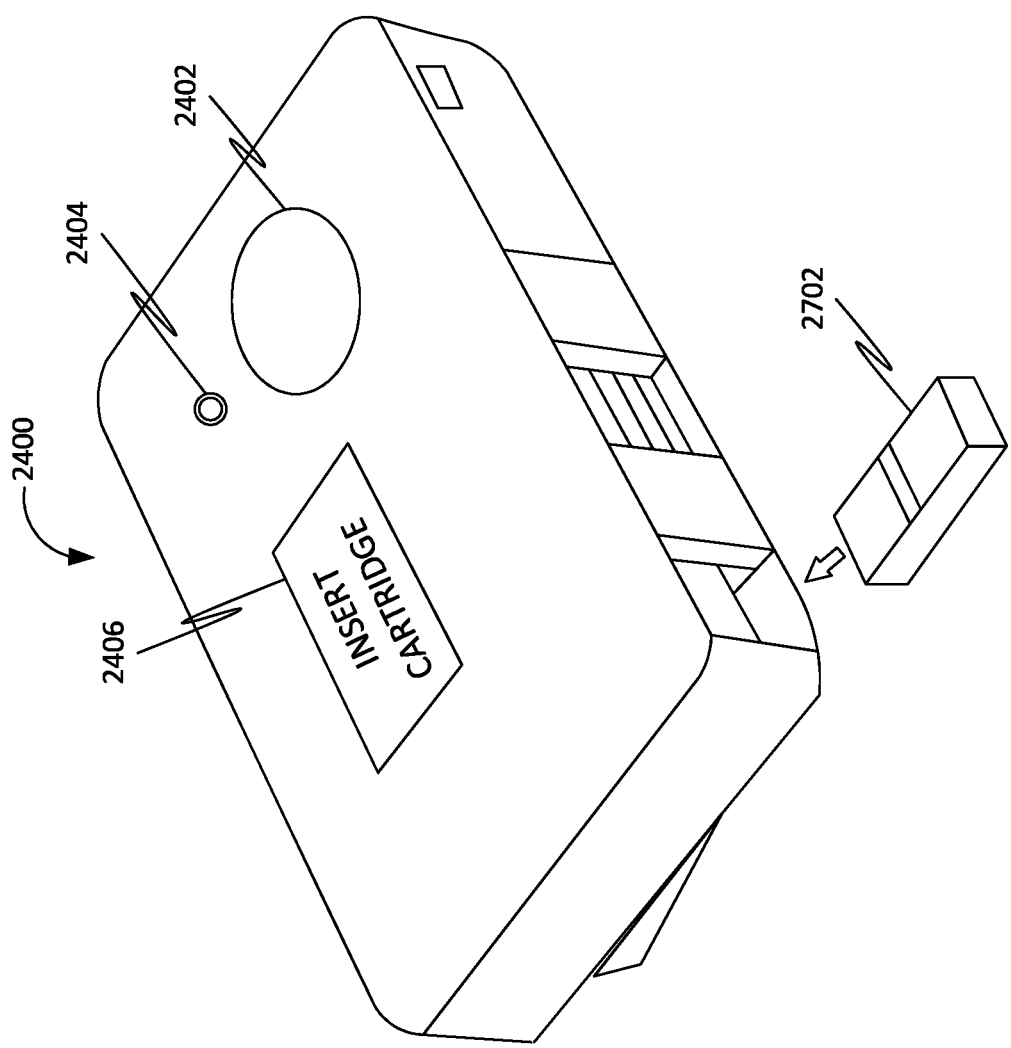
FIG. 27 is a perspective view of a Mobile Administration-Interlocking Device (MAID) with a test cartridge slot, in accordance with some embodiments.

FIG. 27 is a perspective view of a Mobile Administration-Interlocking Device (MAID) 2400 with a test cartridge slot, in accordance with some embodiments. The embodiment of the proposed invention is one example with the MAID 2400 integrated with a test cartridge slot (not shown) and bio reader (not shown). The quantification of hormones or biological analytes) will be conducted with a biological assay cartridge 2702. The cartridge will be loaded into the entry port for the biological assay reader (not shown) for evaluation by the proposed MAID 2400. The biological assay cartridge 2702 will be used to measure the amount of specific analytes within a user. Further, the biological assay cartridge 2702 may be similar to immunochromatographic assay diagnostic tests such as home ovulation tests. The user will apply a biological sample (blood, saliva, urine, etc.) to the biological assay cartridge 2702, and insert it into the entry port for the biological assay reader. Once inside, the biological assay cartridge 2702 will undergo systematic processes for the quantification of the specific analyte or hormone of interest. The test cartridge will also quantify the specific concentration of pharmaceutical products in a user's biological sample. For example, prior to administering an opioid dosage, the MAID 2400 will request a saliva sample to verify that the user is below a specific opioid profile prior to dispensing a dosage.

Figure 28:
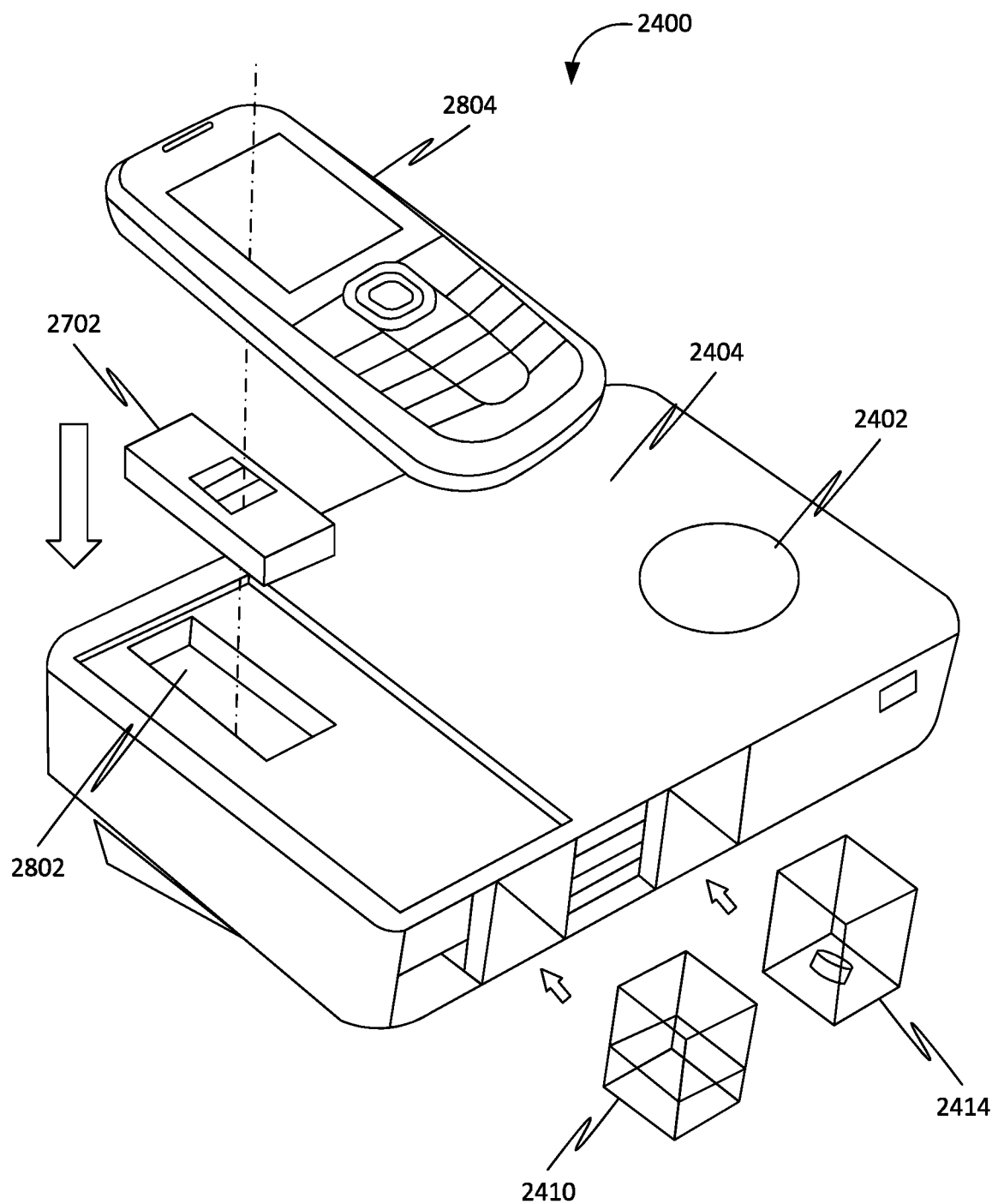
FIG. 28 is a perspective view of a Mobile Administration-Interlocking Device (MAID) with a mobile phone and cartridge docking, in accordance with some embodiments.

FIG. 28 is a perspective view of a Mobile Administration-Interlocking Device (MAID) 2400 with a mobile phone and cartridge docking, in accordance with some embodiments. The integration of the MAID 2400 with mobile phone docking (not shown) allows a user to scan the biological cartridge 2702 by loading it into the cartridge-docking bay 2802 and eclipsing the mobile phone 2804 over the cartridge in the provided slot area. The mobile phone will utilize an app to conduct a quantitative analysis of the assay cartridge. Those skilled in the art form would appreciate the simplified construction of the MAID 2400 by reducing the hardware and processing components and utilizing the configurations of a mobile phone. More specifically, mobile phones have high-quality cameras that may be used to document the cartridge and quantify the concentration of the biological sample.

Figure 29:
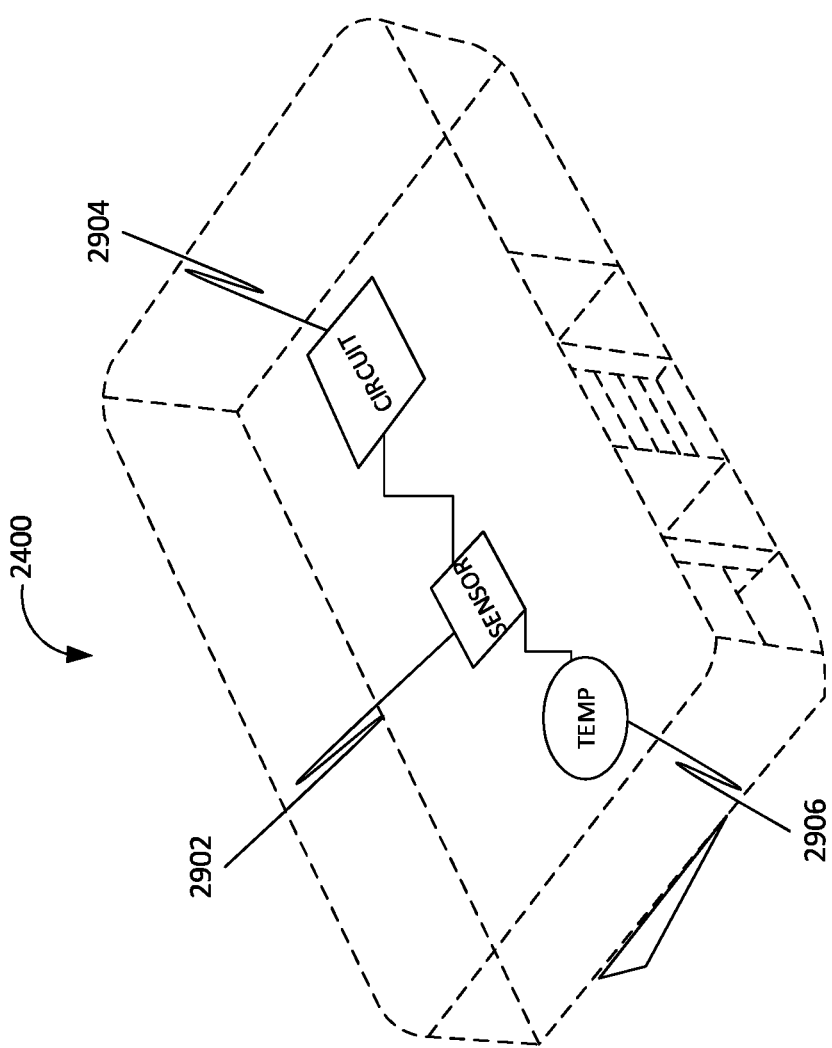
FIG. 29 is an internal view of a Mobile Administration-Interlocking Device (MAID) with a pressure sensor, a temperature sensor, and a circuit board, in accordance with some embodiments.

FIG. 29 is an internal view of a Mobile Administration-Interlocking Device (MAID) 2400 with a pressure sensor 2902, a temperature sensor 2906, and a circuit board 2904, in accordance with some embodiments. In order to protect the structural integrity of the MAID 2400 and the internal medication contents, the pressure sensor 2902 will be utilized to continually monitor the external pressures applied to the device. Further, the pressure sensor 2902 is connected to the circuit board 2904. Further, the pressure sensor 2902 measures the imposed external forces allied to the outer walls of the MAID 2400. If the external pressure exceeds the allowable limit, the MAID 2400 safety protocols will be executed. The temperature sensor 2906 continually monitors the thermal energy allied to the MAID 2400. If a critical temperature is measured by the sensor, the MAID 2400 safety protocols will execute.

Figure 30:
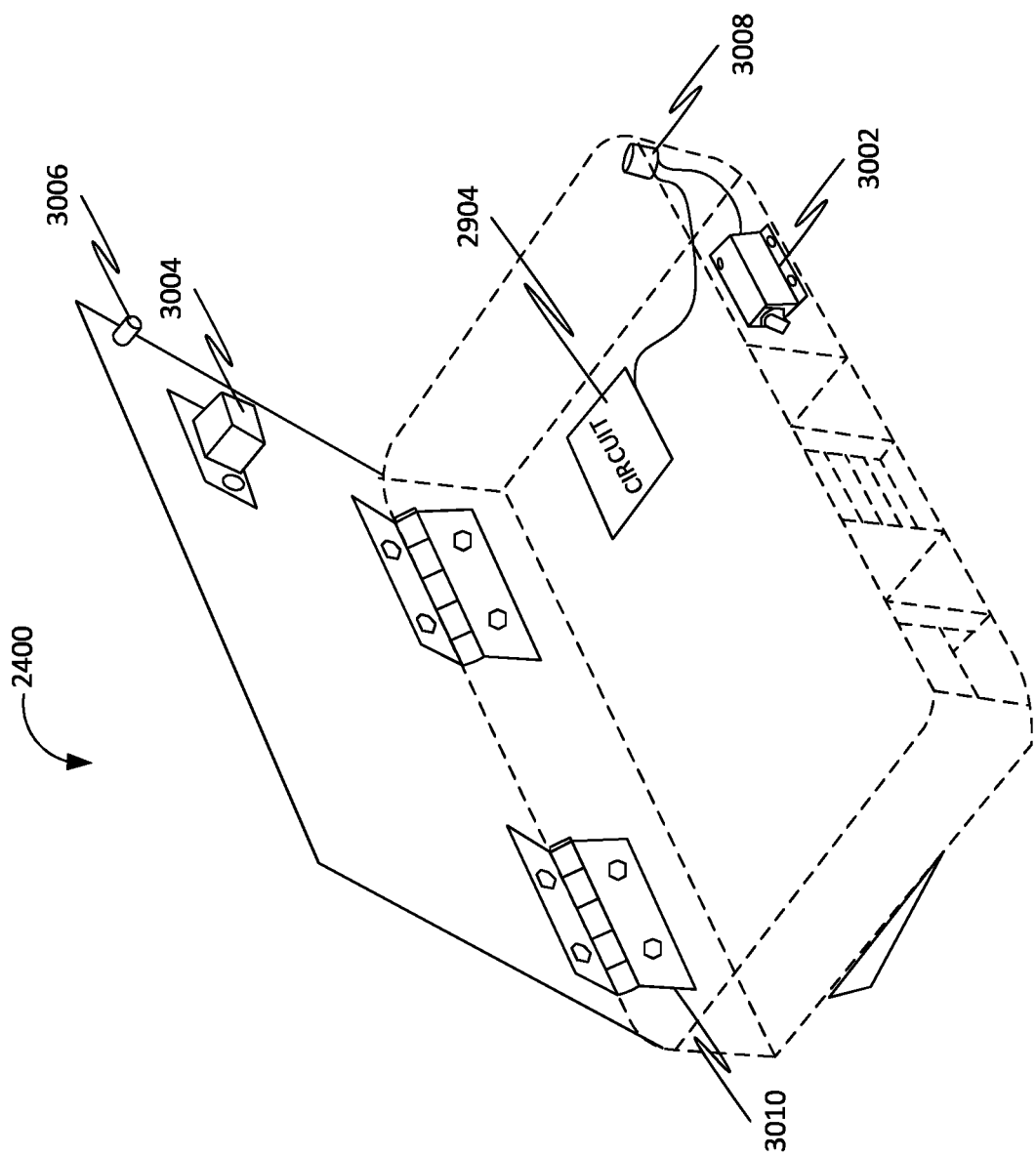
FIG. 30 is an internal view of a Mobile Administration-Interlocking Device (MAID) with locking mechanism and circuit board, in accordance with some embodiments.

FIG. 30 is an internal view of a Mobile Administration-Interlocking Device (MAID) 2400 with locking mechanism and circuit board, in accordance with some embodiments. In order to ensure that the pharmaceutical product inside of the MAID 2400 is secured at all times, the device will be locked from the inside using the solenoid access bolt 3002, a lockbox 3004, a docking pin 3006, and a docking sensor 3008. The docking sensor will be connected to the circuit board 2904. When the docking pin 3006 is inside of the docking sensor 3008, there will be a closed circuit or a complete circuit connection. When the docking pin 3006 is outside of the docking sensor 3008, the circuit will be open, or an incomplete circuit connection. The MAID 2400 will also have hinges 3010 for structural support.

Figure 31:
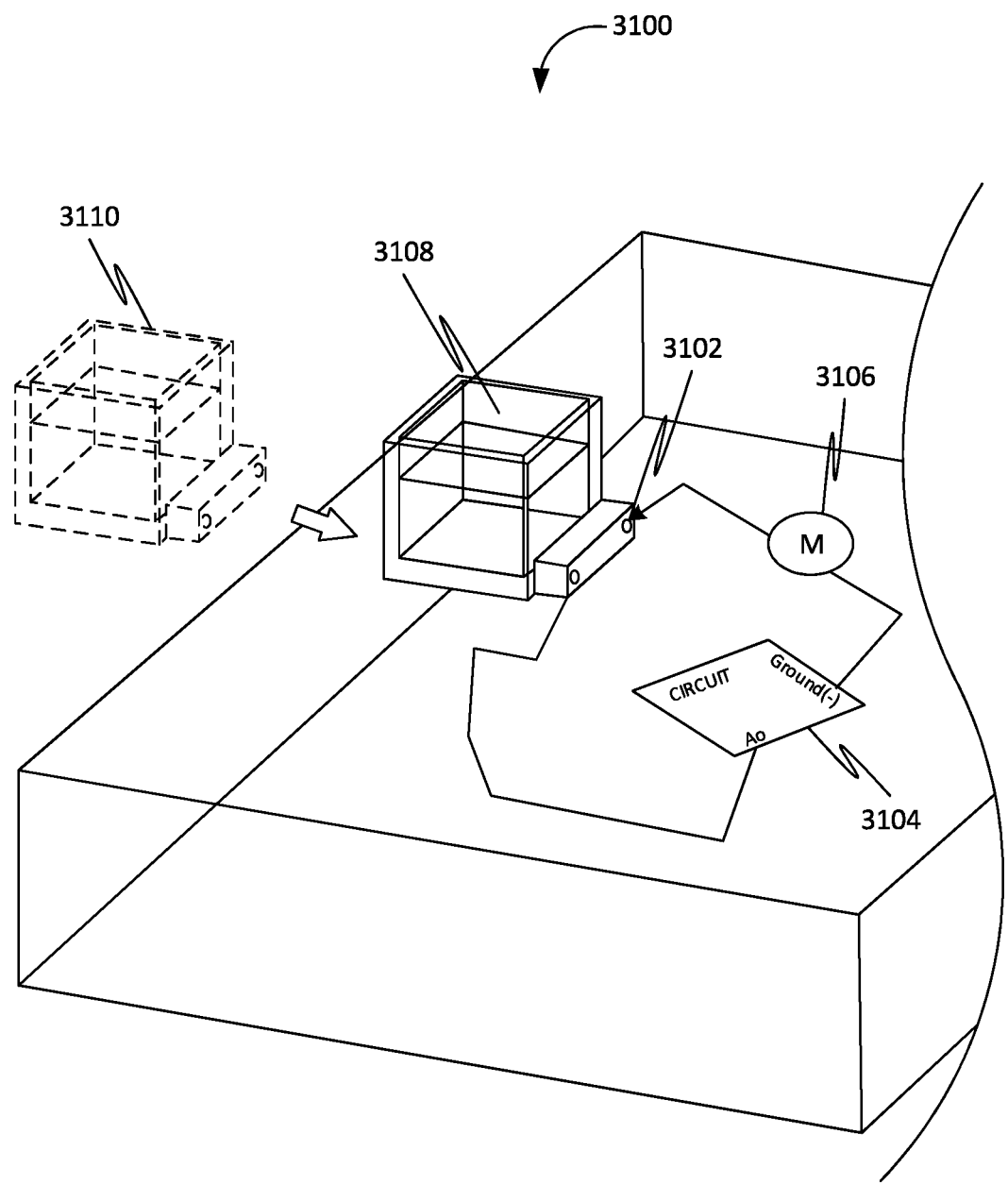
FIG. 31 is an illustration of a liquid dispense cup and a deactivating motor mechanism, in accordance with some embodiments.
Figure 32:
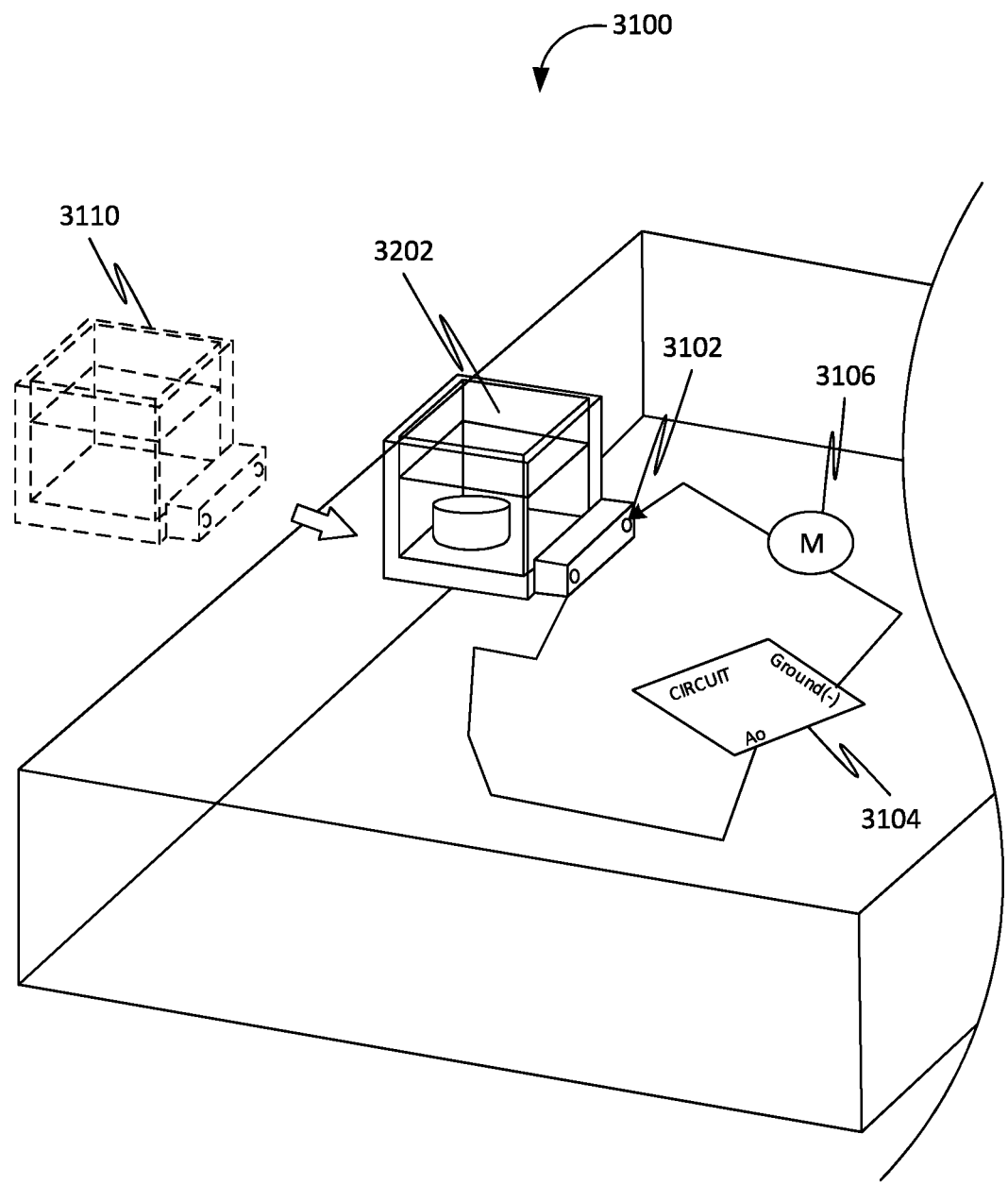
FIG. 32 is an illustration of a solid dispense cup and a deactivating motor mechanism, in accordance with some embodiments.

FIG. 31 is a partial view of a Mobile Administration-Interlocking Device (MAID) 3100 showing a liquid dispense cup 3108 and a deactivating motor mechanism, in accordance with some embodiments. Further, the Mobile Administration-Interlocking Device (MAID) 3100 may include connector pins 3102, a circuit board 3104, an activating motor 3106, a solid dispense cup 3202, as shown in FIG. 32, and a liquid dispense cup 3108. When the dispensing cups are outside of the MAID 3100 loading docks 3110, there will be an open circuit, thus the activating motor 3106, which represents the circulation pump for the liquid medication and the spin roller for the solid medication, will not activate. This prevents the administration of medications while the cups are out of place. In addition, this deters potential medication abusers from gaining access to MAID 3100 and its contents. Once the cups are positioned back into the locking docks, the circuit will be closed, or complete. At that point, the motor will have the potential to activate, thereby administering the prescribed dosage.

FIG. 32 is a partial view of a Mobile Administration-Interlocking Device (MAID) 3100 showing the solid dispense cup 3202 and a deactivating motor mechanism, in accordance with some embodiments.

Figure 33:
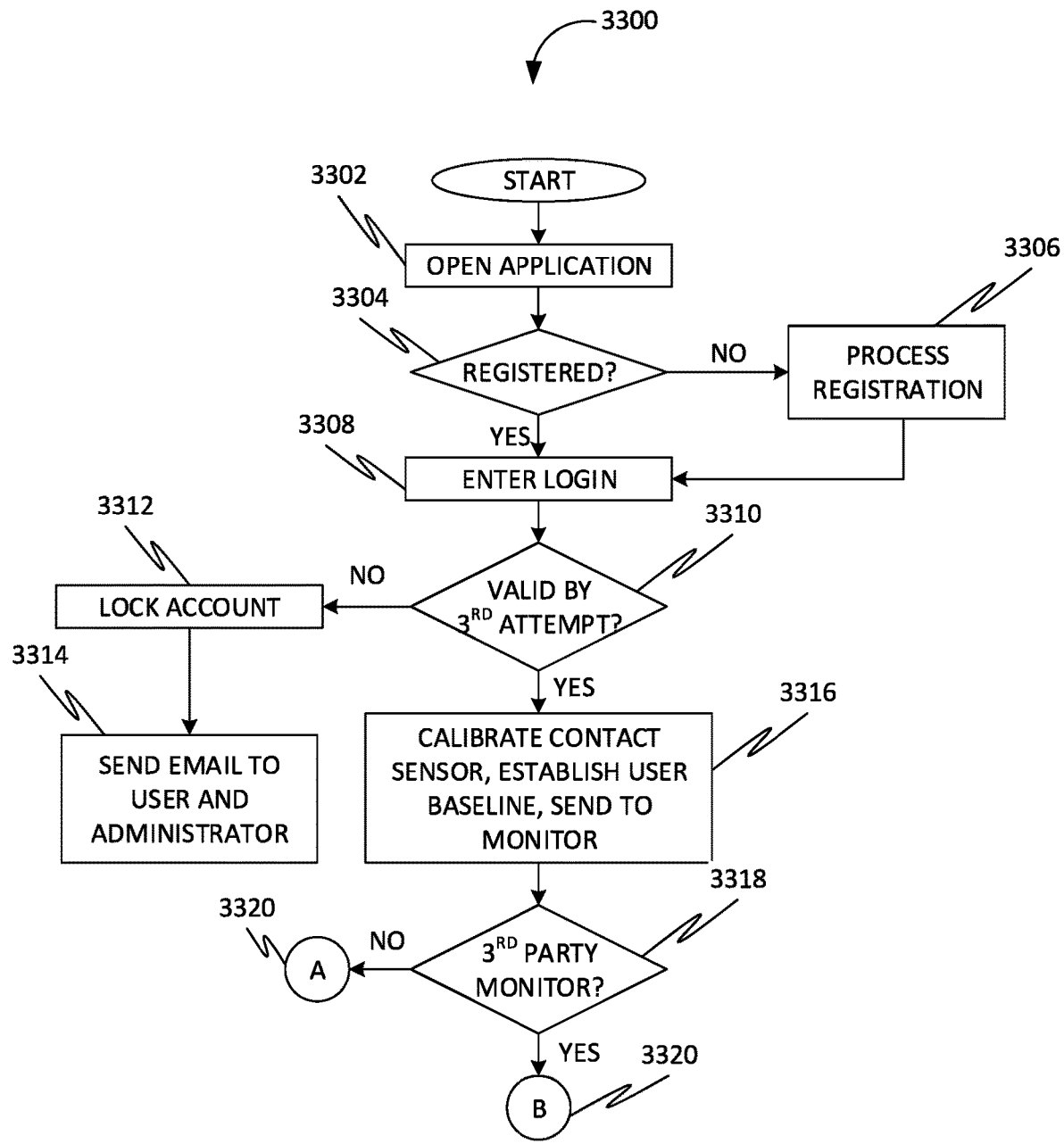
FIG. 33 is a flow diagram of a method associated with a digital health system, in accordance with some embodiments.

FIG. 33 is a flow diagram of a method 3300 associated with a digital health system, in accordance with some embodiments. Accordingly, at 3302, the method 3300 may include the user to open the computer application for product services 3302 when preparing to interact with the MAID device and service platform.

Further, at 3304, the method 3300 may include checking if a user is registered.

Further, at 3306, the method 300 may include a process registration if the user is not registered. Further, the process registration may include a user prompted to create a unique username and password 011 their first instance of logging in 3306.

Further, at 3308, the user may be prompted to re-enter their credentials for a successful login. If the user entered an incorrect credential, they will be prompted to attempt again.

Further, at 3310, the method may include verifying if the user has successfully logged in.

Further, at 3312, the method may include locking the user account upon three consecutive unsuccessful attempts.

Further, at 3314, the method 3300 may include transmitting an email with instructions will be sent to the user's registered email account.

Further, at 3316, after 3310, the method may include systematic calibration upon verifying the username and password credential as valid. If a wearable device is monitoring the user, the sensors will calibrate with a predetermined maximum and minimum value, followed by a measurement of the user's baseline.

Further, at 3318, the method may include transmitting a successful notification to the API and third parties via the API. The system will conduct a crosscheck to determine if the monitoring activity will be for research 3321 or self-monitoring mode 3320.

Figure 34:
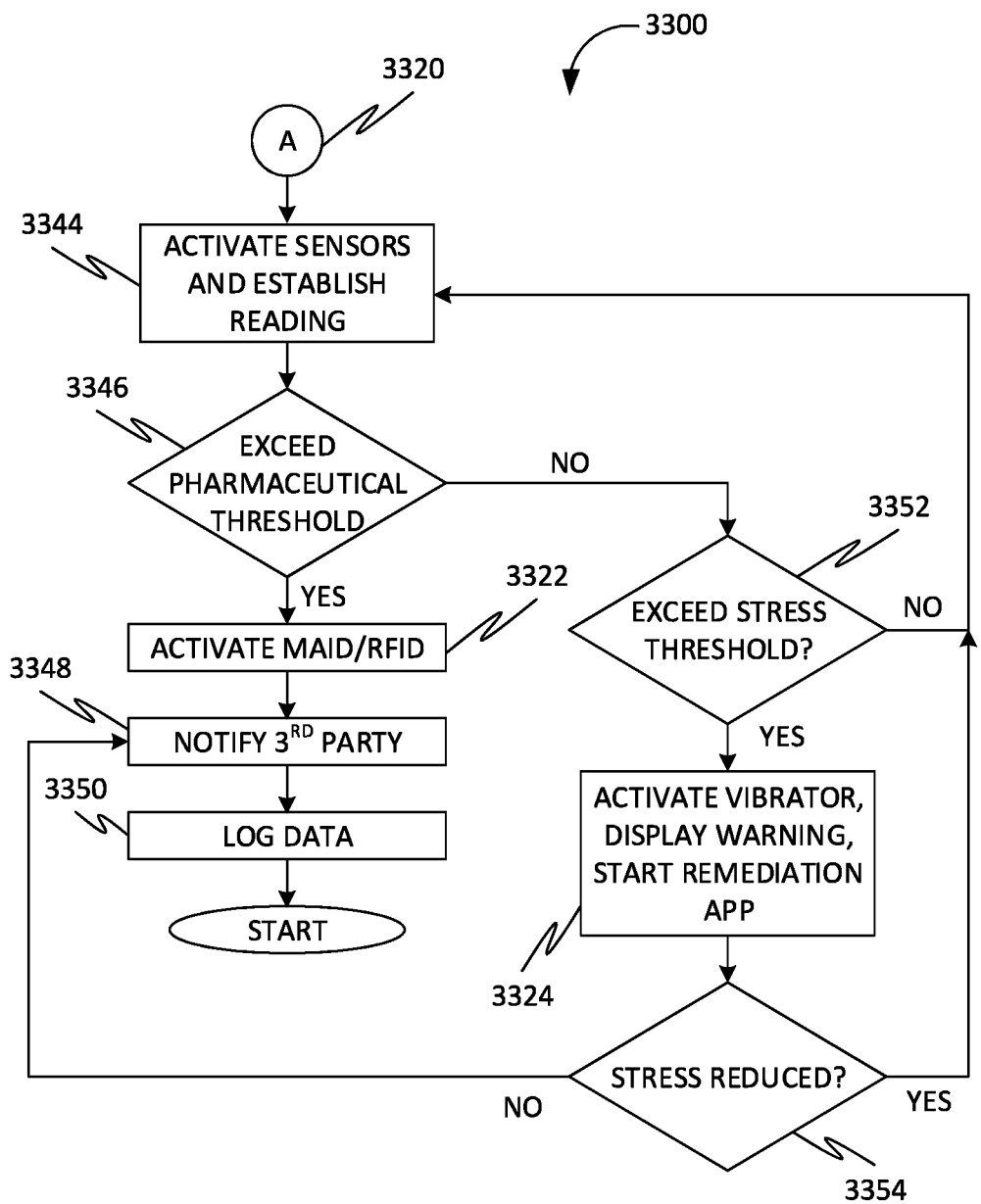
FIG. 34 is a continuation flow diagram of the method associated with the digital health system, in accordance with some embodiments.

FIG. 34 is a continuation flow diagram of the method 3300 associated with the digital health system, in accordance with some embodiments. Further, after 3318, at 3320, the method 3300 may include the digital health system in self-monitoring mode.

Further, at 3344, the method 3300 may include activating sensors and establishing readings. If the service being offered is for self-monitoring, such as outpatient care, the sensors will activate and begin monitoring activity, as shown in FIG. 34. The service provided in the self-monitoring mode is similar to the research mode shown in FIG. 35 and described below.

Further, at 3346, the method 3300 may include checking if the user exceeds a pharmaceutical threshold.

Further, after 3346, at 3322, the method 3300 may include activating MAID and the Radio Frequency Identification Device (RFID) upon exceeding the pharmaceutical threshold by the user.

Further, at 3348, the method 3300 may include notifying third parties.

Further, at 3350, the method 3300 may include logging data.

Further, after 3346, at 3352, the method 3300 may include confirming if the user exceeded stress threshold.

Further, upon confirmation of the user exceeding the stress threshold at 3346, at 3324, the method 3300 may include activating vibrator, display warning, and starting the remediation application.

Further, at 3354, the method 3300 may confirm if the stress of the user is reduced.

Further, upon confirming no reduction in stress of the user, the method 3300 may lead to 3348.

Further, upon confirming a reduction in stress of the user, the method 3300 may follow back to 3344.

Further, after 3352, upon confirming the user did not exceed the stress threshold, the method may proceed to 3344.

Figure 35:
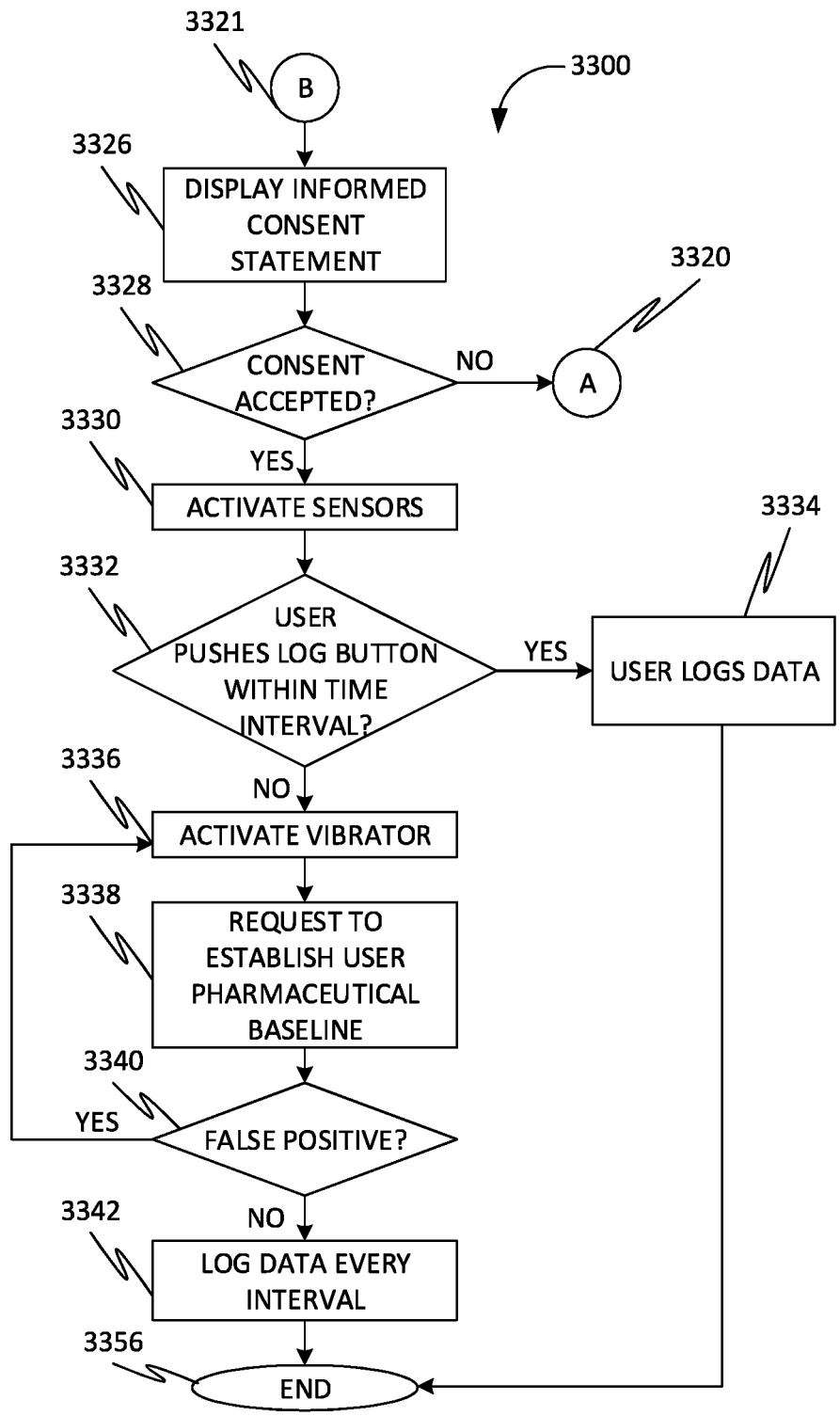
FIG. 35 is a continuation flow diagram of the method associated with the digital health system, in accordance with some embodiments.

FIG. 35 is a continuation flow diagram of the method 3300 associated with the digital health system, in accordance with some embodiments. Further, at 3321, the method 3300 may include the digital health system in the research mode.

Further, after 3321, at 3326, the method may include displaying an informed consent statement. If the service being offered is for research, such as inpatient care, the user will be navigated to an informed consent prompt screen.

Further, at 3328, the method 3300 may include confirming if the user accepted the consent statement.

Further, upon successful acceptance of the consent statement by the user, at 3330, the method 3300 may include the beginning of the monitoring service. Further, sensors may be activated.

Further, at 3332, the method 3300 may include confirming if the user pushed a log button within a time interval. In research mode, the wearable device will continuously monitor the activities of the biometric sensors on intervals of at least 15 minutes.

Further, upon confirming the user did not push the log button, at 3336, the method 3300 may include activating vibrator. Further, after every cycle of 15 minutes, the vibrator will alarm, and the user will be requested for a sample and/or feedback.

Further, at 3338, the method may include requesting the user to establish a pharmaceutical baseline. Parallel to vibrator alarming, the system will send a prompting message on the display screen.

Further, at 3340, the method 3300 may include determining if there was an instance of a false positive.

Further, upon confirming the false positive, at 3342, the method 3300 may proceed to 3336. Further, the user may be asked to resubmit a sample.

Further, after 3340, upon determining the sample to be acceptable with no false positive, at 3342, the method 3300 may include logging the data to the API and saved in the database. In research mode, the user will also have the ability to document self-reports about their condition and reaction to different stimuli.

Further, at 3356, the method 3300 may include an ending step.

Further, after 3332, upon confirming the user pushing the log button within the fixed time interval, at 3334, method 3300 may include the user pushing the log button on the application, and enter their corresponding feedback data. Once received, the feedback data will be logged in the API. The data logger will continue to document sensor activity in the API every cycle of 15 minutes.

Further, after 3328, upon confirming declining of the consent statement, the method 3300 may proceed to 3320. Further, upon declining the consent statement, the user may be sent back to the opening portal of the program.

Figure 36:
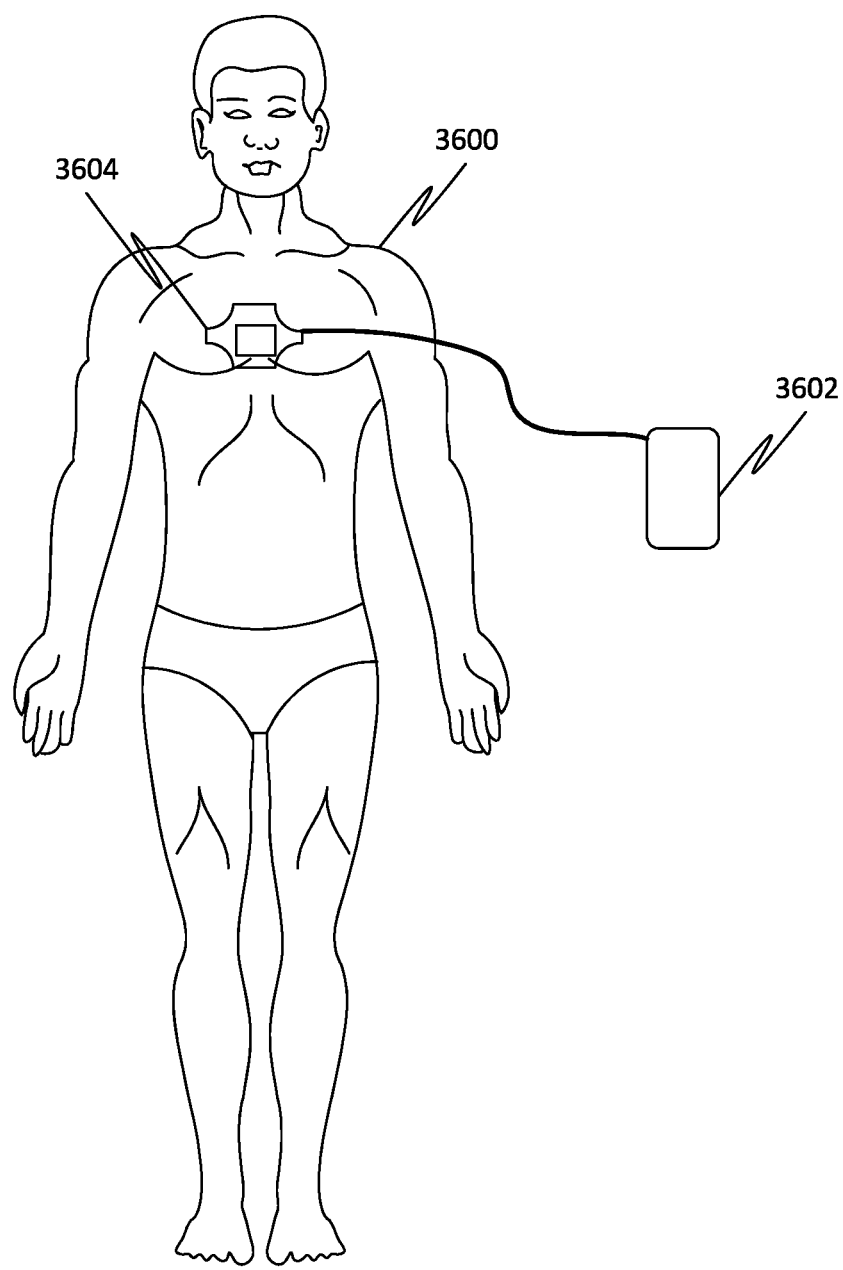
FIG. 36 is an illustration of a user with a sensor node and sensor patch, in accordance with some embodiments.

FIG. 36 is an illustration of a user 3600 with a sensor node and sensor patch 3604, in accordance with some embodiments. The sensor node device 3602 is connected to the sensor patch 3604 via a lanyard or wire harness connection. The sensor patch 3604 is affixed to the abdominal region of the user's body.

Figure 37:
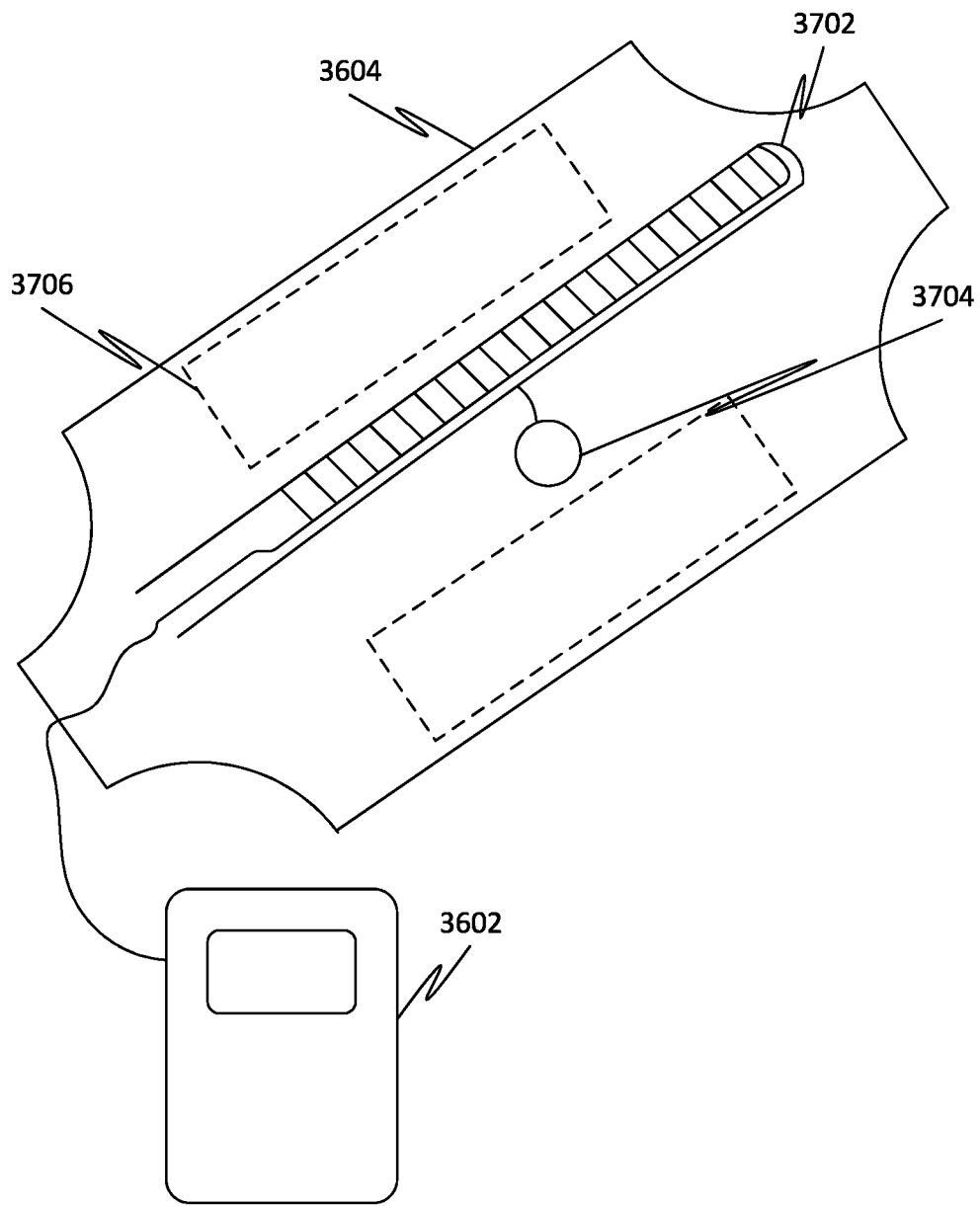
FIG. 37 is an illustration of the components of a sensor patch, in accordance with some embodiments.

FIG. 37 is an illustration of the components of the sensor patch 3604, in accordance with some embodiments. The sensor patch 3604 has an embedded flex variable resistor sensor 3702, a body temperature sensor 3704, and an adhesive backing 3706 to fix the sensor patch 3604 to the epidermal layer of the user.

Figure 38:
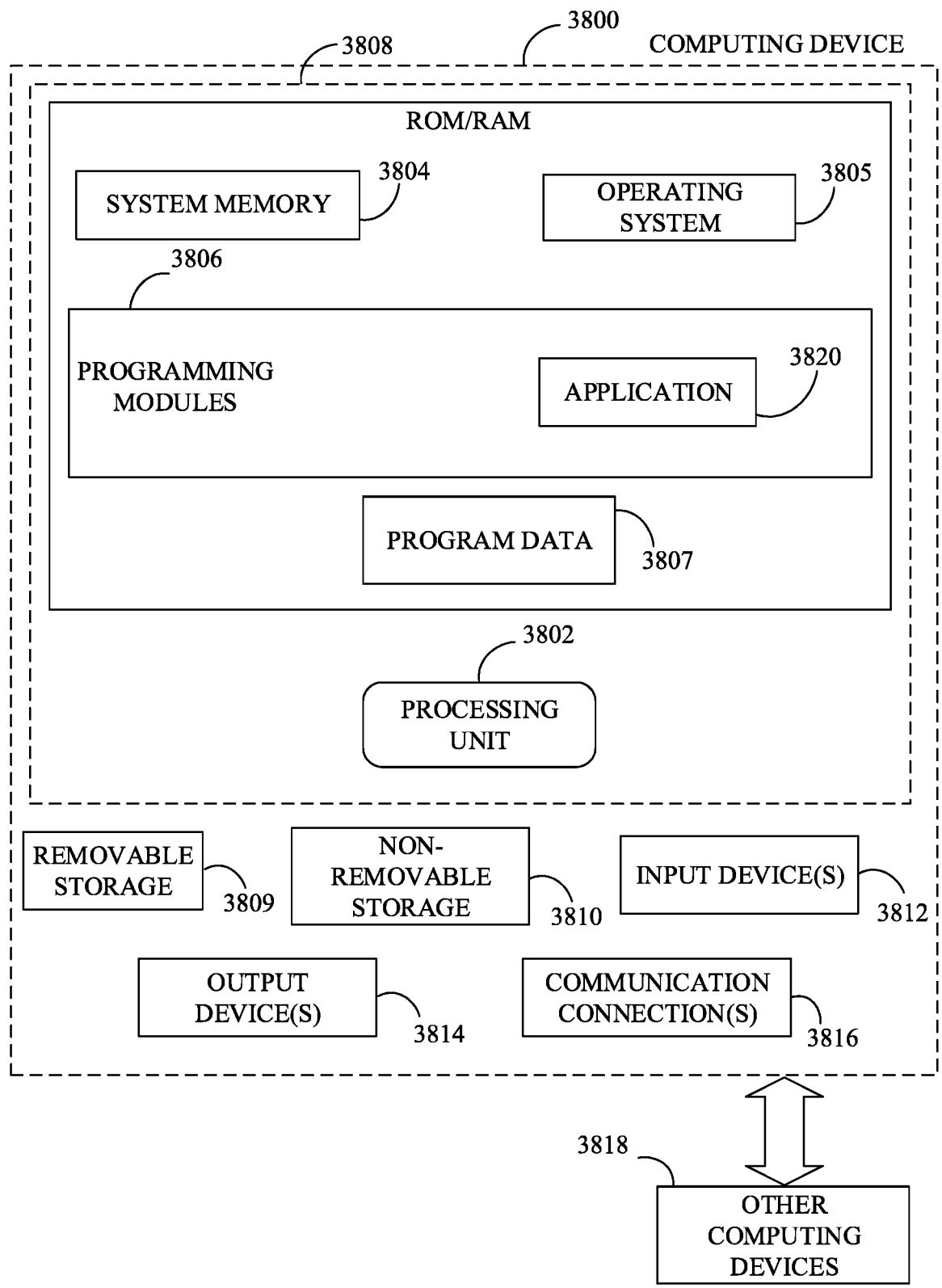
FIG. 38 is a block diagram of a computing device for implementing the methods disclosed herein, in accordance with some embodiments.

With reference to FIG. 38, a system consistent with an embodiment of the disclosure may include a computing device or cloud service, such as computing device 3800. In a basic configuration, computing device 3800 may include at least one processing unit 3802 and a system memory 3804. Depending on the configuration and type of computing device, system memory 3804 may comprise, but is not limited to, volatile (e.g. random-access memory (RAM)), non-volatile (e.g. read-only memory (ROM)), flash memory, or any combination.

System memory 3804 may include operating system 3805, one or more programming modules 3806, and may include a program data 3807. Operating system 3805, for example, may be suitable for controlling computing device 3800's operation. In one embodiment, programming modules 3806 may include image-processing module, machine learning module. Furthermore, embodiments of the disclosure may be practiced in conjunction with a graphics library, other operating systems, or any other application program and is not limited to any particular application or system. This basic configuration is illustrated in FIG. 38 by those components within a dashed line 3808.

Computing device 3800 may have additional features or functionality. For example, computing device 3800 may also include additional data storage devices (removable and/or non-removable) such as, for example, magnetic disks, optical disks, or tape. Such additional storage is illustrated in FIG. 38 by a removable storage 3809 and a non-removable storage 3810. Computer storage media may include volatile and non-volatile, removable and non-removable media implemented in any method or technology for storage of information, such as computer-readable instructions, data structures, program modules, or other data. System memory 3804, removable storage 3809, and non-removable storage 3810 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 3800. Any such computer storage media may be part of device 3800. Computing device 3800 may also have input device(s) 3812 such as a keyboard, a mouse, a pen, a sound input device, a touch input device, a location sensor, a camera, a biometric sensor, etc. Output device(s) 3814 such as a display, speakers, a printer, etc. may also be included. The aforementioned devices are examples and others may be used.

Computing device 3800 may also contain a communication connection 3816 that may allow device 3800 to communicate with other computing devices 3818, such as over a network in a distributed computing environment, for example, an intranet or the Internet. Communication connection 3816 is one example of communication media. Communication media may typically be embodied by computer-readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer-readable media as used herein may include both storage media and communication media.

As stated above, a number of program modules and data files may be stored in system memory 3804, including operating system 3805. While executing on processing unit 3802, programming modules 3806 (e.g., application 3820 such as a media player) may perform processes including, for example, one or more stages of methods, algorithms, systems, applications, servers, databases as described above. The aforementioned process is an example, and processing unit 3802 may perform other processes.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general-purpose graphics processor-based systems, multiprocessor systems, microprocessor-based or programmable consumer electronics, application-specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer-readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example, but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may, in fact, be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid-state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

Although the present disclosure has been explained in relation to its preferred embodiment, it is to be understood that many other possible modifications and variations can be made without departing from the spirit and scope of the disclosure.

ASPECTS

1. A safe and effective method and system for the administration of pharmaceutical products at point of care, comprising:
a mobile administration-interlocking device (MAID); a mobile integrated computing device;
a mobile application; and a wearable device.

2. The MAID of aspect 1, wherein a MAID device comprising:
A micro filter; a circulation pump; a solenoid clamp A; a solenoid clamp B; an antagonist reservoir; an agonist reservoir; a flow Sensor; linear syringe Actuator; solenoid access bolt; OLED screen; alarm buzzer; communication module; biometric finger scanner; battery management system: battery; microcontroller; spin roller; solenoid drop guard; laser solid medication counter; pressure sensor; embedded control circuit; dock sensor; solid medication administration disk; solid dispense cup; liquid dispense cup; liquid medication administration assembly; LED indicator light; solid dispensing dock; liquid dispensing dock; solid medication administration assembly; a solid medication guard platform; a photodiode/light dependent resistor; a docking pin; a reinforced lock Box; and an embedded temperature sensor.

3. The Solid Medication Administration Assembly of aspect 2, further comprising a spin roller; deterrent pores; luer locking connection for the syringe; deterrent passage tube mixer; deterrent passage tube; syringe; actuator arm; a replaceable solid medication administration disk; and deterrent compound.

4. The deterrent compound of aspect 3, wherein the deterrent compound is a non-metallic substance capable of bonding multiple substrates using the properties of adhesion and cohesion. The deterrent compound is an organic polymer in a liquid or semi-liquid state, and once cured, may become solidified.

5. The deterrent compound of aspect 4, wherein the deterrent compound includes adhesives, epoxies, or sealant compounds.

6. The liquid medication administration assembly of aspect 2, further comprising a circulation pump; a micro air filter; a tubing T connector; a solenoid clamp A; an antagonist reservoir bag; solenoid clamp B; a liquid flow sensor in line with an agonist reservoir bag; and a bag coupler connector that connects the antagonist reservoir bag to the agonist reservoir bag.

7. The MAID device of aspect 2, further comprising a solid dispensing dock for solid medications such as pills; and a liquid dispensing dock for liquid or aqueous pharmaceutical medications.

8. The MAID device of aspect 2, wherein a biological assay reader is embedded to quantify the reagent value of a biological assay cartridge.

9. The MAID device of aspect 2, wherein a cartridge-docking bay is embedded to seat a biological assay cartridge for quantification with a mobile phone.

10. The mobile integrated computer device of aspect 1, wherein the mobile integrated computer device is adapted to communicate with the MAID device.

11. The mobile integrated computer device of aspect 10, wherein a user mobile integrated computer device is adapted to communicate with the MAID device, and further adapted to communicate via the Internet.

12. The mobile integrated computer device of aspect 10, wherein a third-party mobile integrated computer device is adapted to communicate with the user mobile integrated computer device via the Internet to allow a third party to access information from the MAID device with a secure login and password.

13. The MAID device of aspect 1, further comprising:
A linear syringe Actuator; solenoid access bolt; OLED screen: alarm buzzer; communication module; biometric finger scanner; battery management system; battery; microcontroller; spin roller; solenoid drop guard; laser solid medication counter; pressure sensor: embedded control circuit: dock sensor: solid medication administration disk: solid dispense cup; LED indicator light; solid dispensing dock; a solid medication administration assembly; a solid medication guard platform: a photodiode/light-dependent resistor; a docking pin; a reinforced lock Box; an embedded temperature sensor; and a biological assay cartridge docking bay.

14. The liquid medication administration assembly of aspect 6, wherein solenoid clamp A controls the flow of fluid and air in and out of the antagonist reservoir bag.

15. The liquid medication administration assembly of aspect 6. wherein solenoid clamp B controls the flow of fluid and air in and out of the agonist reservoir bag.

16. The liquid medication administration assembly of aspect 6. wherein the contents of the antagonist reservoir bag is pumped by the circulation pump via the bag coupler connector and into the agonist reservoir bag.

17. The deterrent compound of aspect 5, wherein the deterrent compound is stored inside of a syringe housed in the MAID device.

18. The deterrent compound of aspect 17, wherein the deterrent compound is expelled from the syringe using stroking motion by an actuator arm.

19. The mobile application of aspect 1, wherein the application software is accessible from a mobile integrated computing device.

20. The wearable device of aspect 1, comprising a sensor patch; and a sensor node.

21. The sensor patch of aspect 20. comprising:
an embedded flex variable resistor sensor; a body temperature sensor; and an adhesive backing to fix the patch to the epidermal layer of the user's abdominal region.

22. The sensor node of aspect 20, wherein data from the sensor patch is transmitted to the mobile integrated computing device via a communication module.

23. The communication module of aspect 22, wherein the signal is transmitted by Bluetooth or WIFI radio signals.

24. The MAID device of aspect 2. wherein the pressure sensor and embedded temperature sensor are used to detect noncompliant entry into the MAID device.

The following is claimed:

1. A system for facilitating administration of a pharmaceutical product, wherein the system comprising:
at least one sensor disposed on body of a user, wherein the at least one sensor is configured for generating at least one physiological data associated with the body; a storage device configured for storing at least one dosage data, wherein the at least one dosage data is prescribed by a medical professional, wherein the at least one dosage data is associated with the user;
a processing device communicatively coupled with the at least one sensor, wherein the processing device is communicatively coupled with the storage device, wherein the processing device is configured for:
analyzing the at least one physiological data and the at least one dosage data; determining a pharmaceutical dose of the pharmaceutical product corresponding to the user based on the analyzing;
and generating a command based on the determining;
and a Mobile Administration Interlocking Device (MAID) configured for provisioning the pharmaceutical product to the user, wherein the MAID is communicatively coupled with the processing device, wherein the MAID comprising:
a first chamber configured for accommodating the pharmaceutical product, wherein the first chamber comprises a first opening, wherein the first opening facilitates dispensing of the pharmaceutical product;
a first actuator is communicatively coupled with the processing device, wherein the first actuator is operably coupled with the first chamber, wherein the first actuator is configured for dispensing the pharmaceutical product, wherein the first actuator is controlled by the processing device based on the command, wherein the first actuator is configured to arrange in at least two states, wherein a first state of the at least two states facilitates dispensing of the pharmaceutical product, wherein a second state of the at least two states prevents access to the pharmaceutical product; and
a second chamber configured for accommodating an opioid antagonist, wherein the second chamber comprises a second sensor, wherein the second sensor is configured for detecting an invalid dispensing action associated with the second chamber, wherein the second chamber comprises a second actuator, wherein the second sensor is coupled with the second actuator, wherein the second actuator is communicatively coupled with the processing device, wherein the second actuator is configured for controlling dispensing of the opioid antagonist based on the detection of the invalid dispensing action, wherein the dispensing of the opioid antagonist facilitates the neutralizing of the opioid.

2. The system of claim 1, the processing device is configured to generate an alert based on the detection of the invalid dispensing action, wherein the system further comprises a communication device configured for transmitting the alert to at least one second user device, wherein the at least one second user device is associated with at least one second user.

3. The system of claim 1 further comprises a biometric sensor configured for verifying the user, wherein the dispensing of the pharmaceutical product is based on the verification of the user, wherein the biometric sensor is communicatively coupled with the processing device, wherein the biometric sensor is configured for generating a user biometric data, wherein the storage device is configured for retrieving a user data corresponding to the user, wherein the processing device is configured for analyzing the user biometric data and the user data to generate a notification, wherein the system further comprises a communication device configured for transmitting the notification to at least one of user device and the at least one second user device.

4. The system of claim 1, wherein the first actuator is coupled with a dispensing sensor, wherein the dispensing sensor is configured to detect dispensing of the pharmaceutical product, wherein the dispensing sensor is configured to generate a dispensing data, wherein the processing device is configured for analyzing the dispensing data to generate an alert, wherein the system further comprises a communication device configured for transmitting the alert to the at least one second user device.

5. The system of claim 1, wherein the storage device is configured for storing at least one of the at least one physiological data and the dispensing data, wherein the processing device is configured for analyzing at least one of the at least one dosage data, the at least one physiological data, and the dispensing data to generate a notification, wherein the system further comprises a communication device configured for transmitting the notification to at least one of the user device and the at least one second user device.

6. The system of claim 1, wherein the MAID further comprises a third chamber configured for storing a deterrent compound and a hardening agent, wherein the third chamber is coupled with a third actuator, wherein the third actuator is configured for:
mixing the deterrent compound and the hardening agent based on the detecting of the invalid dispensing action; and
dispensing the mixture into at least one of the first chamber and the first actuator, wherein the hardening of the mixture prevents dispensing of the pharmaceutical product to the user.

7. A system for facilitating administration of opioid, wherein the system comprising:
at least one sensor disposed on body of a user, wherein the at least one sensor is configured for generating at least one physiological data associated with the body;
a storage device configured for storing at least one dosage data, wherein the at least one dosage data is prescribed by a medical professional, wherein the at least one dosage data is associated with the user;
a processing device communicatively coupled with the at least one sensor, wherein the processing device is communicatively coupled with the storage device, wherein the processing device is configured for:
analyzing the at least one physiological data and the at least one dosage data;
determining a pharmaceutical dose of the opioid corresponding to the user based on the analyzing; and
generating a command based on the determining;
and a Mobile Administration Interlocking Device (MAID) configured for provisioning the opioid to the user, wherein the MAID is communicatively coupled with the processing device, wherein the MAID comprising:
a first chamber configured for accommodating the opioid, wherein the first chamber comprises a first opening, wherein the first opening facilitates dispensing of the opioid;
a first actuator is communicatively coupled with the processing device, wherein the first actuator is operably coupled with the first chamber, wherein the first actuator is configured for dispensing the opioid, wherein first the actuator is controlled by the processing device based on the command, wherein the first actuator is configured to arrange in at least two states, wherein a first state of the at least two states facilitates dispensing of the opioid, wherein a second state of the at least two states prevents access to the opioid; and
a second chamber configured for accommodating an opioid antagonist, wherein the second chamber comprises a second sensor, wherein the second sensor is configured for detecting an invalid dispensing action associated with the second chamber, wherein the second chamber comprises a second actuator, wherein the second sensor is coupled with the second actuator, wherein the second actuator is communicatively coupled with the processing device, wherein the second actuator is configured for controlling dispensing of the opioid antagonist based on the detection of the invalid dispensing action, wherein the dispensing of the opioid antagonist facilitates the neutralizing of the opioid.

8. The system of claim 7, the processing device is configured to generate an alert based on the detection of the invalid dispensing action, wherein the system further comprises a communication device configured for transmitting the alert to at least one second user device, wherein the at least one second user device is associated with at least one second user.

9. The system of claim 7 further comprises a biometric sensor configured for verifying the user, wherein the dispensing of the opioid is based on the verification of the user, wherein the biometric sensor is communicatively coupled with the processing device, wherein the biometric sensor is configured for generating a user biometric data, wherein the storage device is configured for retrieving a user data corresponding to the user, wherein the processing device is configured for analyzing the user biometric data and the user data to generate a notification, wherein the system further comprises a communication device configured for transmitting the notification to at least one of user device and the at least one second user device.

10. The system of claim 7, wherein the first actuator is coupled with a dispensing sensor, wherein the dispensing sensor is configured to detect dispensing of the opioid, wherein the dispensing sensor is configured to generate a dispensing data, wherein the processing device is configured for analyzing the dispensing data to generate an alert, wherein the system further comprises a communication device configured for transmitting the alert to the at least one second user device.

11. The system of claim 7, wherein the storage device is configured for storing at least one of the at least one physiological data and the dispensing data, wherein the processing device is configured for analyzing at least one of the at least one dosage data, the at least one physiological data, and the dispensing data to generate a notification, wherein the system further comprises a communication device configured for transmitting the notification to at least one of the user device and the at least one second user device.

12. The system of claim 7, wherein the MAID further comprises a third chamber configured for storing a deterrent compound and a hardening agent, wherein the third chamber is coupled with a third actuator, wherein the third actuator is configured for:
   mixing the deterrent compound and the hardening agent based on the detecting of the invalid dispensing action; and
   dispensing the mixture into at least one of the first chamber and the first actuator, wherein the hardening of the mixture prevents dispensing of the pharmaceutical product to the user.

13. A system for facilitating administration of an opioid, wherein the system comprising:
   at least one sensor disposed on body of a user, wherein the at least one sensor is configured for generating at least one physiological data associated with the body;
   a storage device configured for storing at least one dosage data, wherein the at least one dosage data is prescribed by a medical professional, wherein the at least one dosage data is associated with the user;
   a processing device communicatively coupled with the at least one sensor, wherein the processing device is communicatively coupled with the storage device, wherein the processing device is configured for:
      analyzing the at least one physiological data and the at least one dosage data;
      determining a pharmaceutical dose of the opioid corresponding to the user based on the analyzing; and
      generating a command based on the determining; and
   a Mobile Administration Interlocking Device (MAID) configured for provisioning the opioid to the user, wherein the MAID is communicatively coupled with the processing device, wherein the MAID comprising:
      a first chamber configured for accommodating the opioid, wherein the first chamber comprises a first opening, wherein the first opening facilitates dispensing of the opioid;
      a first actuator is communicatively coupled with the processing device, wherein the first actuator is operably coupled with the first chamber, wherein the first actuator is configured for dispensing the opioid, wherein first the actuator is controlled by the processing device based on the command, wherein the first actuator is configured to arrange in at least two states, wherein a first state of the at least two states facilitates dispensing of the opioid, wherein a second state of the at least two states prevents access to the opioid; and
      a second chamber configured for accommodating an opioid antagonist, wherein the second chamber comprises a second sensor, wherein the second sensor is configured for detecting an invalid dispensing action associated with the second chamber, wherein the second chamber comprises a second actuator, wherein the second sensor is coupled with the second actuator, wherein the second actuator is communicatively coupled with the processing device, wherein the second actuator is configured for controlling dispensing of the opioid antagonist based on the detection of the invalid dispensing action, wherein the dispensing of the opioid antagonist facilitates the neutralizing of the opioid.

14. The system of claim 13, the processing device is configured to generate an alert based on the detection of the invalid dispensing action, wherein the system further comprises a communication device configured for transmitting the alert to at least one second user device, wherein the at least one second user device is associated with at least one second user.

15. The system of claim 13 further comprises a biometric sensor configured for verifying the user, wherein the dispensing of the opioid is based on the verification of the user, wherein the biometric sensor is communicatively coupled with the processing device, wherein the biometric sensor is configured for generating a user biometric data, wherein the storage device is configured for retrieving a user data corresponding to the user, wherein the processing device is configured for analyzing the user biometric data and the user data to generate a notification, wherein the system further comprises a communication device configured for transmitting the notification to at least one of user device and the at least one second user device.

16. The system of claim 13, wherein the first actuator is coupled with a dispensing sensor, wherein the dispensing sensor is configured to detect dispensing of the opioid, wherein the dispensing sensor is configured to generate a dispensing data, wherein the processing device is configured for analyzing the dispensing data to generate an alert, wherein the system further comprises a communication device configured for transmitting the alert to the at least one second user device.

17. The system of claim 13, wherein the storage device is configured for storing at least one of the at least one physiological data and the dispensing data, wherein the processing device is configured for analyzing at least one of the at least one dosage data, the at least one physiological data, and the dispensing data to generate a notification, wherein the system further comprises a communication device configured for transmitting the notification to at least one of the user device and the at least one second user device.

18. The system of claim 13, wherein the MAID further comprises a third chamber configured for storing a deterrent compound and a hardening agent, wherein the third chamber is coupled with a third actuator, wherein the third actuator is configured for:
   mixing the deterrent compound and the hardening agent based on the detecting of the invalid dispensing action; and
   dispensing the mixture into at least one of the first chamber and the first actuator, wherein the hardening of the mixture prevents dispensing of the pharmaceutical product to the user.

\* \* \* \* \*